US012608886B2

(12) United States Patent
Birenbaum et al.

(10) Patent No.: US 12,608,886 B2
(45) Date of Patent: Apr. 21, 2026

(54) SYSTEMS AND METHODS FOR AUTOMATIC BLOOD VESSEL EXTRACTION

(71) Applicant: Covidien LP, Mansfield, MA (US)

(72) Inventors: Ariel Birenbaum, Raanana (IL); Ofer Barasofsky, Tel Mond (IL); Guy Alexandroni, Yehud-Monosson (IL); Irina Shevlev, Ashdod (IL)

(73) Assignee: Covidien LP, Mansfield, MA (US)

( * ) Notice: Subject to any disclaimer, the term of this patent is extended or adjusted under 35 U.S.C. 154(b) by 231 days.

(21) Appl. No.: 18/279,196

(22) PCT Filed: Feb. 25, 2022

(86) PCT No.: PCT/US2022/018004
§ 371 (c)(1),
(2) Date: Aug. 28, 2023

(87) PCT Pub. No.: WO2022/203814
PCT Pub. Date: Sep. 29, 2022

(65) Prior Publication Data
US 2024/0303927 A1     Sep. 12, 2024

Related U.S. Application Data

(60) Provisional application No. 63/251,616, filed on Oct. 2, 2021, provisional application No. 63/224,786, filed
(Continued)

(51) Int. Cl.
*G06T 17/20*         (2006.01)
*A61B 34/10*         (2016.01)
(Continued)

(52) U.S. Cl.
CPC .............. *G06T 17/20* (2013.01); *A61B 34/10* (2016.02); *G06V 10/26* (2022.01); *G06V 10/44* (2022.01);
(Continued)

(58) Field of Classification Search
CPC . G06T 17/20; G06T 2200/04; G06T 2200/24; G06T 2210/41; A61B 34/10;
(Continued)

(56) References Cited

U.S. PATENT DOCUMENTS 6,999,073  B1 *   2/2006   Zwern ................... G06T 17/005
                                                          345/581
2012/0203530  A1 *   8/2012   Sharma ................... G16H 50/50
                                                          703/9
(Continued)

FOREIGN PATENT DOCUMENTS

EP          4390845  A1 *   6/2024   ............. G06T 17/20

OTHER PUBLICATIONS

Cemil Kirbas et al: "A review of vessel extraction techniques and algorithms", ACM Computing Surveys, ACM, New York, NY, US, vol. 36, No. 2, Jun. 1, 2004 (Jun. 1, 2004),pp. 81-121.
(Continued)

*Primary Examiner* — Sing-Wai Wu
(74) *Attorney, Agent, or Firm* — Weber Rosselli & Cannon LLP

(57)          ABSTRACT

Systems and methods of image processing include a processor in communication with a display and a computer readable recording medium having instructions executed by the processor to read a three-dimensional (3D) image data set from the computer-readable recording medium and automatically generate a tree structure of blood vessels based on patient images of the image data set using a neural network. Manually- and/or semi-automatically-generated 3D models
(Continued)

of blood vessels are used to train the neural network. The systems and methods involve segmenting and classifying blood vessels in the 3D image data set using the trained neural network, closing holes, finding roots and endpoints in the segmentation, finding shortest paths between the roots and endpoints, selecting most probable paths, combining most probable paths into directed graphs, solving overlaps between directed graphs, and creating 3D models of blood vessels based on the directed graphs.

20 Claims, 51 Drawing Sheets

Related U.S. Application Data on Jul. 22, 2021, provisional application No. 63/166,244, filed on Mar. 26, 2021.

(51) Int. Cl.

| | |
|---|---|
| *G06V 10/26* | (2022.01) |
| *G06V 10/44* | (2022.01) |
| *G06V 10/764* | (2022.01) |
| *G06V 10/774* | (2022.01) |
| *G06V 10/82* | (2022.01) |
| *G06V 10/86* | (2022.01) |
| *G06V 20/50* | (2022.01) |
| *G16H 50/50* | (2018.01) |

(52) U.S. Cl.
CPC ............ *G06V 10/764* (2022.01); *G06V 10/82* (2022.01); *G06V 10/86* (2022.01); *G06V 20/50* (2022.01); *G16H 50/50* (2018.01); *A61B 2034/105* (2016.02); *G06T 2200/04* (2013.01); *G06T 2200/24* (2013.01); *G06T 2210/41* (2013.01); *G06V 10/774* (2022.01); *G06V 2201/031* (2022.01)

(58) Field of Classification Search
CPC .. A61B 2034/105; G16H 50/50; G06V 10/86; G06V 10/82; G06V 10/44; G06V 10/26; G06V 20/50; G06V 10/764; G06V 2201/031; G06V 10/774
See application file for complete search history.

(56) References Cited

U.S. PATENT DOCUMENTS

| | | | |
|---|---|---|---|
| 2017/0262981 A1* | 9/2017 | Gulsun ............. | G06F 18/24323 |
| 2021/0209766 A1* | 7/2021 | Cho ........................... | G06T 7/11 |
| 2022/0164957 A1* | 5/2022 | Jia ........................... | G16H 50/20 |
| 2024/0041534 A1* | 2/2024 | Panse .................... | G06T 7/0016 |

OTHER PUBLICATIONS

Keshwani Deepak et al: "TopNet: Topology Preserving Metric Learning for Vessel Tree Reconstruction and Labelling" In : Anne L. Martel et al.: "Medical Image Computing and Computer Assisted Intervention MICCAI 2020", Oct. 4, 2020 (Oct. 4, 2020), Springer International Publishing.
PCT Search Report and Written Opinion issued in PCT Application No. PCT/US2022/018004 dated Jun. 15, 2022.

\* cited by examiner

<u>400</u>

602

604

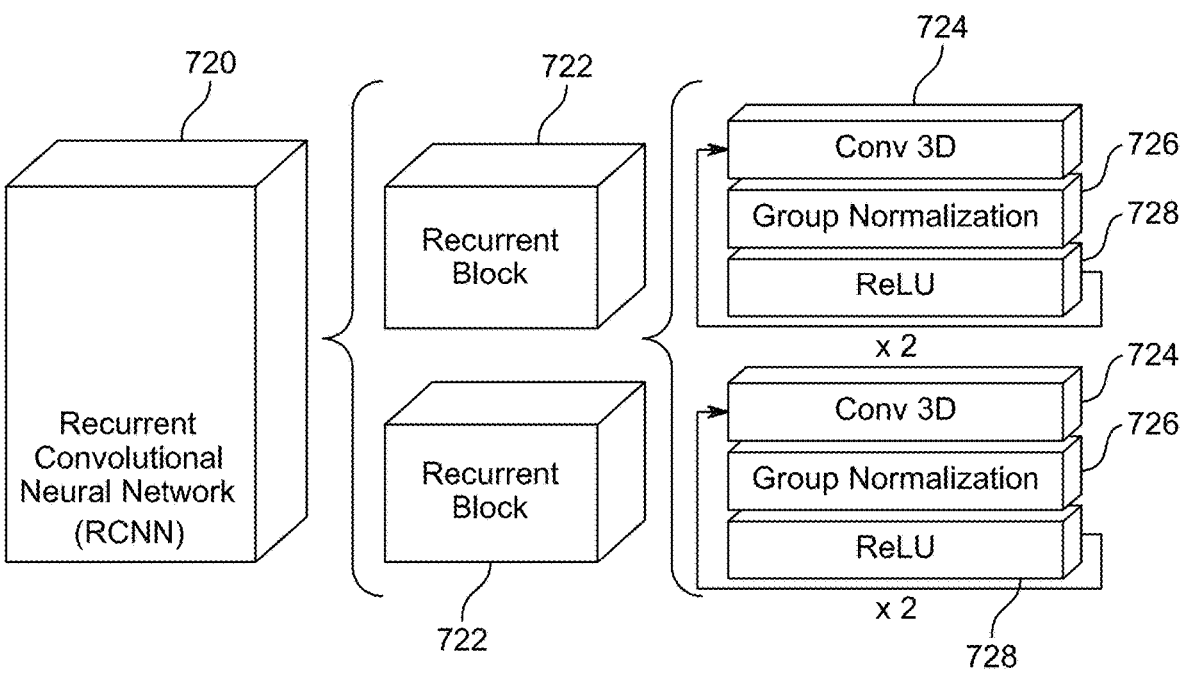
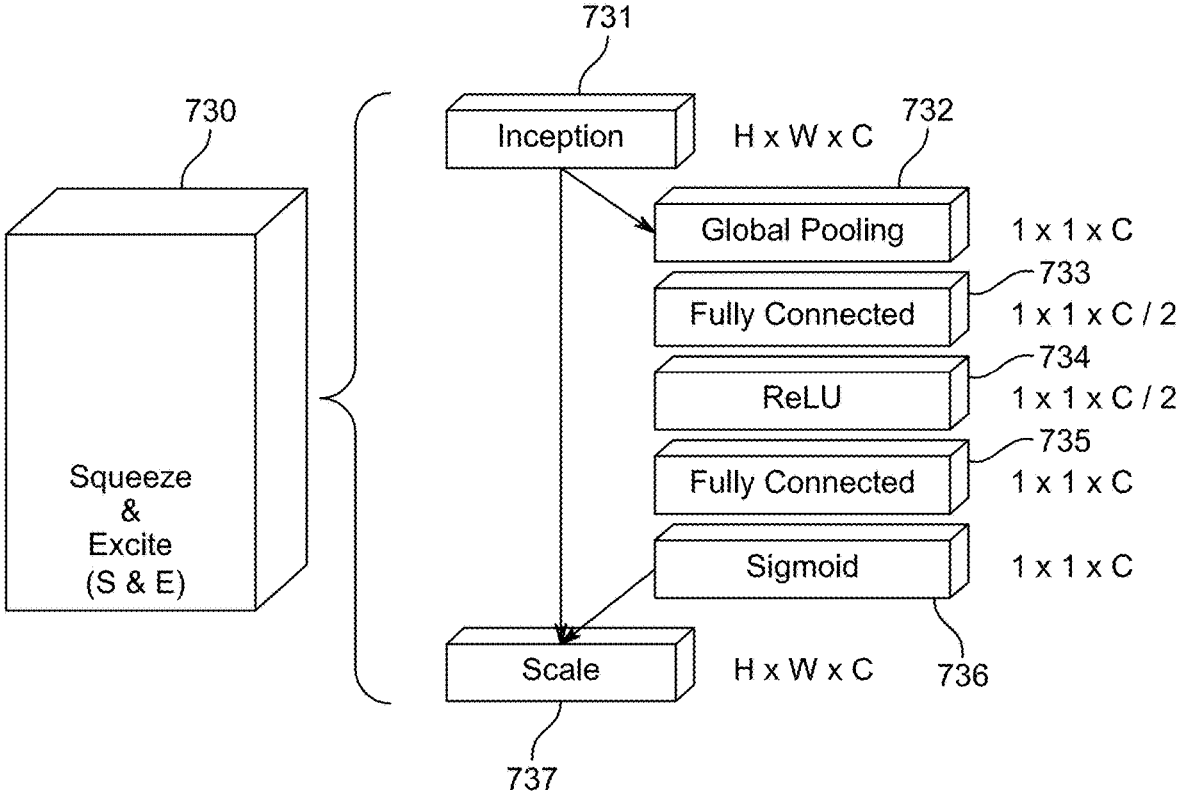
FIG. 7B

1300

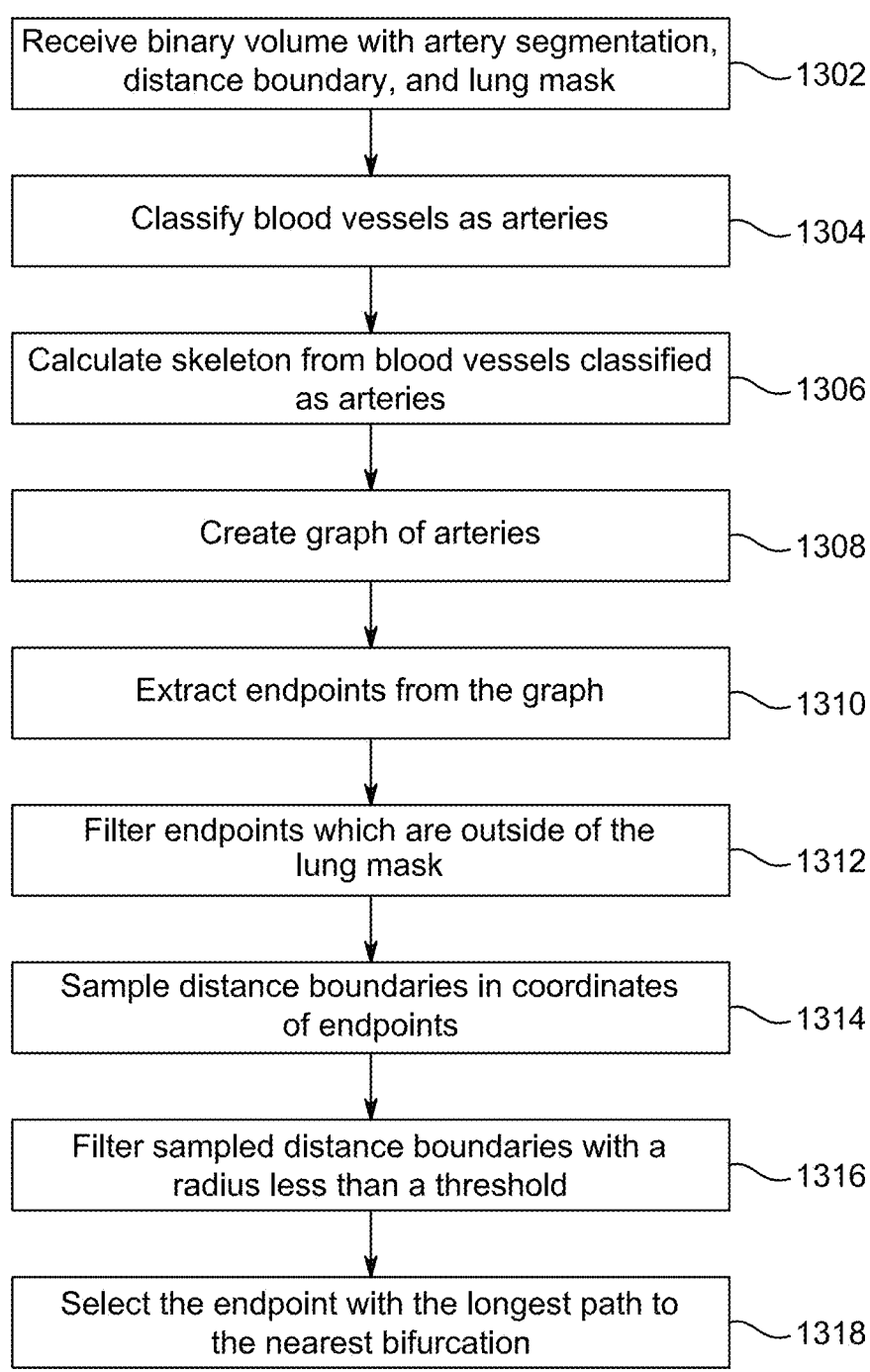

Receive binary volume with artery segmentation, distance boundary, and lung mask ~1302

Classify blood vessels as arteries ~1304

Calculate skeleton from blood vessels classified as arteries ~1306

Create graph of arteries ~1308

Extract endpoints from the graph ~1310

Filter endpoints which are outside of the lung mask ~1312

Sample distance boundaries in coordinates of endpoints ~1314

Filter sampled distance boundaries with a radius less than a threshold ~1316

Select the endpoint with the longest path to the nearest bifurcation ~1318

FIG. 13

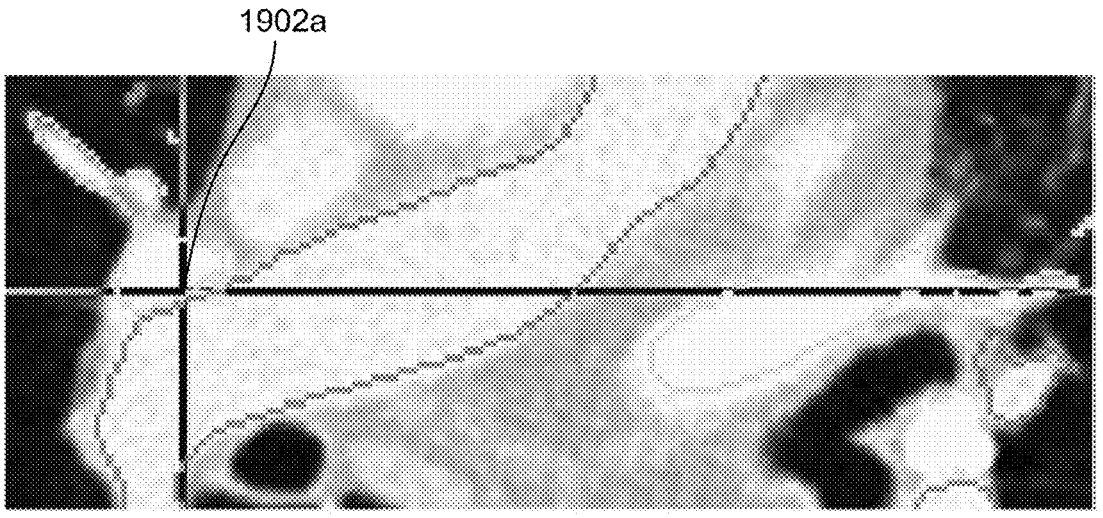
FIG. 19A
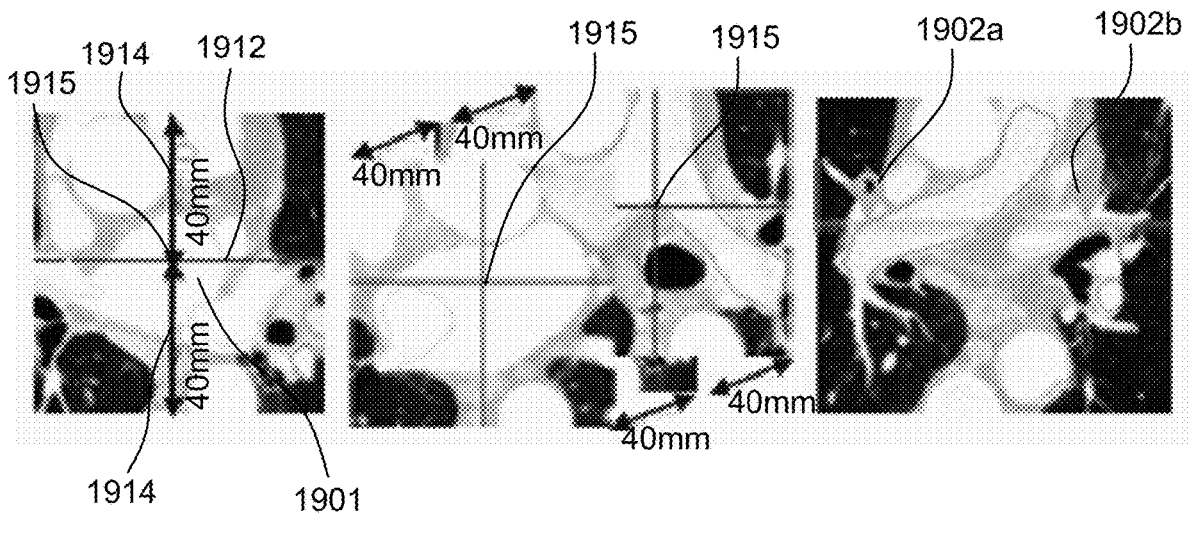
FIG. 19B          FIG. 19C          FIG. 19D

2300

2601

2602

Distance between
center lines

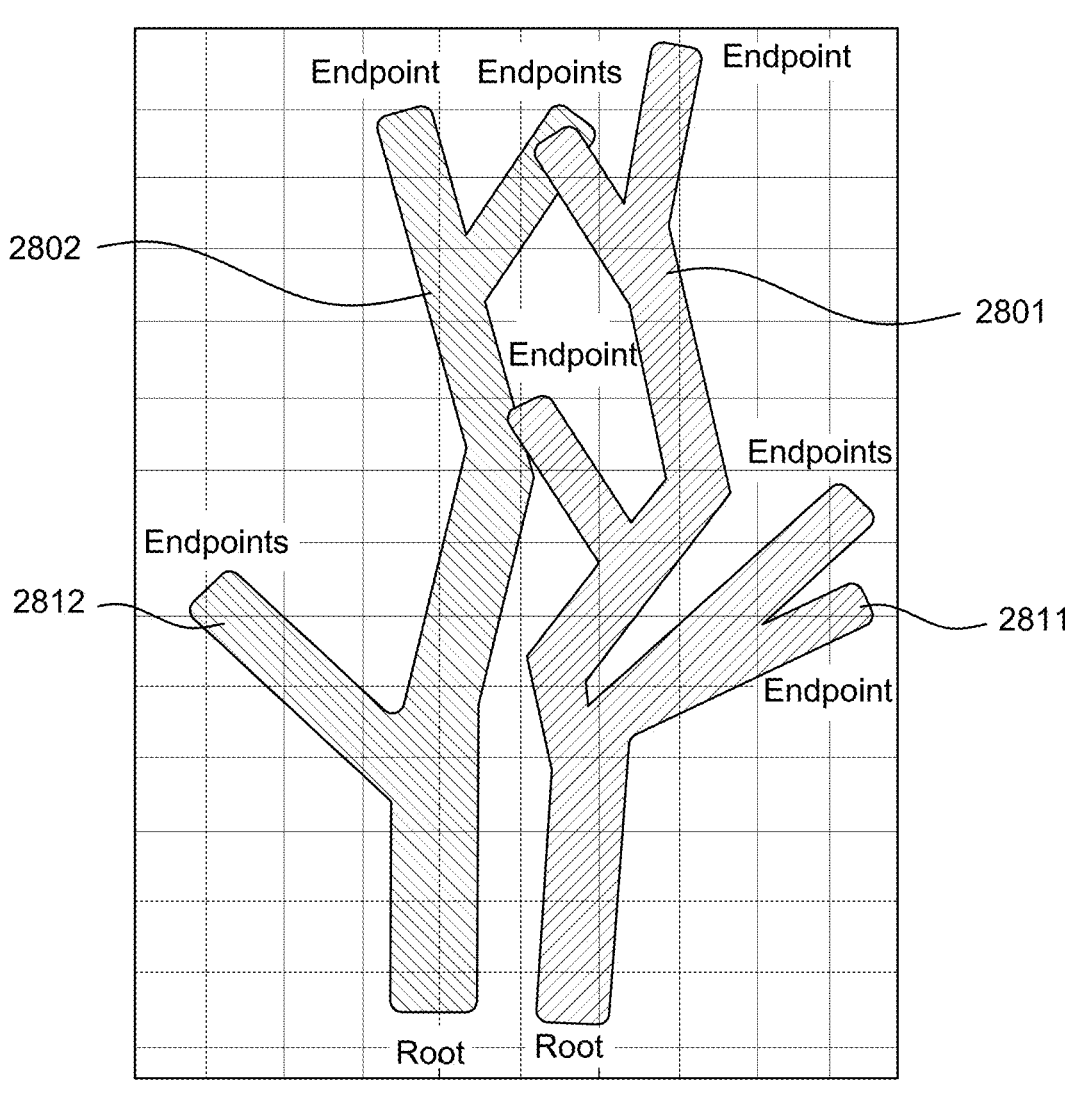
FIG. 28

3111

3401                                    3402

3500

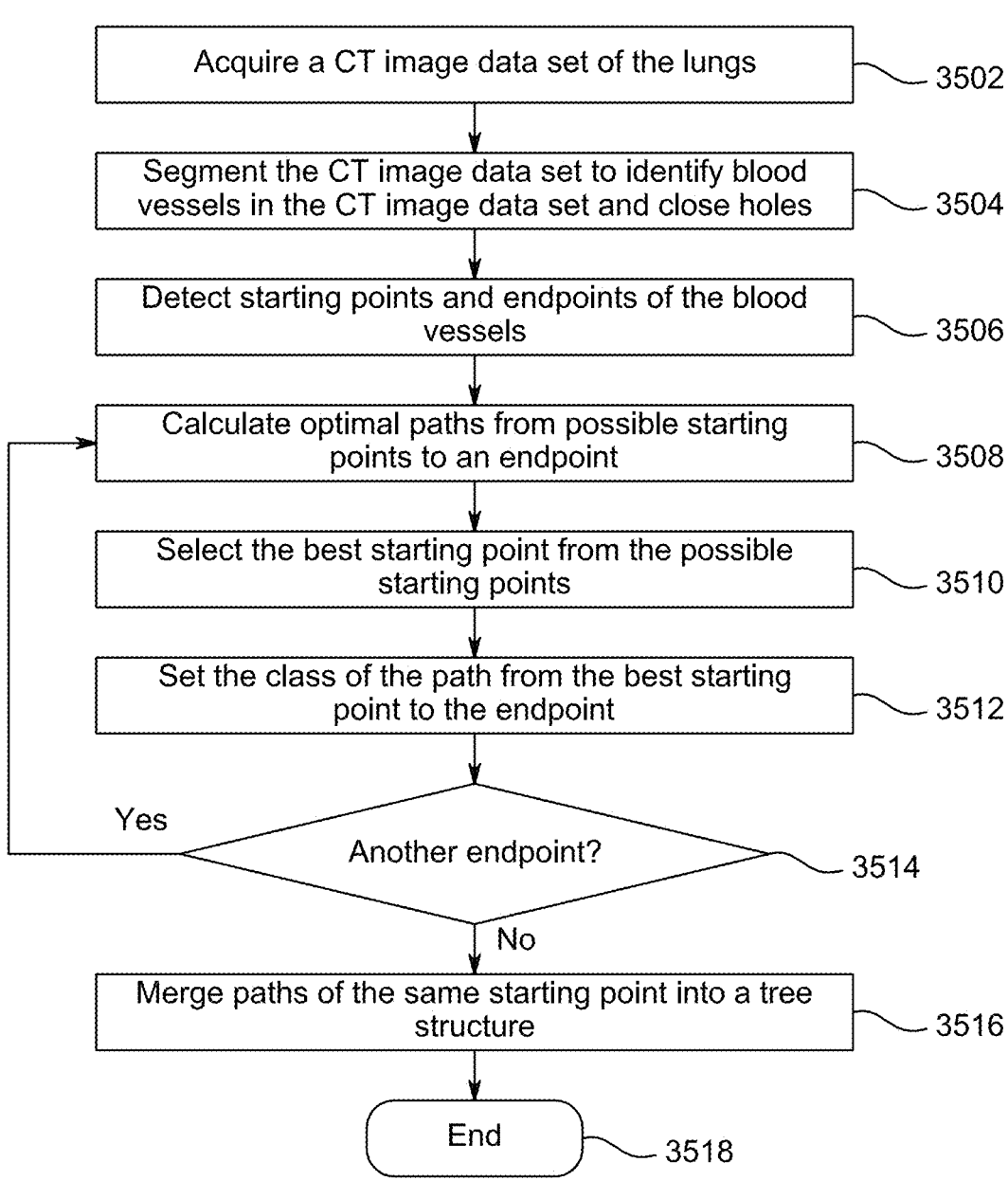

Acquire a CT image data set of the lungs — 3502

Segment the CT image data set to identify blood vessels in the CT image data set and close holes — 3504

Detect starting points and endpoints of the blood vessels — 3506

Calculate optimal paths from possible starting points to an endpoint — 3508

Select the best starting point from the possible starting points — 3510

Set the class of the path from the best starting point to the endpoint — 3512

Yes

Another endpoint? — 3514

No

Merge paths of the same starting point into a tree structure — 3516

End — 3518

⊕ : Endpoint 4001          4002

— 4001

— 4001

SYSTEMS AND METHODS FOR AUTOMATIC BLOOD VESSEL EXTRACTION

FIELD

This disclosure relates to systems and methods to create 3D anatomic tree structures, which may be used to generate a 3D mesh model of blood vessels of a portion of a patient's body. In particular, the disclosure is directed to systems and methods of automatically creating 3D tree structures of the vasculature of a portion of a patient's body, e.g., the lungs, using a neural network trained by manually and/or semi-automatically created 3D vascular tree structures.

BACKGROUND

In many domains there is a need for segmenting and/or classifying voxels in volumetric data. In medical imaging, there are many open source and proprietary systems that enable manual segmentation and/or classification of medical images such as CT images. These systems typically require a clinician or a technician in support of a clinician to manually review the CT images and paint in the blood vessels or other structures manually, sometimes pixel by pixel. The user normally must scroll through many 2D slices and mark many pixels to obtain an accurate 3D segmentation or classification. As can be appreciated, such manual efforts are tedious and time-consuming, which renders such methods difficult to utilize for any type of surgical planning.

SUMMARY

In one aspect, the disclosure features a system including a processor and a memory. The memory has stored thereon a neural network and instructions, which, when executed by the processor, cause the processor to: cause the neural network to segment blood vessels in volumetric images of a portion of a body, yielding segmented blood vessels. The instructions, when executed by the processor, further cause the processor to detect roots of the segmented blood vessels and detect endpoints of the blood vessels. The instructions, when executed by the processor, further cause the processor to determine the shortest path from each endpoint to each of the roots, and combine the shortest paths to the roots into directed graphs.

Implementations of the system may include one or more of the following features. The instructions, when executed by the processor, further cause the processor to generate a 3D model based on the directed graphs. The neural network may use a 3D U-Net style architecture.

The instructions, when executed by the processor, may cause the processor to receive annotated volumetric images in which blood vessels are identified and train the neural network with the annotated volumetric images. The instructions, when executed by the processor, may cause the processor to segment blood vessels in the volumetric images using a classical image segmentation method, yielding the annotated volumetric images in which blood vessels are identified. The classical image segmentation method may include an edge-based method, a region-based method, or a thresholding method.

The neural network may include a segmentation layer and the instructions, when executed by the processor, may cause the processor to train the segmentation layer with a dice loss. The dice loss may be a weighted dice loss. The neural network may include a topological layer and the instructions, when executed by the processor, may cause the processor to train the topological layer with a topological loss. The neural network may include a classification layer and the instructions, when executed by the processor, may cause the processor to train the classification layer with a cross-entropy loss, a consistency loss, or both a cross-entropy loss and a consistency loss.

The neural network may include an encoder that processes the volumetric images and outputs an encoder output, a first decoder coupled to the output of the encoder and that generates a segmentation probability map based on the encoder output, and a second decoder coupled to the output of the encoder and that generates a topological embedding vector, a distance map, and a classification probability map (e.g., an artery and vein probability map) based on the encoder output.

The encoder, the first decoder, and the second decoder may each include recurrent convolutional neural networks and squeeze and excite blocks coupled to the recurrent convolutional neural networks, respectively. The second decoder may include a convolution function and a sigmoid activation function that process the topological embedding vector and output the classification probability map. The second decoder may include a convolution function and a rectified linear unit that process the topological embedding vector and output the distance map.

The portion of the body may be an organ, neck, upper body, or lower body. The organ may be a brain, lung, kidney, liver, stomach, intestine, prostate, rectum, or colon.

In another aspect, the disclosure features a method. The method includes receiving a three-dimensional (3D) image data set of a portion of the body and segmenting the 3D image data set to identify blood vessels in the 3D image data set using a neural network model. The method also includes classifying the blood vessels using the neural network model, detecting starting points of the processed blood vessels, and detecting endpoints of the processed blood vessels. The method also includes, for each endpoint, calculating optimal paths from possible starting points to the endpoint, selecting the best starting point from the possible starting points, and setting a class of the path from the best starting point to the endpoint. The method also includes merging paths of the same starting point into a tree structure.

Implementations of the method may include one or more of the following features. The blood vessels may be arteries or veins. Detecting starting points and ending points may be performed using a neural network model. The method may include training a topological layer of the neural network model using a topological loss. The method may include training a segmentation layer of the neural network model using dice loss. The method may include weighting the dice loss. Weighting the dice loss may include applying a weight of 0 to the dice loss for unannotated peripheral blood vessels and applying a weight of 1 for annotated peripheral blood vessels.

The method may include computing Euclidian distances of topological embedding vectors, computing topological distances of the topological embedding vectors, and training the neural network model to match the Euclidian distance of topological embedding vectors to corresponding topological distances of the topological embedding vectors. Computing the topological distances of the topological embedding vectors may include computing the topological distances of the topological embedding vectors based on total topological loss. The purpose of the topological loss is to increase the distance between feature spaces of the arteries and veins in the neural network space. The total topological loss may be the sum of topological losses for pairs of points divided by the number of the pairs of points; the topological loss for the pair of points may be a value of an L1 smooth loss function of the pair of points, if the pair of points are in the same class; and the topological loss for the pair of points may be the maximum of 0 or 1/K multiplied by the difference between the constant K and an absolute value of the difference between network topological layer values corresponding to the pair of points, if the pair of points are not in the same class.

The image data set may be a computed tomography (CT) data set. The method may include generating a 3D mesh model from the tree structure. The method may include displaying the 3D mesh model in a user interface. The method may include presenting a user interface enabling a user to select a starting point, an endpoint, and a path of the blood vessel.

In another aspect, the disclosure features a method of generating directed graphs of blood vessels. The method includes receiving a three-dimensional (3D) image data set of a portion of a body and processing the 3D image data set with a neural network to generate a segmentation probability map of blood vessels in the 3D image data set. The method also includes closing at least one hole of the blood vessel in the segmentation probability map. The method also includes detecting starting points of the blood vessels and detecting endpoints of the blood vessels. The method also includes, for each endpoint, tracking the shortest path from the endpoint to each of the starting points, yielding probable paths and selecting the most probable path from the probable paths. The method also includes merging paths having a common starting point to one directed graph and solving for at least one overlap between directed graphs.

Implementations of the method may include one or more of the following features. The portion of the body may be a lung and detecting starting points of the blood vessels may include detecting starting points of the blood vessels at or near the heart. The method may include filtering the segmentation probability map with a first threshold, yielding a first original segmentation, adding voxels to the first original segmentation, yielding a first extended segmentation, dilating the first extended segmentation, and removing voxels with low attenuation values from the first extended segmentation, yielding an updated segmentation. The method may include calculating a skeleton of the updated segmentation and adding the skeleton to the first original segmentation.

The first threshold may be between about 0.1 and 0.4. The method may include filtering the segmentation probability map with a second threshold, yielding a second original segmentation, calculating local attenuation value statistics based on the 3D image data set, adding voxels that have neighboring voxels of the second original segmentation with the same attenuation value statistics, yielding a second extended segmentation, and combining the first and second extended segmentations, yielding the updated segmentation. The second threshold may be about 0.5. Tracking the shortest path from the endpoint to each of the starting points may include tracking the shortest path from the endpoint to each of the starting points using Dijkstra's algorithm. The portion of the body may be a brain, lung, kidney, liver, stomach, intestine, prostate, rectum, or colon.

BRIEF DESCRIPTION OF THE DRAWINGS

Various exemplary aspects are illustrated in the accompanying figures. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

FIGS. 7A and 7B is a block diagram that illustrates an example of the encoder of the neural network of FIG. 3;

FIG. 13 is a flowchart that illustrates a method of detecting roots for arteries;

FIGS. 18A-22 are diagrams that illustrate a method for closing holes in a segmentation;

FIG. 28 is a diagram that illustrates a blood vessel map in which endpoints of blood vessels are detected;

FIG. 35 is a flow diagram that illustrates an example of a method of generating 3D models of blood vessels in accordance with the disclosure;

DETAILED DESCRIPTION

Figure 1:
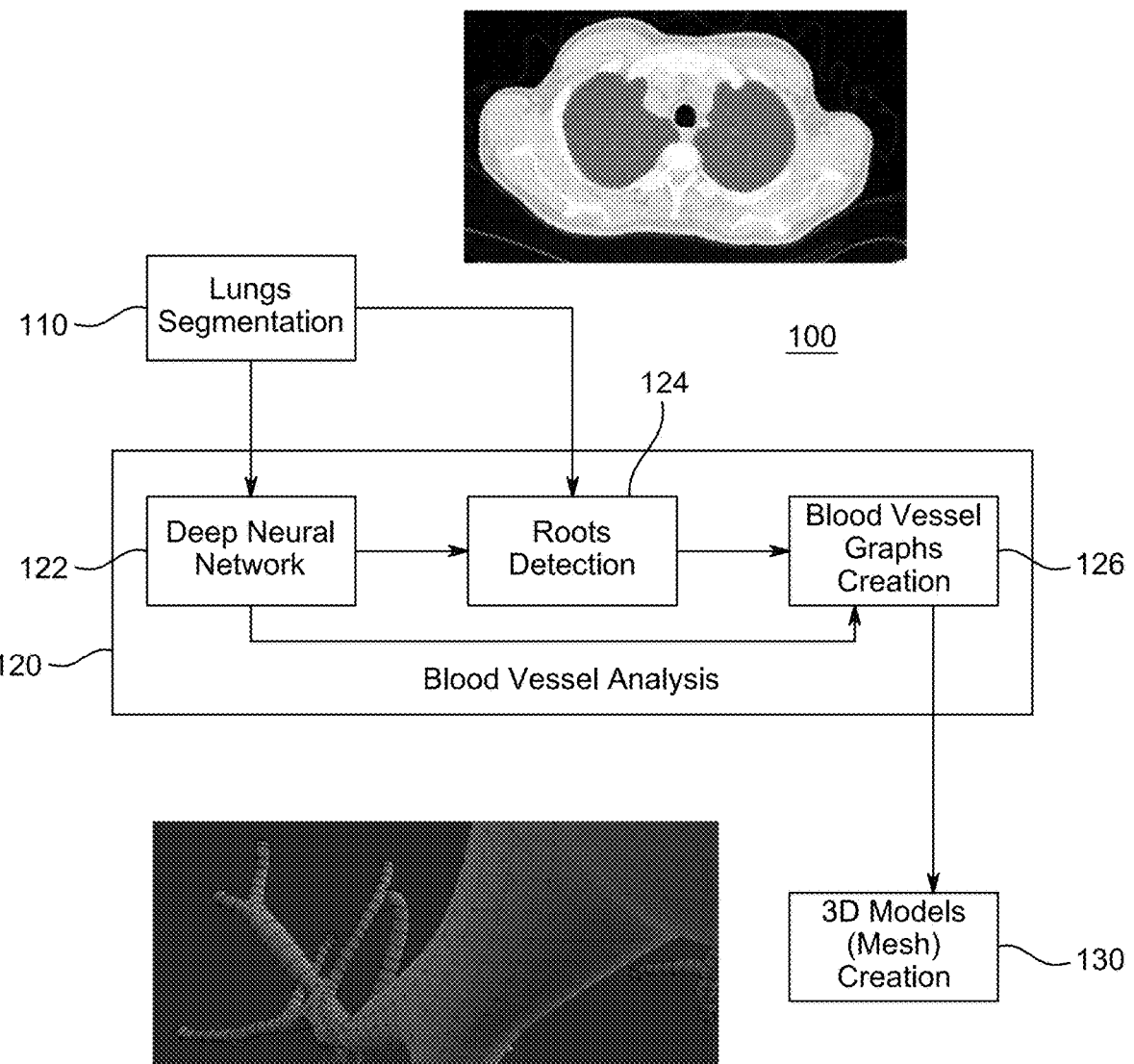
FIG. 1 is a block diagram of a system for generating 3D models of arteries and veins in accordance with the disclosure.

This disclosure is directed to improved techniques and methods of automatically extracting blood vessels, e.g., blood vessels of the lungs, from a 3D image data set. These techniques and methods may form part of an algorithm pipeline for generating a 3D model of pulmonary blood vessels using deep learning techniques. The algorithm pipeline may include annotating a 3D image data set, e.g., CT images, segmenting (e.g., via a semantic segmentation method) and classifying the 3D image data set, finding roots (e.g., via a root detection method), closing segmentation holes, finding endpoints (e.g., via an end-point detection method), generating directed graphs, and creating the 3D models based on the directed graphs. Generating directed graphs may include selecting roots, creating shortest paths, merging paths into trees, and/or performing an overlap analysis on the trees. Given a patient CT volume, the methods of this disclosure automatically create 3D anatomical trees of the lungs' vasculature.

The methods include segmentation, which separates the CT images into separate objects. In the case of the segmentation of the lungs, the purpose of the segmentation is to separate the objects that make up the airways and the vasculature (e.g., the luminal structures) from the surrounding lung tissue. The methods also include generating directed graph structures that model the patient's vasculature. The arteries and veins are separated into different graph structures. The model is later used to generate a 3D object that can be rendered and manipulated in a planning application. This allows clinicians to plan procedures based on which blood vessels should be resected (e.g., in surgery), and which blood vessels should be avoided (e.g., in surgery or ablation procedures). The methods of this disclosure may rely on manually- and/or semi-automatically-created tree structures, which enable creation of ground-truth 3D models used for neural network training and evaluations identifying structures within 3D image data and 3D models derived therefrom. The improved identification of structures allows for additional analysis of the images and 3D models and enables accurate surgical or treatment planning. The methods of the disclosure may be applied to planning lung cancer ablation therapy, segmentectomy, or lobectomy.

The pulmonary vasculature enters the left atrium of the heart. There are usually four pulmonary veins. The pulmonary trunk exits the right ventricle of the heart. In one aspect, a method of this disclosure creates 3D models of the pulmonary vasculature starting from the heart to the periphery of the lungs based on segmented blood vessels. The 3D model models the arteries and veins of the vasculature trees in a tree data structure, such as a directed graph, to enable, among other functions, highlighting of a subsection of the vasculature tree and visualizing of the vasculature tree to a particular generation. The methods of this disclosure may minimize or eliminate the need for manual editing of the 3D model.

One challenge associated with visualization is that segmentation of the mediastinum region results in a low contrast between pulmonary blood vessels and surrounding anatomy. Classification may also be a challenge because arteries and veins may touch each other at some points and have no contrast between them. For classification in the lung region, the challenges include large anatomical variation and the arteries and veins touch at some points and have little to no contrast between them.

To improve visualization, the systems and methods of this disclosure may utilize some anatomical information to improve the deep neural network models. The anatomical information may include connectivity information. For example, every blood vessel can be traced from the periphery to the heart. The anatomical information may also include central region information with low anatomical variation from the heart to the hilum, i.e., the entrance to a lung. The anatomical information may also include peripheral region information, such as airways that often accompany arteries.

The methods of this disclosure may be performed by an automatic system framework 100 for three-dimensional (3D) modeling of blood vessels, e.g., pulmonary blood vessels, as illustrated in FIG. 1. The automatic system framework 100 may include a lung segmentation module 110 that acquires or receives an image data set, e.g., a CT image data set, of the lungs, and performs lung segmentation. The lung segmentation module 110 may acquire or receive the image data set from an imaging device. Alternatively, or additionally, the lung segmentation module 110 may read an image data set of the lungs from a memory storing the image data set. The lung segmentation module 110 semantically segments the lungs using an existing deep neural network model. The imaging device may incorporate any imaging modality suitable for capturing and segmenting two-dimensional images of the lungs. While the disclosure refers to lungs, aspects of this disclosure may be applied to other vascularized portions of a patient's body such as organs, the lower body, the upper body, limbs, or tissue volumes.

The automatic system framework 100 may also include a blood vessel analysis module 120, which performs blood vessel analysis based on the segmented lung generated by the lung segmentation module 110. The blood vessel analysis module 120 includes a deep neural network 122, a roots detection module 124, and a blood vessel graphs creation module 126. The blood vessel analysis includes identifying blood vessels in the image data set and processing the identified blood vessels with a deep neural network model of the deep neural network 122. The deep neural network 122 may be based on a deep convolutional network architecture. The deep neural network 122 may also be implemented by a recurrent unit. An add-on module implementing a channel attention mechanism may be added to the deep convolutional network architecture to improve performance. The channel attention mechanism may be squeeze and excitation networks. Implemented by a recurrent unit. The automatic system framework 100 may also include a 3D mesh generation module 130 that generates a 3D mesh based on the blood vessel graphs or tree structures generated by the blood vessel graphs creation module 126. The automatic system framework 100 may be implemented by applications or instructions stored in memory of a computer system, e.g., system 4200 of FIG. 42, and executed by a processor of the computer system.

Figure 2:
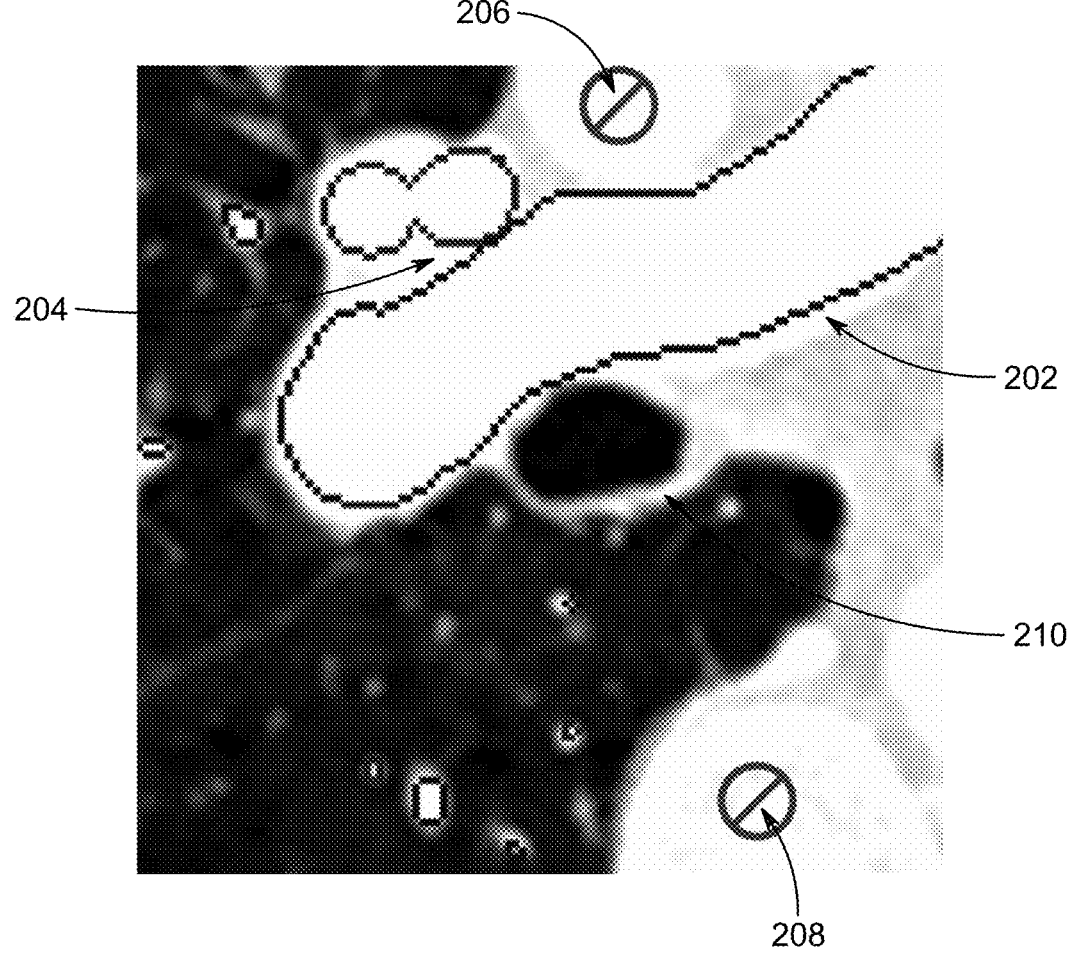
FIG. 2 is a schematic diagram that illustrates challenges addresses by aspects of the disclosure.

As illustrated in FIG. 2, the segmentation algorithm performed by the lungs segmentation module 110 may face a variety of challenges in segmenting images. The challenges include identifying the outline of vessels in the mediastinum 1202, identifying the outline of arteries "touching" veins 1204, excluding unwanted vessels 1206, 1208, e.g., the aorta, excluding airway walls 1210, and avoiding "loops," "holes," discontinuities, and leakages.

Figure 3:
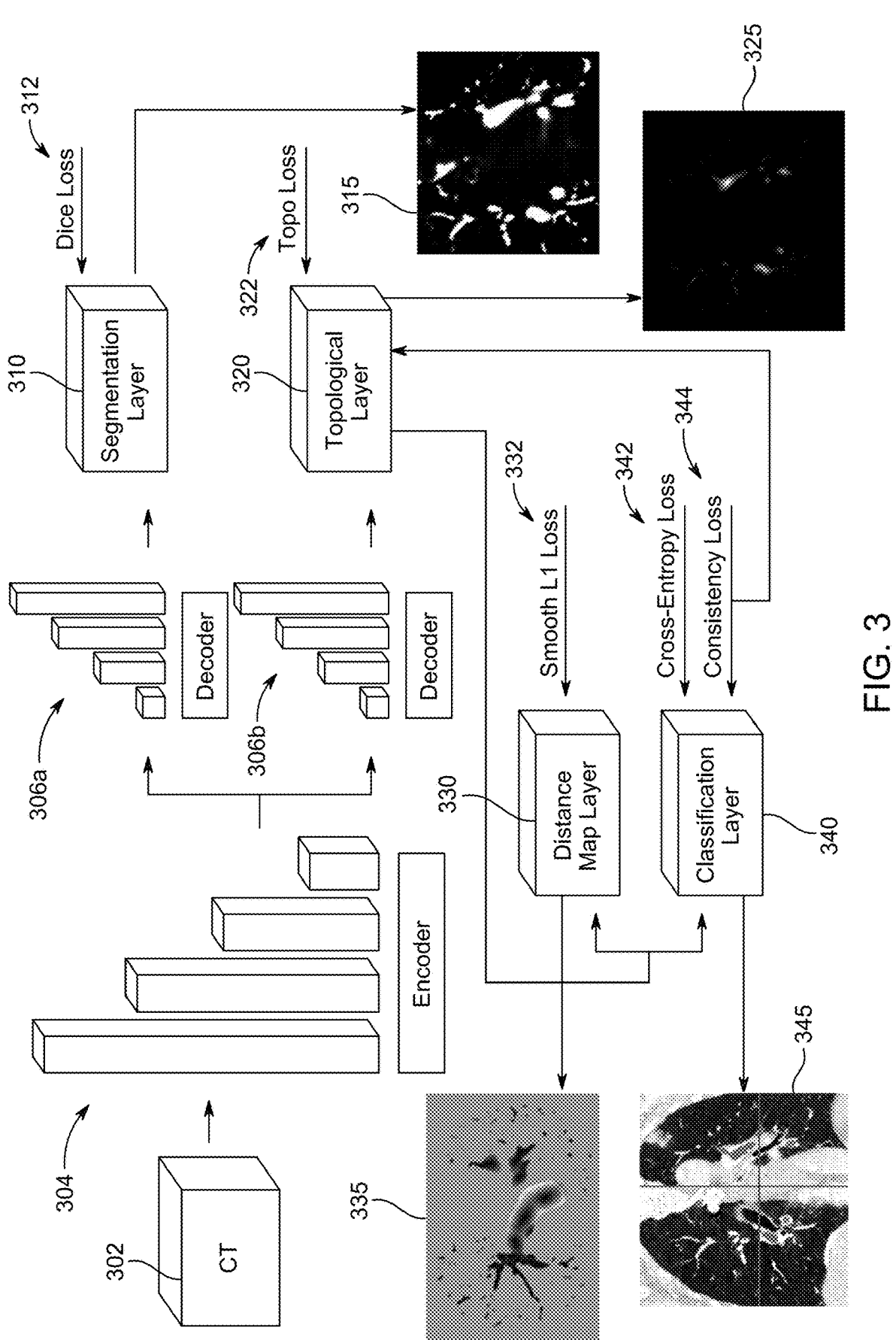
FIG. 3 is a block diagram that illustrates an example of a neural network according to aspects of the disclosure.

FIG. 3 shows an example of a neural network that may be used in the systems and methods of this disclosure to address at least the challenges described above. The deep neural network includes an encoder 304, decoders 306a, 306b, a segmentation layer 310, a topological layer 320, a distance map layer 330, and a classification layer 340. The encoder 304 encodes images, such as CT images 302, to generate encoded data. The decoders 306a, 306b decode the encoded data.

The segmentation layer 310 segments the decoded data from the decoder 306a using dice loss 312, an example of which is described herein, to generate a segmentation map 315. The segmentation map 315 includes, for each voxel, a probabilities that the voxel is a blood vessel. The topological layer 320 determines the topological distances between points in the decoded data from the decoder 306a using consistency loss 344 and/or topological loss 322, an example of which is also described herein, to obtain topological embedding vectors 325. The distance map layer 330 determines the Euclidian distances between points in the topological embedding vectors from the topological layer 320 using smooth L1 loss 332, an example of which is also described herein, to obtain a distance map 335.

The classification layer 340 generates a classification map 345, which includes, for each voxel, a probability that the voxel is an artery or vein. The classification map 345 is illustrated in FIG. 3 as being overlayed on a CT image. The classification layer 340 generates a classification map 345 based on the topological embedding vectors from the topological layer 320 using cross-entropy loss 342 and consistency loss 344. Each topological embedding vector represents each voxel. The topological embedding vectors indicate the topological distances between pairs of points corresponding to pairs of voxels. Generate blood vessel trees. Graph-like structures from which you can generate the The consistency loss 344 addresses the situation where the result of the classification layer 340 and the result of the topological layer 320 are inconsistent. For example, the classification layer 340 may indicate that two points belong to the same blood vessel, while the topological layer 320 may indicate that the two points belong to different blood vessels. Or, conversely, the classification layer 340 may indicate that two points belong to different blood vessels, while the topological layer 320 may indicate that the two points belong to the same blood vessel. The consistency loss 344 smooths the inconsistencies between classification layer 340 and the topological layer 320.

Figure 4:
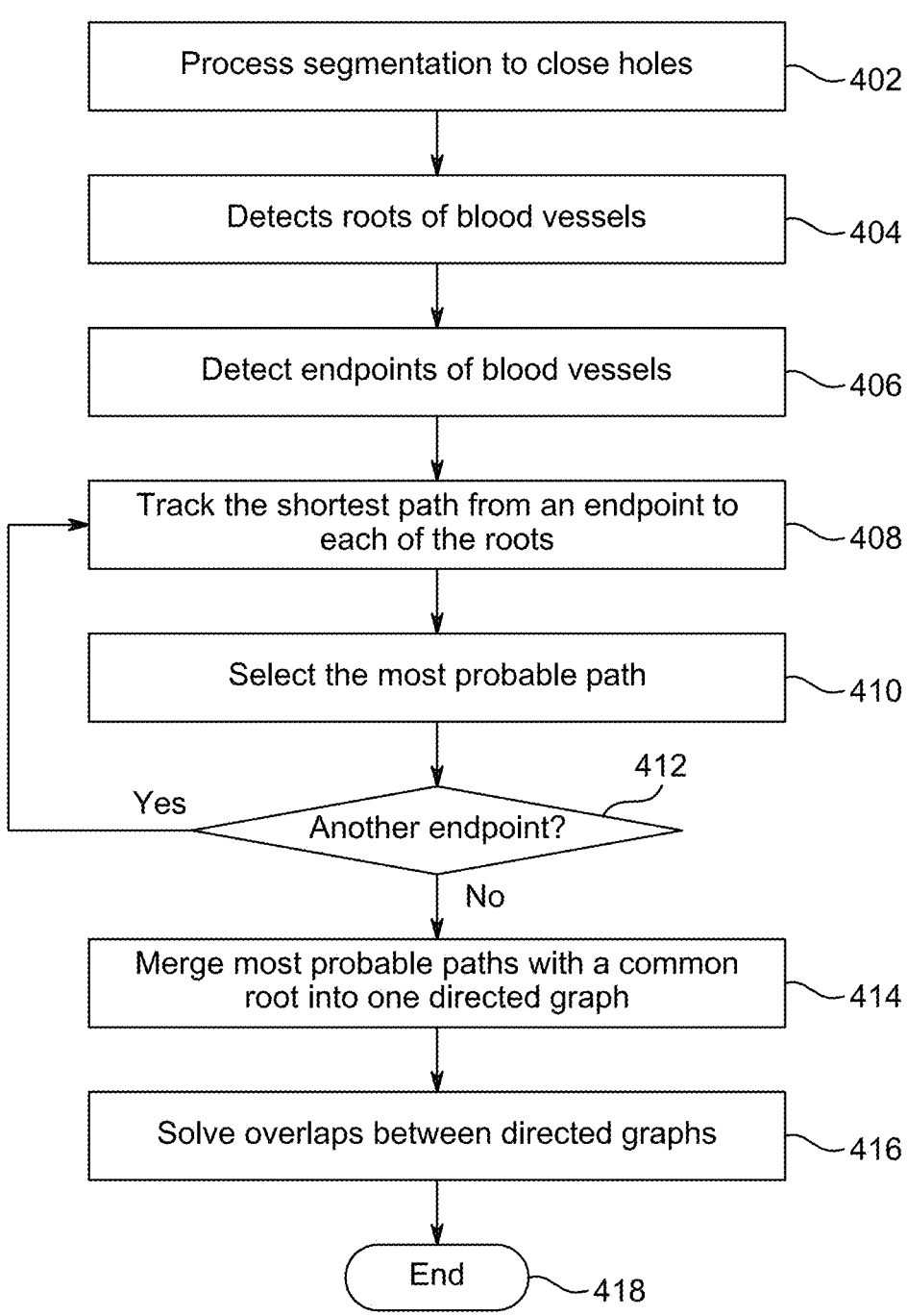
FIG. 4 is a flowchart that illustrates a method including blood vessel analysis according to aspects of the disclosure.

After 3D probability maps of the segmentation and classification of the patient's CT scan are estimated in a first phase, the estimated 3D probability maps are used to create directed graphs representing pulmonary vasculature in a second phase. In the second phase, paths may be tracked from the vasculature periphery towards the heart. Then the paths are merged into graphs. FIG. 4 illustrates an example of a method that implements the first and second phases.

At block 401, a neural network is trained with dice loss, topological loss, and annotated CT images, in which blood vessels are manually and/or semi-automatically segmented and classified using, for example, suitable annotation tools described herein. The training of the neural network may be performed on hardware separate from the system 4200 of FIG. 42. The neural network may be trained using dedicated hardware with sufficient processing power, for example, a system that includes multiple powerful Graphical Processing Units or a comparable system in the cloud. Alternatively, or additionally, the neural network may be trained with annotated CT images that have been segmented using a classical image segmentation technique to segment blood vessels in the CT images. The classical image segmentation technique may include, for example, an edge-based technique, a region-based technique, or a thresholding technique.

Figure 5A:
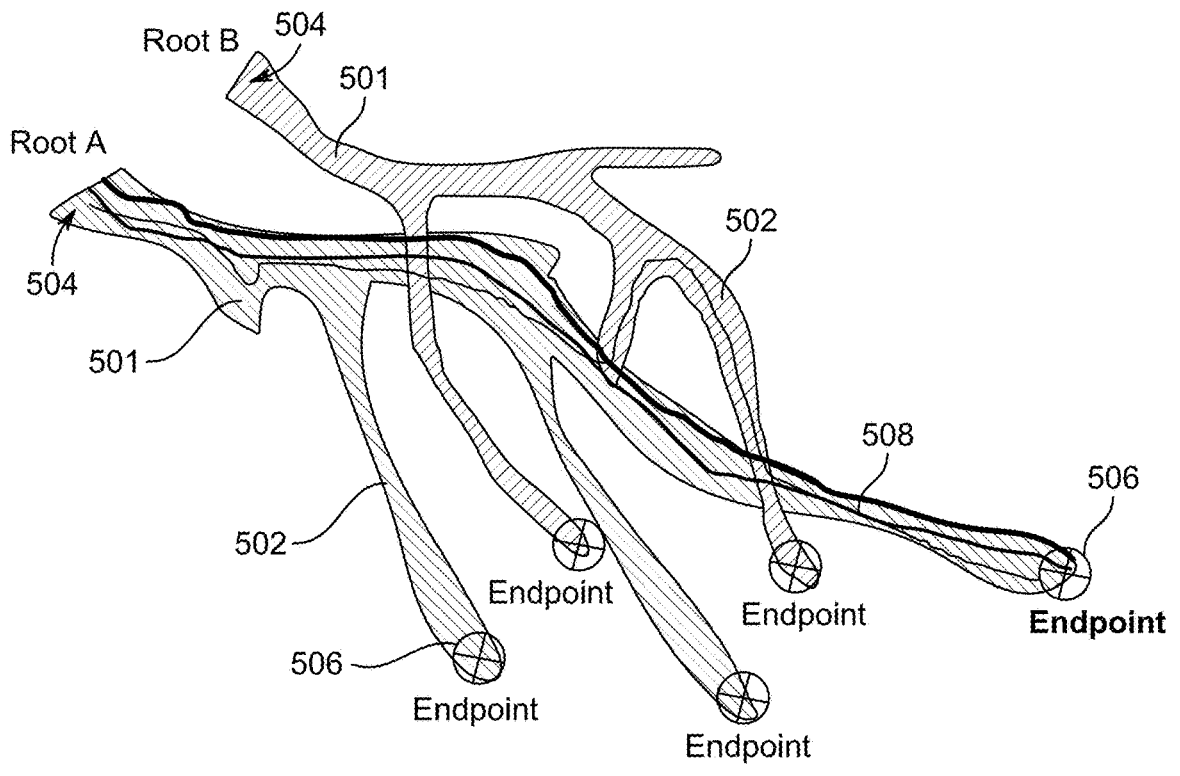
FIGS. 5A-5C are diagrams that illustrate aspects of the method of performing blood vessel analysis of FIG. 4.

At block 402, the blood vessels in unannotated CT images are segmented using the trained neural network yielding a segmentation map. Since the segmentation map may contain false negative regions, which may be referred to as "holes," the segmentation map is processed to close the holes at block 403. After the holes in the segmentation map are closed, the roots or starting points and the endpoints of the segmented blood vessels are automatically detected. The roots may include the arteries origin, the left lung veins origin, and the right lung veins origin. The blood vessel origins are located at the heart. Accordingly, as shown in FIGS. 4 and 5A, at block 404, roots 504 of blood vessels 501 are detected, and at block 406, endpoints 506 of peripheral vessels 502, from which tracking starts, are detected.

Figure 5B:
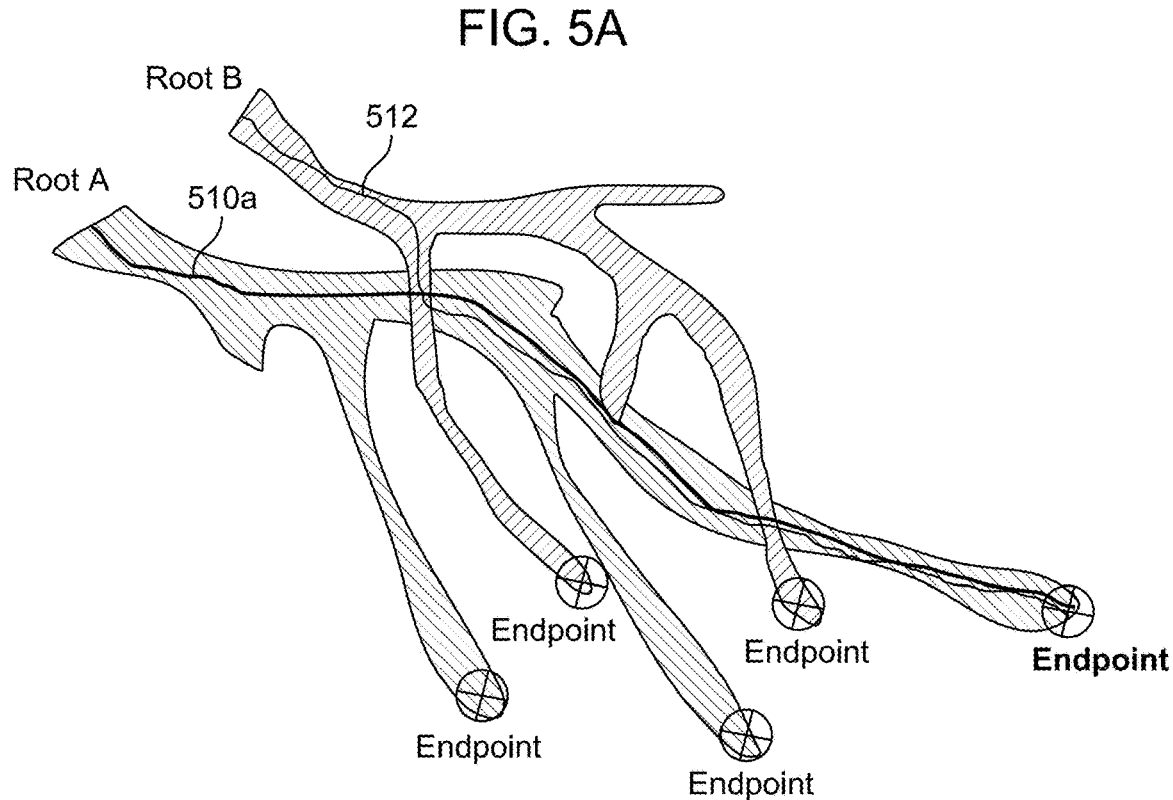

At block 408, the optimal or shortest path, e.g., shortest path 508, from each detected endpoint, e.g., endpoint 506, to each detected root, e.g., root 504, is tracked using an optimal or shortest path algorithm. The shortest path algorithm may be Dijkstra's algorithm. At block 410, the most probable path is selected. For example, the shortest path 510 shown in FIG. 5B has a better score than the shortest path 512 because the path 510a has minimal class alternation. In some aspects, the best root is selected from the possible roots and the class of the path from the best root to the endpoint is selected.

One or more additional steps may be performed to improve performance. For example, any path that contains unlikely curves, e.g., U-turns, may be rejected in advance of performing the shortest path algorithm. As another example, the reconstruction of the paths and the selection of the root may be split into two rounds. In a first round, if, for a given endpoint, there is now a path with high certainty, the given endpoint is left untracked. The certainty of the path may be determined based on relevant factors including topological distance and angles above a threshold. For example, a path with a high topological distance and angles above a threshold may be determined to be a path with high uncertainty. In a second round, after initial blood vessel trees are created from the paths of the first round, the algorithm may revisit previously rejected endpoints and may select the root to which the path does not create significant overlap with vessels of a type opposite the type of the root, e.g., in the case of attempting to connect to the artery root and the path overlaps with a vein.

Figure 5C:
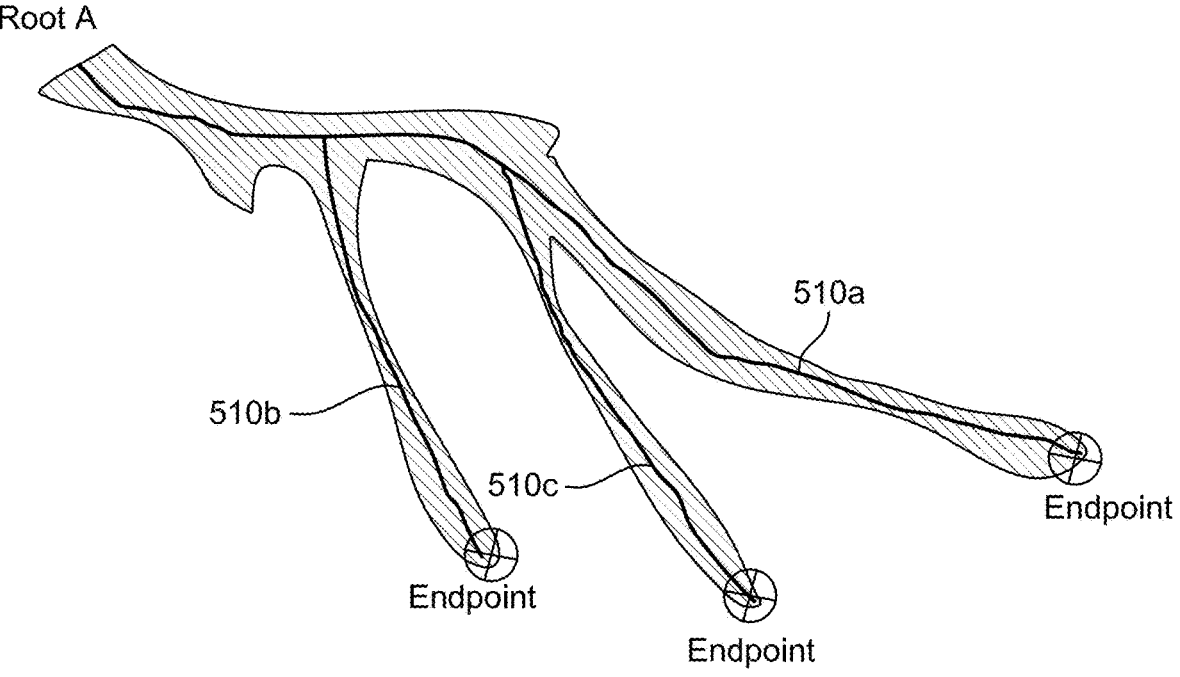

At block 412, the method 400 determines whether there are more endpoints to process. If there are more endpoints to process, blocks 708 and 710 are repeated. If there are no more endpoints to process, the method 700 proceeds to block 414. As shown in FIG. 5C, at block 414, the most probable paths 510a-510c leading to the same root are united or merged into a single directed graph or tree. The process of merging paths into a tree may include estimating the radius along the path. In order to estimate the radius more accurately, a monotonic condition may be incorporated into the estimation of the radius. The monotonic condition may include, as an input, a distance boundary, which may be defined as a volume with a distance from the boundaries of the segmentation such that the volume has a maximum value on the center line.

Figure 26A:
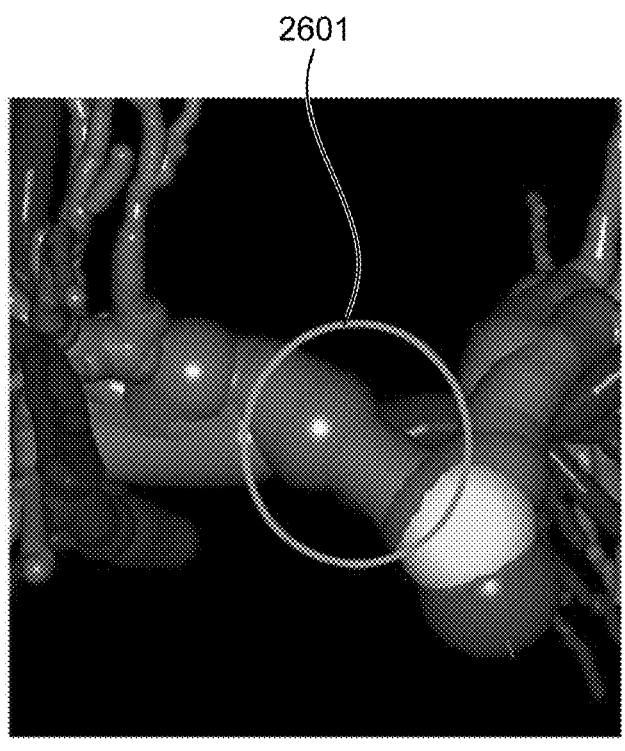
FIG. 26A is a diagram of a portion of a 3D vasculature model that illustrates the results of estimating blood vessel radius without filtering.
Figure 26B:
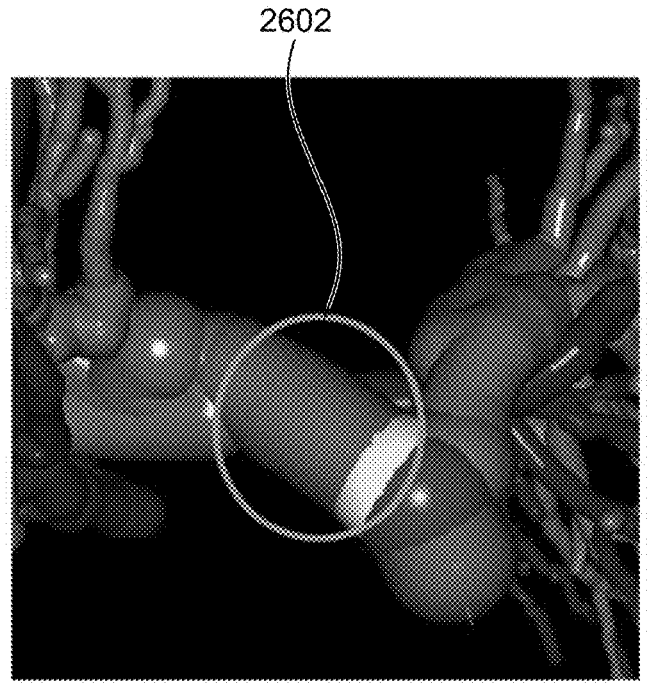
FIG. 26B is a diagram of a portion of a 3D vasculature model that illustrates the results of estimating blood vessel radius with filtering.

For each calculated shortest path, the radius is estimated starting at the endpoint and ending at the root. The distance boundary volume is sampled at the current point yielding a current value. Then, the current radius is set equal to the maximum of the previous radius and the current value such that the current radius is equal or greater than the previous radius and the size of the whole blood vessel only increases from the endpoint to the root. FIG. 26A shows a blood vessel model generated without performing any filtering to account for inaccuracies in an estimated radius of a blood vessel. The portion of the blood vessel highlighted by the circle 2601 shows a narrowing of the blood vessel, which reflects an inaccurate estimate of the radius of the blood vessel. FIG. 26B shows a blood vessel model after filtering the estimated radius of the blood vessel with a monotonic condition to account for inaccuracies in the estimate of the radius of the blood vessel. The portion of the blood vessel highlighted by the circle 2602 reflects a more accurate estimate of the radius of the blood vessel.

Figure 27:
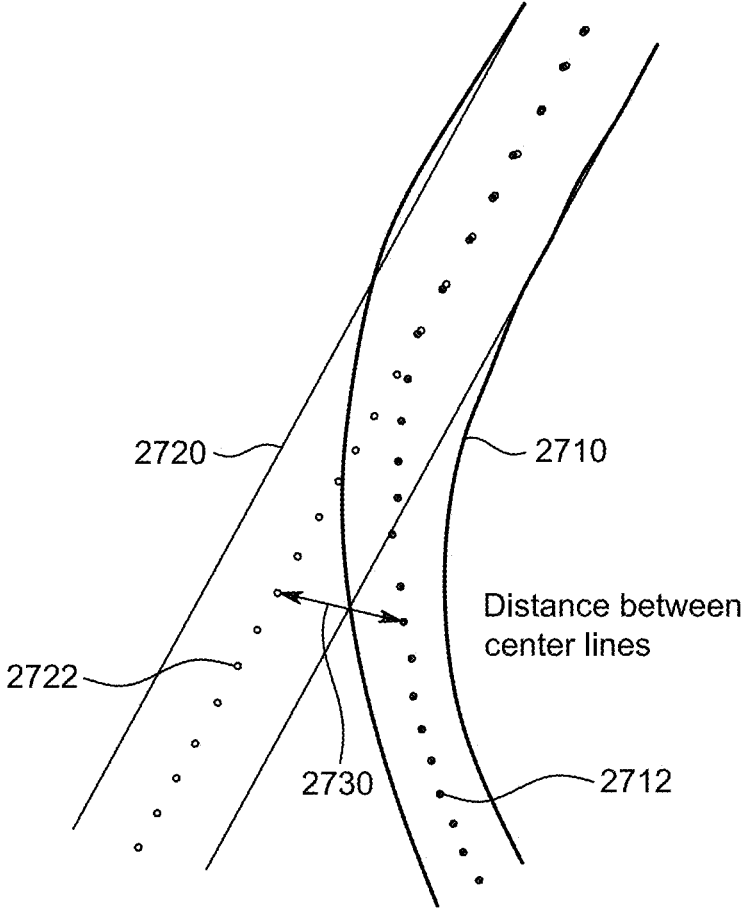
FIG. 27 is a diagram that illustrates the merging of paths into a tree.

FIG. 27 is a diagram that illustrates the merging of paths into a tree according to one aspect of the disclosure. The merging of paths into a tree may include, for each path, determining whether the tree is empty. If the tree is empty, the current path 2710 is treated as the initial tree. If the tree is not empty, the method starts from a root point, goes along the current path 2710, and calculates the distance 2730 between the center line 2712 of the current path 2710 and the center line 2722 of the tree 2720. If the calculated distance 2730 is greater than a threshold, the current path 2710 is split, resulting in a child path.

Before ending at block 418, overlaps between directed graphs are solved at block 416. After overlaps between directed graphs are solved, the directed graphs may be used to create a 3D model. For example, for pulmonary vasculature, the 3D model 604 illustrated in FIG. 6, may be created based on the directed graphs. Thus, the systems and methods of this disclosure may receive as input volumetric images, e.g., CT images 602, and may output a 3D model, e.g., the 3D model 604.

Figure 7A:
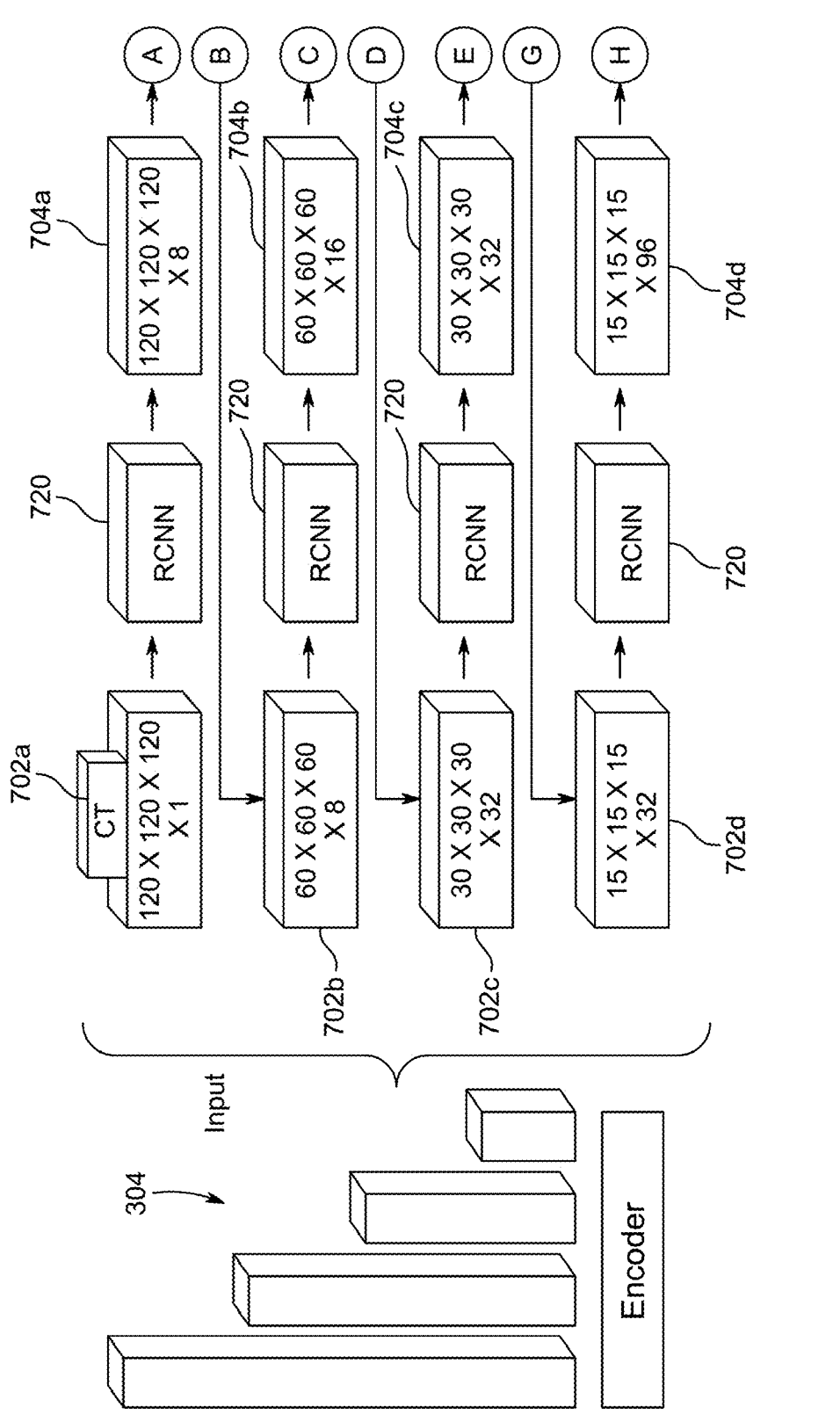
Figure 7A:
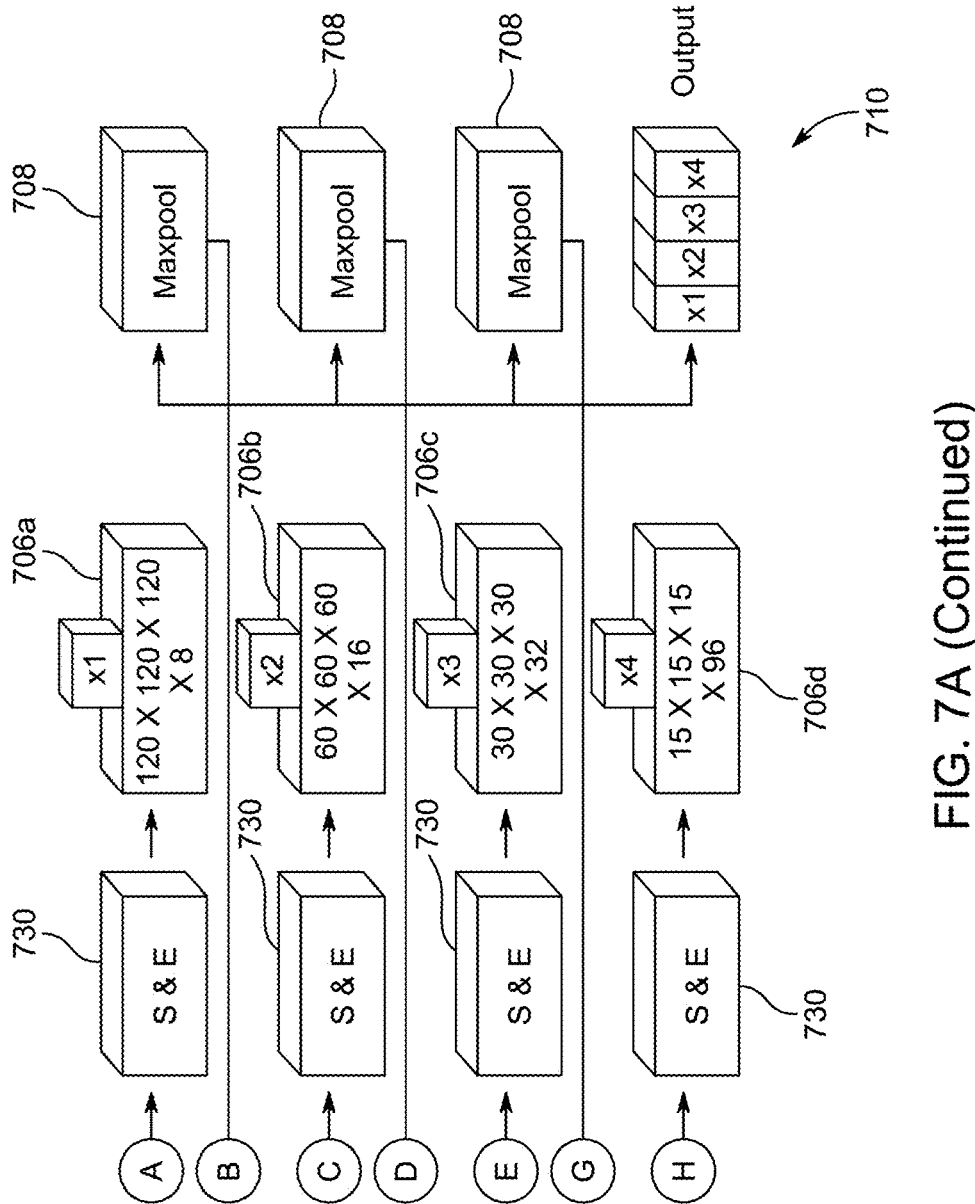

FIGS. 7A and 7B show an example of the encoder 304 of the deep neural network of FIG. 3. As shown in FIG. 7A, CT volume images 702a are input to a recurrent convolutional neural network (RCNN) 720. As illustrated in FIG. 7B, the RCNN 720 may include two recurrent blocks 722. Each recurrent block 722 includes a 3D convolutional block 724, a group normalization block 726, and a rectified linear unit (ReLU) 728 block, the output of which is input to the 3D convolutional block 724.

The RCNN 720 outputs a convolutional block 704a. The convolutional block 704a is then input to a squeeze and excite (S&E) block 730. The S&E block 730 improves the convolutional channel interdependencies of the RCNNs 720 with minimal computational cost. As illustrated in FIG. 7B, the S&E block 730 includes an inception block 731, a global pooling block 732, a first fully connected layer 733, a ReLU block 734, a second fully connected layer 735, a sigmoid activation block 736, and a scale block 737. The global pooling block 732 squeezes each channel of a convolutional block to a single numeric value. The first fully connected layer 733 and the ReLU block 734 adds nonlinearity. The second fully connected layer 735 and the sigmoid activation block 736 gives each channel a smooth gating function. The scale block 737 weights each feature map of the convolutional block based on the results of the processing by the global pooling block 732, the first fully connected layer 733, the ReLU block 734, the second fully connected layer 735, and the sigmoid activation block 736.

The S&E block 730 outputs a convolutional block 706a. The processed convolutional block 706a are then input to a maximum pooling block 708. The maximum pooling block 708 reduces the dimensionality of the convolutional block 706a. The maximum pooling block 708 outputs a convolutional block 702b. The convolutional block 702b is input to an RCNN 720, which outputs a convolutional block 704b. The convolutional block 704b is then input to an S&E block 730, which outputs a convolutional block 706b. The convolutional block 706b is then input to the maximum pooling block 708, which outputs a convolutional block 702c.

The convolutional block 702c is input to a recurrent convolutional neural network 720, which outputs a convolutional block 704c. The convolutional block 704c is then input to an S&E block 730, which outputs a convolutional block 7106c. The convolutional block 706c is then input to a maximum pooling block 708, which outputs a convolutional block 702d. The convolutional block 702d is input to a recurrent convolutional neural network 720, which outputs a convolutional block 704d. The convolutional block 704d is then input to an S&E block 730, which outputs a convolutional block 706d. The convolutional blocks 706a-706d are then assembled (e.g., concatenated) into an output convolutional block 710.

Figure 8A:
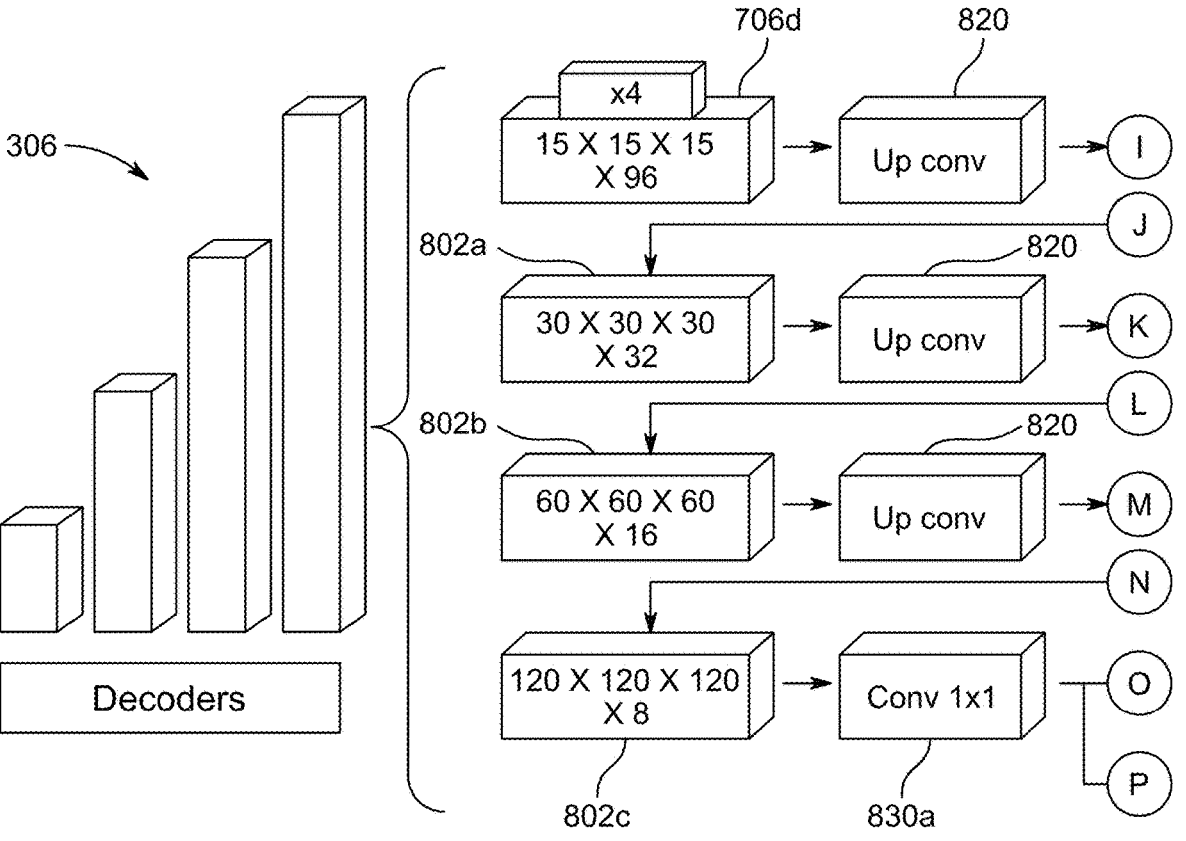
FIGS. 8A-C is a block diagram that illustrates an example of the decoders of the neural network of FIG. 3.
Figure 8A:
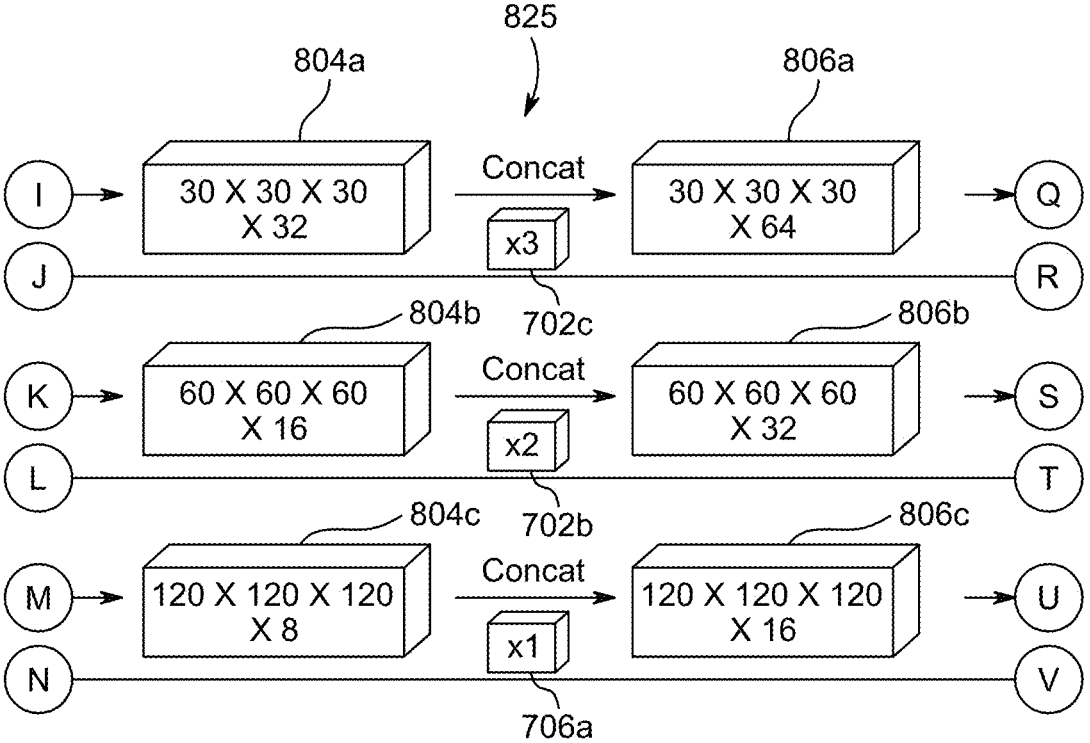
Figure 8B:
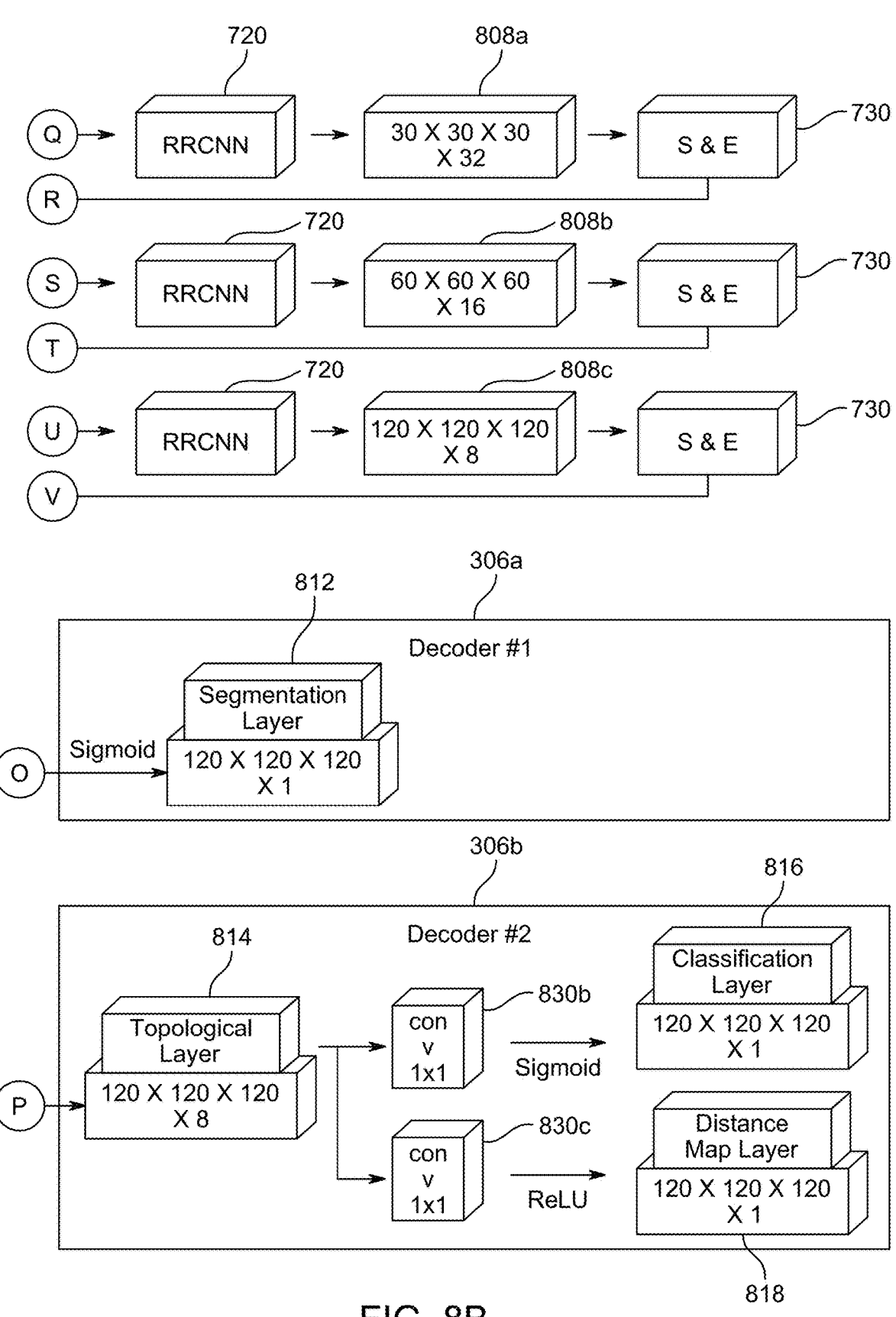
Figure 8C:
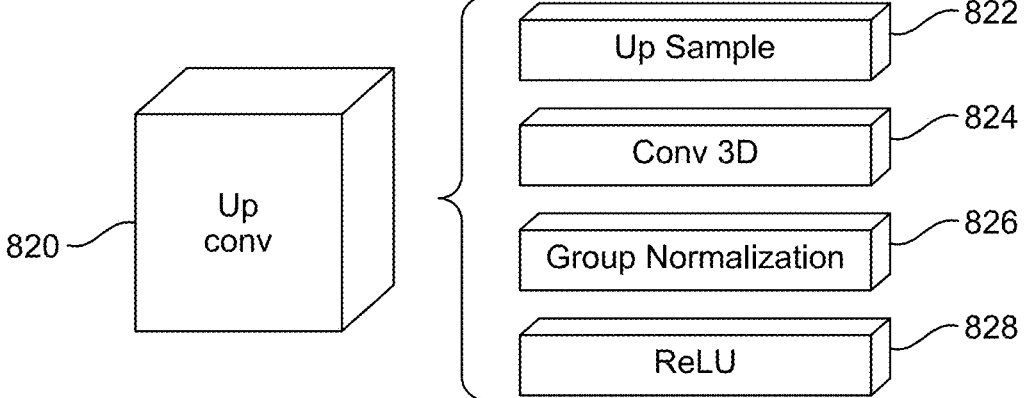

FIGS. 8A-8C show a block diagram that illustrates an example of the decoders 306a, 306b of the deep neural network of FIG. 3. As shown in FIGS. 8A and 8B, the convolutional block 706d shown in FIG. 7A is input to an upconvert block 820, which outputs a convolutional block 804a. The convolutional block 804a is then concatenated 825 with the convolutional block 702c shown in FIG. 7A, yielding a convolutional block 806a. The convolutional block 806a is input to an RCNN 720, which outputs a convolutional block 808a. The convolutional block 808a is then input to an S&E block 730, which outputs a convolutional block 802a.

The convolutional block 802a is input to an upconvert block 820, which outputs a convolutional block 804b. The convolutional block 804b is then concatenated 825 with the convolutional block 702b shown in FIG. 7A, yielding a convolutional block 806b. The convolutional block 806b is input to an RCNN 720, which outputs a convolutional block 808b. The convolutional block 808b is then input to an S&E block 730, which outputs a convolutional block 802b.

The convolutional block 802b is input to an upconvert block 820, which outputs a convolutional block 804c. The convolutional block 804c is then concatenated 825 with the convolutional block 706a shown in FIG. 7A, yielding a convolutional block 806c. The convolutional block 806c is input to an RCNN 720, which outputs a convolutional block 808c. The convolutional block 808c is then input to an S&E block 730, which outputs a convolutional block 802c. The convolutional block 802c is input to a convolution block 830a.

As shown in FIG. 8B, the first decoder 306a includes the convolution block 830a shown in FIG. 8A and a sigmoid function, which output the segmentation layer 812. The second decoder 306b includes two convolution blocks 830b, 830c, which receive as input the output from the convolution block 830a shown in FIG. 8A. The second decoder 306b extracts the sigmoid portion of the output from the convolutional block 830b, yielding the classification layer 816. The second decoder 306b extracts the ReLU portion of the output from the convolution block 830c, yielding the distance map layer 818. As shown in FIG. 8C, the upconverter block 820 may include an up sample block 822, a 3D convolution block 824, a group normalization block 826, and a ReLU block 828.

The deep neural network may be based on a U-Net style architecture with per voxel outputs. The deep neural network may include an input that receives 3D volume images, e.g., CT volume images, and multiple outputs that provide segmentation probability, classification probability, e.g., artery probability, and a topological embedding vector. The topological embedding vector uses blood vessel connectivity information to improve accuracy. The deep neural network may utilize a large patch size, which improves accuracy in the mediastinum region because of the large context and enables the deep neural network to use connectivity information in a large volume.

Figure 9A:
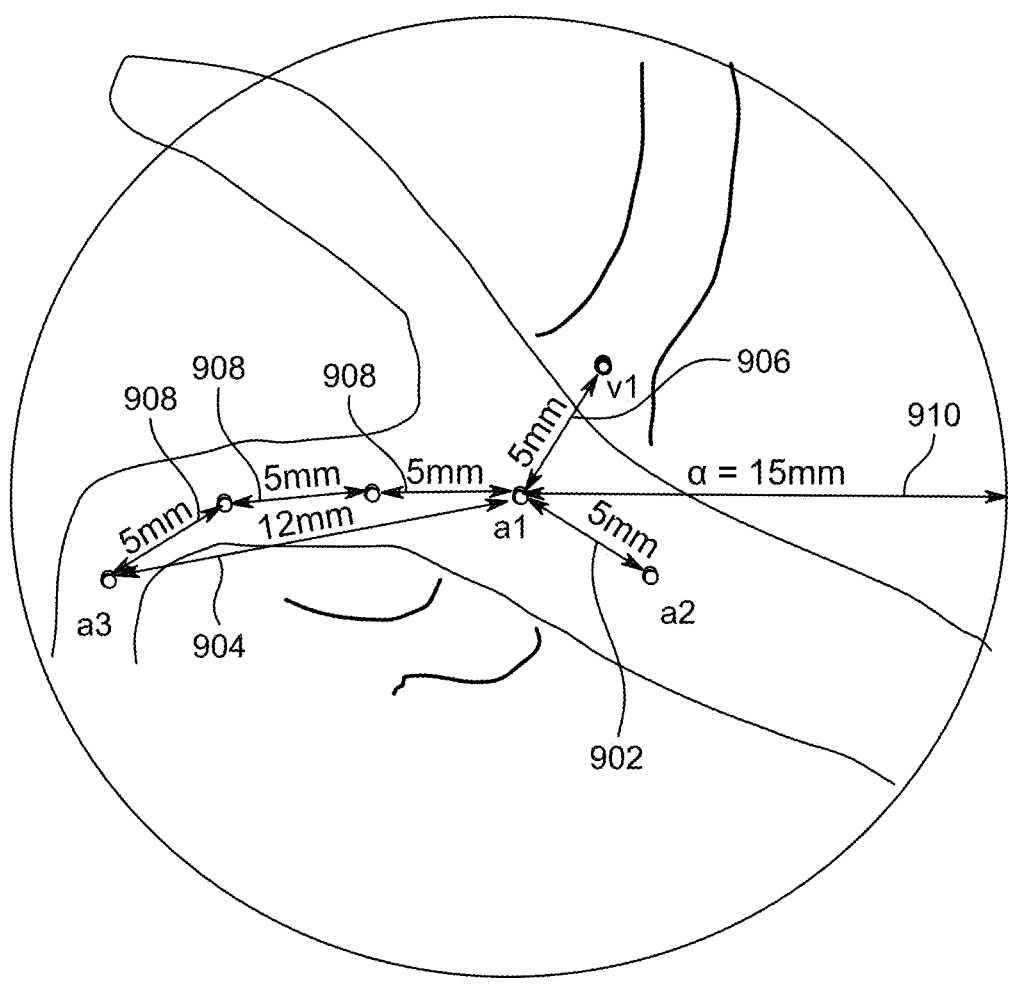
FIGS. 9A and 9B are schematic diagrams that illustrate topological embedding, which may be performed by the neural network of FIG. 3.
Figure 9B:
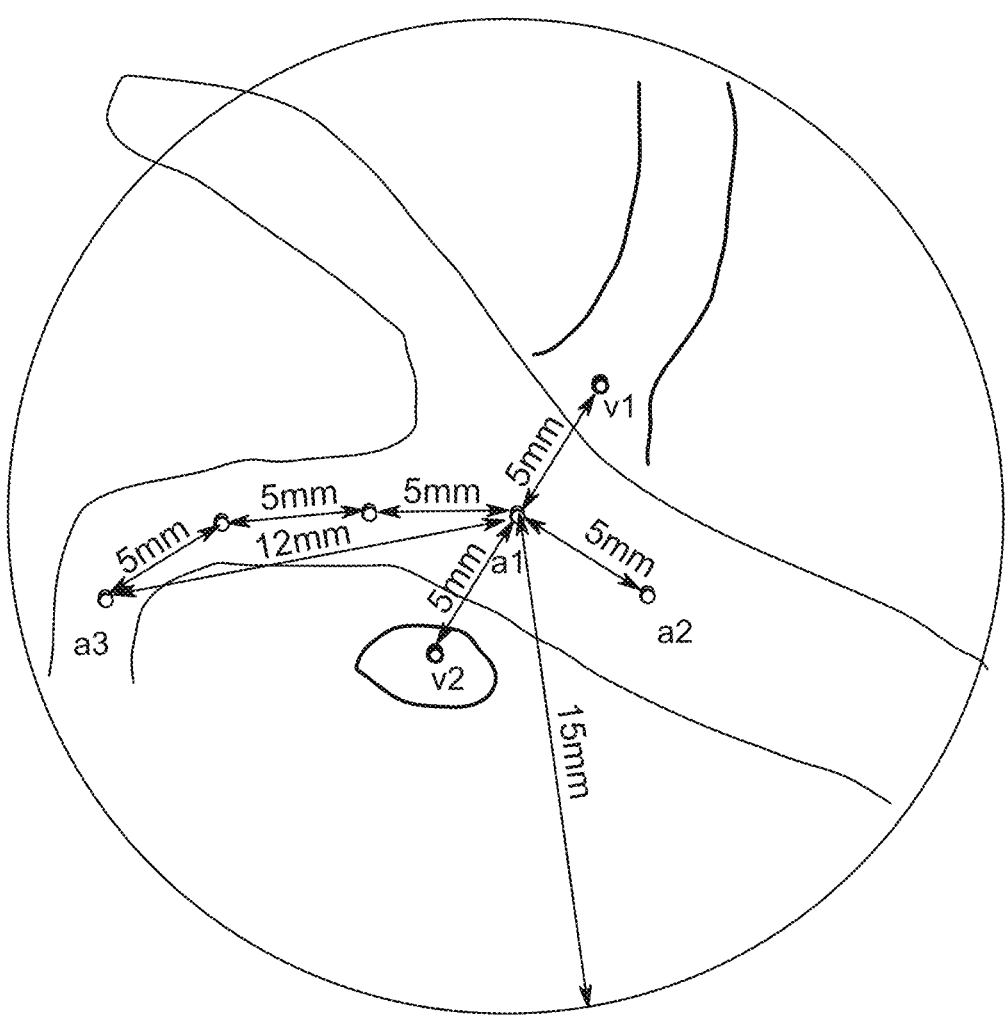

The deep neural network outputs a topological embedding vector for each voxel. The deep neural network is trained to match the Euclidian distance of topological embedding vectors to corresponding topological distances. For example, as shown in FIGS. 9A and 9B, the Euclidian distances (D) are: D(a1, a2)=5 mm (902), D(a1, a3)=12 mm (904), and D(a1, v1)=5 mm (906); and the topological distances (T) are: T(a1, a2)=5 mm (902), T(a1, a3)=15 mm (908), and T(a1, v1)=∞. The deep neural network may be trained to match the Euclidian distance of topological embedding vectors to corresponding topological distances as follows: ‖Net(a1)−Net(a3)‖≈15 mm and ‖Net(α1)−Net(v1)‖→∞. In one implementation, loss terms may be added in the training of the deep neural network to correlate classification differences with topological distances.

The topological loss 322 of the neural network of FIG. 3 may be used to increase the class distance in the feature space. The topological loss 322 may be determined according to the following example of topological loss calculations. In an example, D(x1, x2)=T(x1, x2), where $x_i$ is the network topological layer value in point pi. Thus, D(x(a1), x(a2))=15 mm and D(x(a1), x(v1))→∞ for each pair p1, p2 where D(p1, p2)<α(910). The topographical loss associated with each pair of skeleton points p1, p2 in a patch may computed according to the following equation:

$$Topo(p_1, p_2) =$$

$$\begin{cases} \text{Smooth}_{L1}\left(\|x_1 - x_2\| - \dfrac{T(p_1, p_2)}{\alpha}\right) & \text{where } p_1, p_2 \text{ are in the same class} \\ \dfrac{1}{K} * \max(0, [K - \|x_1 - x_2\|]) & \text{otherwise} \end{cases}$$

The total topological loss may then be computed according to the following equation:

$$L = \frac{1}{n}\sum Topo(p_1, p_2)$$

where n is the total number of pairs and K is a constant which, for example, may be equal to or greater than 3 (3 times the maximum value of the topological loss). In other aspects, K may be any constant value suitable for acting as an infinity measure, i.e., a number which is too large to be a topological loss. For example, K may be 4 or 5. Increasing the constant K increases the distance in the feature space between arteries and veins.

Figure 10:
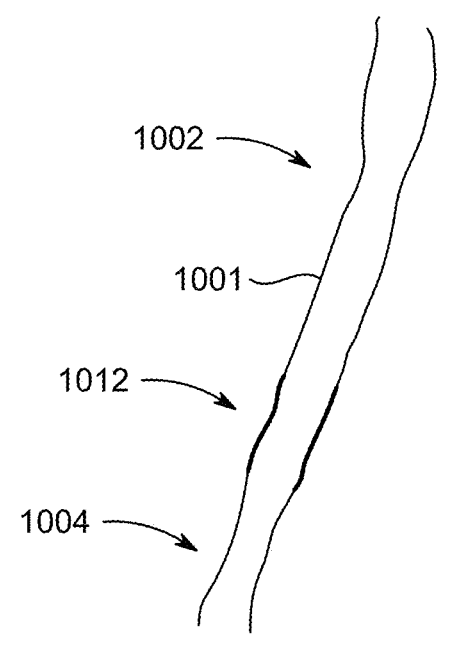
FIGS. 10 and 11 are schematic diagrams that illustrate challenges addresses by aspects of the disclosure.

In some cases, there may be a classification inconsistency, in which one portion of a blood vessel is classified as a vein and another portion of the same blood vessel is classified as an artery. For example, as illustrated in FIG. 10, first and second portions 1002, 1004 of a blood vessel 1001 may be classified as a vein, whereas a third portion 1012 of the blood vessel 1001 between the first and second portions 1002, 104 of the blood vessel 1001 may be classified as an artery.

To increase classification consistency along blood vessels, an unsupervised "smooth" loss, such as the smooth L1 loss 332, may be applied to the distance map layer 330. The smooth L1 loss 332 may be determined according to the following example of smooth L1 loss calculations. $S_p$ may be defined as the result of the network segmentation layer for point p, $M_p$ may be defined as the result of the network distance map layer for point p, $C_p$ may be defined as the result of the network classification layer for point p, $T(p_1, p_2)$ may be defined as the result of the network topological distance between points p1 and p2, and $D(p_1, p_2)$ may be defined as the Euclidian distance between points $p_1$ and $p_2$. For each pair of points $(p_1, p_2)$ in a training patch, the following examples of conditions may be imposed:

$S_{p1}{>}0.5, S_{p2}{>}0.5$ (segmentation voxel), $M_{p1}{<}\sqrt{3}, M_{p2}{<}\sqrt{3}$ (on or near the skeleton), $D(p_1,p_2){<}3$ ($p_1$ is near $p_2$), and $$T(p_1, p_2) < \frac{3}{\alpha} = \frac{3}{15} = 0.2$$

(same classification value according to the topological embedding layer).

In aspects, the threshold values for the conditions above may be other threshold values suitable for obtaining accurate classification results for given volumetric image data. The total smooth L1 loss may then be computed according to the following equation:

$$L = \frac{1}{n}\sum (1 - T(p_1, p_2))^2 * MSE(C_{p1}, C_{p2}),$$

where n is the total number of pairs of points $p_1$, $p_2$ and MSE is the mean squared error.

Figure 11:
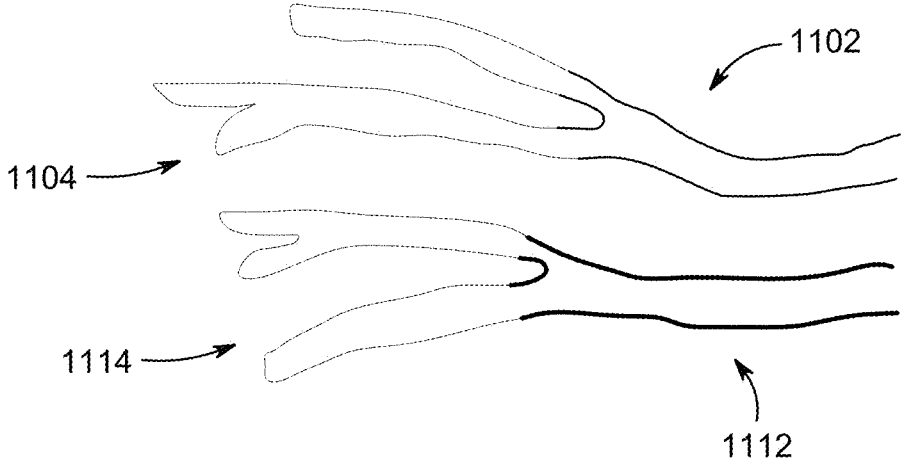

In some cases, there may be unsupervised extraction of "Don't Care" regions. Manual user annotations may not extend to the full extent of the blood vessel. For example, as illustrated in FIG. 11, a vein and an artery may continue beyond an annotated portion 1102 of the vein and an annotated portion 1112 of the artery, respectively, leaving an unannotated portion 1104 of the vein and an unannotated portion 1114 of the artery. Also, the deep neural network may correctly classify some voxels as blood vessels, but this may have a negative impact on the training of the deep neural network. One solution to these issues may be to use a pre-trained segmentation model of peripheral blood vessels. Another solution may be to weight the segmentation dice loss term. For example, the weighted dice loss may be calculated according to the following expression:

$$L = \frac{2\sum_i^N w_i p_i g_i}{\sum_i^N w_i (p_i^2 + g_i^2)}$$

where $p_i$ are the predicted values, $g_i$ are the ground truth, $w_i=0$ for unannotated peripheral blood vessels (e.g., 1104, 1114 of FIG. 11), and $w_i=1$ otherwise.

Figure 12:
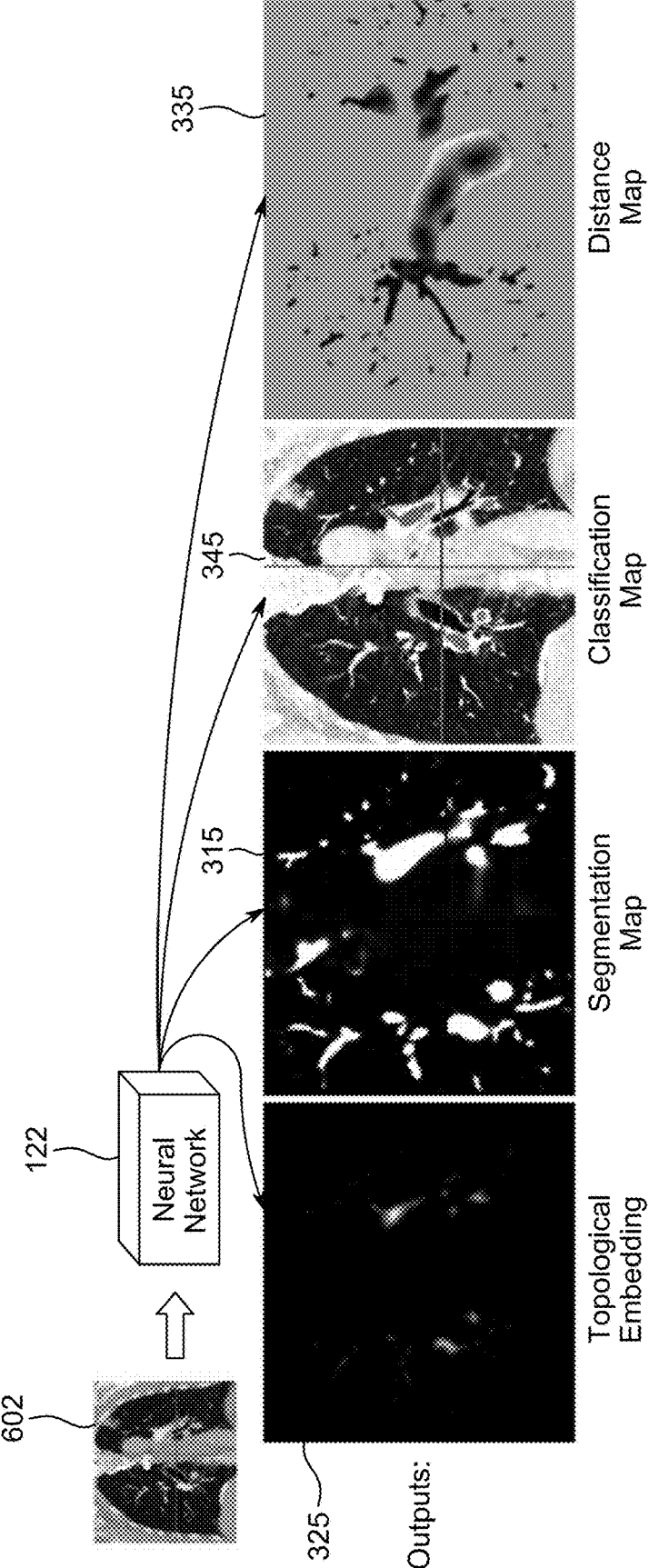
FIG. 12 is a diagram that illustrates examples of the outputs of the neural network of FIG. 3.

Referring to FIG. 12, the deep neural network 122 may be supervised, which means that the deep neural network 122 is optimized based on a training set of examples. During actual use the input to the deep neural network 122 are CT images 602 and the outputs from the deep neural network 122 are volumetric data, which includes, in order of output, topological embedding vector 325, a segmentation map 315, a classification map 345, and a distance map 335. During training, ground truth information is used to evaluate the outputs from the deep neural network 122 and update the weights of the deep neural network 122 based on the evaluation. The evaluation uses losses as metrics. The losses may include one or more of the following losses: topological loss, consistency loss, dice loss, cross-entropy loss, and smooth L1 loss.

The deep neural network's quality may depend on the availability of large, annotated data sets. The peripheral information improves accuracy because of the blood vessel connectivity information. However, the number of branches may increase exponentially. Thus, the systems and methods of this disclosure may provide efficient annotation tools to segment and classify blood vessel branches in medical image data sets, e.g., 3D medical image data sets. The annotation tools may be manual and/or semi-automatic tools. The annotation tools may include a pretrained neural network that segments the blood vessels, and a shortest path algorithm that creates blood vessels between two points, e.g., a root and an endpoint, which are manually selected by the user, e.g., a clinician with experience in reading medical images. This leads to accurate segmentation of the blood vessels and annotation of anatomical trees.

Separate trees may be generated for each blood vessel that enters or exits the heart. Each tree model may be decomposed into a set of cylinder-shaped segments. An oblique view is displayed, where the radius is marked accurately. The segment's cylinder is then added to a tree and displayed to a user. After manually and/or semi-automatically segmenting the blood vessels, a 3D model of the vasculature, e.g., the vasculature of the lungs, may be updated. The annotated 3D medical image data set may then be used to train the neural network of this disclosure to automatically segment and classify other 3D medical image data sets.

In aspects, the accuracy of the neural network may be evaluated by comparing the results of the neural network to the annotated 3D models. The accuracy criteria for the evaluation method may be based on centerline points. A hit may refer to a ground-truth centerline inside the methods' segmentation. A correct classification may refer to the method assigning the artery or vein label correctly. And a total correct may refer to an instance where there is both a hit and a correct classification. There may be an instance in which there is a miss and an example of an instance in which there is an incorrect classification. In one example evaluation, the neural network accuracy was evaluated at different depths of the blood vessel trees to obtain the follow results:

Up to lobar vessels: 99.2% hit, 98.5% total correct;
Lobar+5 cm: 99.5% hit, 97% total correct; and
Entire model: 99.5% hit, 96% total correct.

In an example of an evaluation, with respect to segmentation in one CT slice, all blood vessels are detected in the central region and in the periphery, and there are no false positives in the mediastinum due to the aorta or vena-cava. With respect to classification for the same CT slice, there is good overlap between the ground-truth voxels and the segmented artery and vein voxels. For the same CT slice, there are accurate borders even in areas where different blood vessels are touching, without clear borders in the CT slice. In the example evaluation, the neural network errors include: a classification error in another CT slice, in which there is a change from artery to vein along the blood vessel; a segmentation hole in still another CT slice; and ~97% of the voxels are accurate. The remaining blood vessel analysis may be designed to be robust to these errors so that branches are not cut off from the 3D model.

In a second phase of the methods of this disclosure, the roots are detected in segmented blood vessels. FIG. 13 is a flowchart of a method for automatically detecting roots of arteries. At block 1302, a binary volume with artery segmentation, a distance boundary volume, and a lung mask are received. The distance boundary volume is a volume with a distance from the boundaries of the segmentation such that the volume has a maximum value on center line. The lung mask is a binary volume that is true on each voxel that is inside the lungs. At block 1304, blood vessels are classified as arteries. At block 1306, the skeleton is calculated from the artery classification. At block 1308, a graph of arteries is created.

Figure 14:
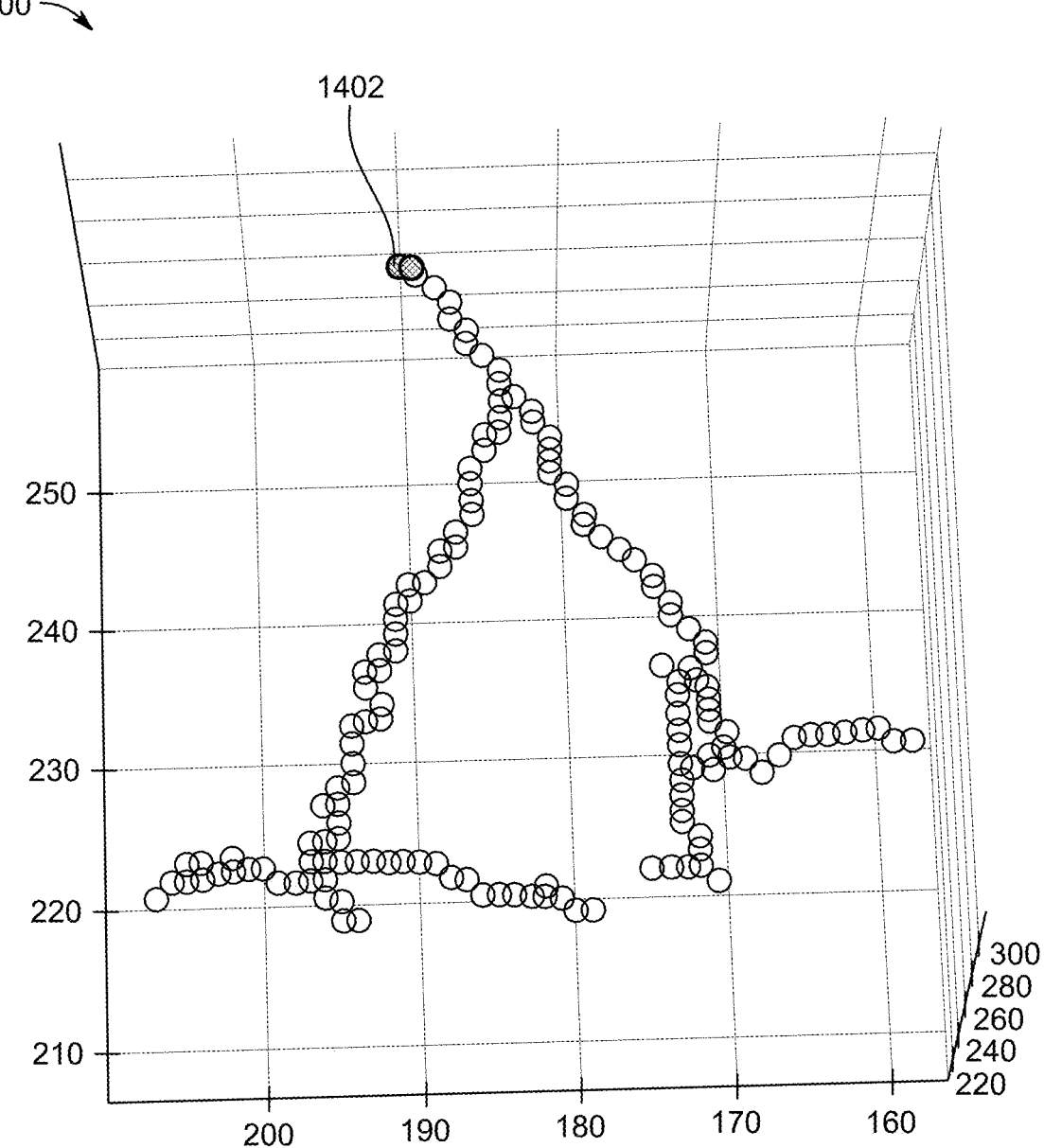
FIG. 14 is a three-dimensional graph that illustrates a result of automatic root detection.
Figure 15A:
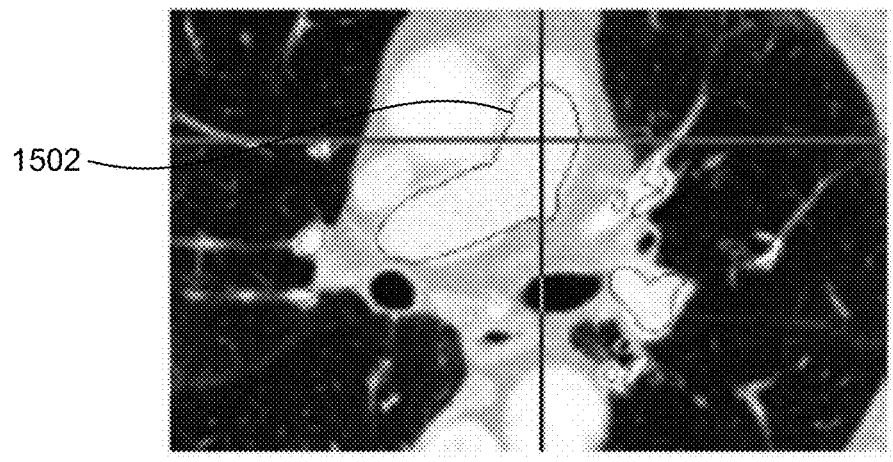
FIGS. 15A-15C are computed tomography (CT) images that illustrate automatic root detection for arteries.
Figure 15B:
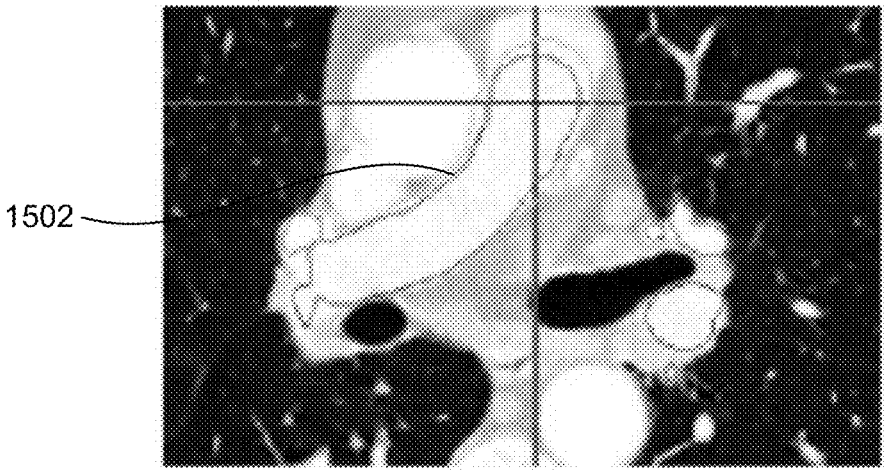
Figure 15C:
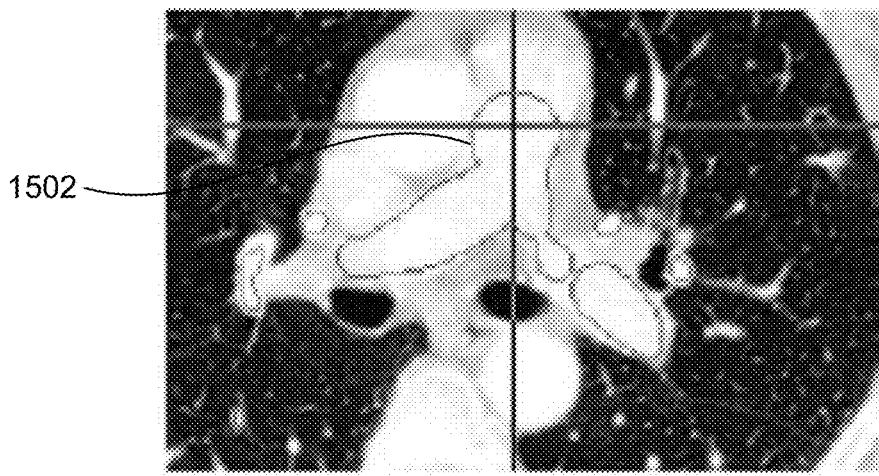

FIG. 14 shows an example of a graph of arteries 1400. The graph of arteries 1400 may be created using a suitable software library. At block 1310, endpoints are extracted from the graph of arteries 1400. Endpoints may be identified as voxels which have only one neighbor. At block 1312, the endpoints which are outside of the lung mask are filtered. At block 1314, the distance boundary is sampled in the coordinates of the endpoints, and, at block 1316, the sampled distance boundary which has a radius lower than a threshold is filtered. Then, at block 1318, the endpoint that has longest path to the nearest bifurcation is selected as a root of the arteries, e.g., the endpoint 1402. In some aspects, the most anterior point of the artery is selected as the root. FIGS. 15A-15C show examples of CT images in which artery roots 1502 are detected.

Figure 16:
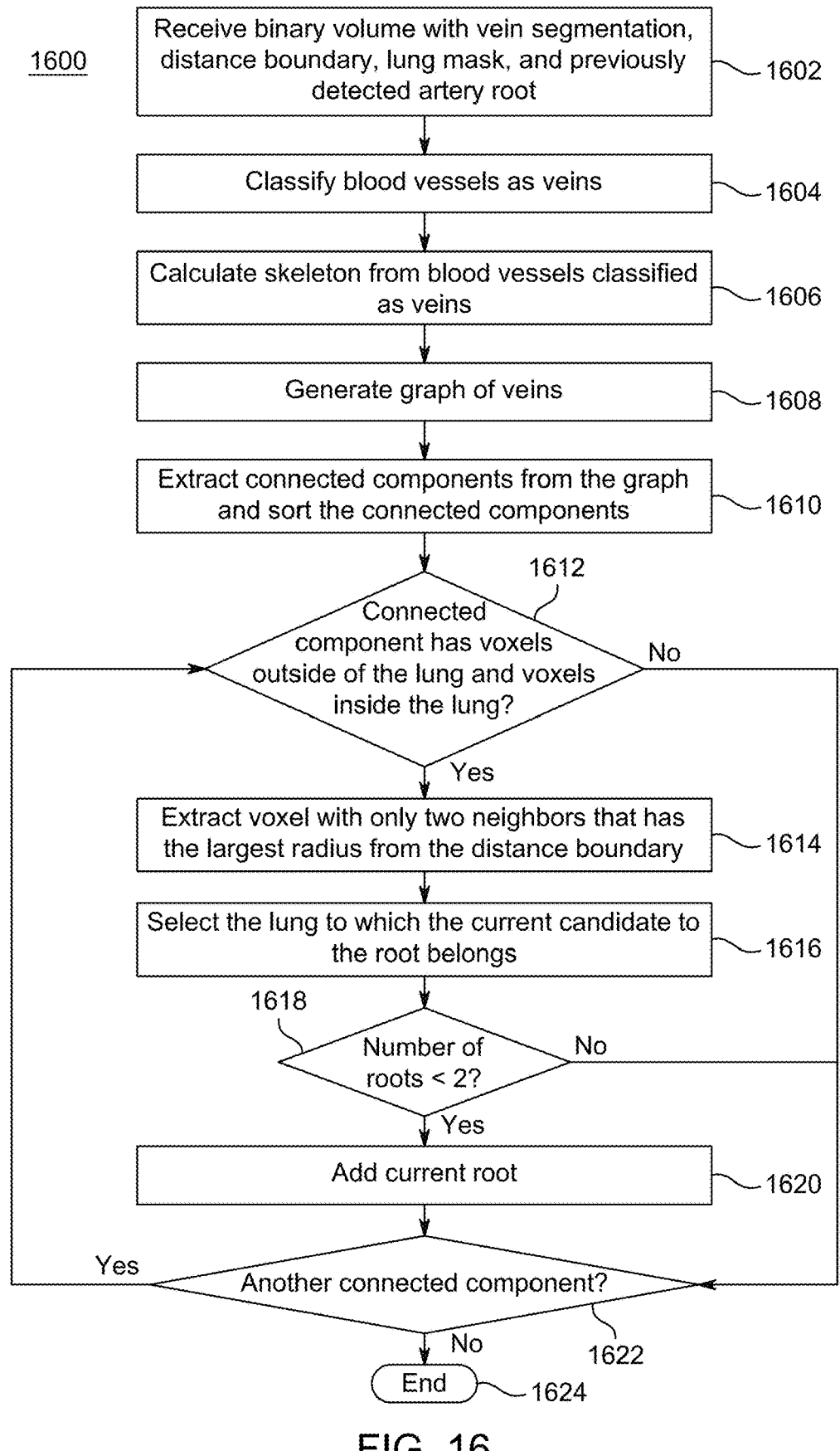
FIG. 16 is a flowchart that illustrates a method of detecting roots for veins.
Figure 17A:
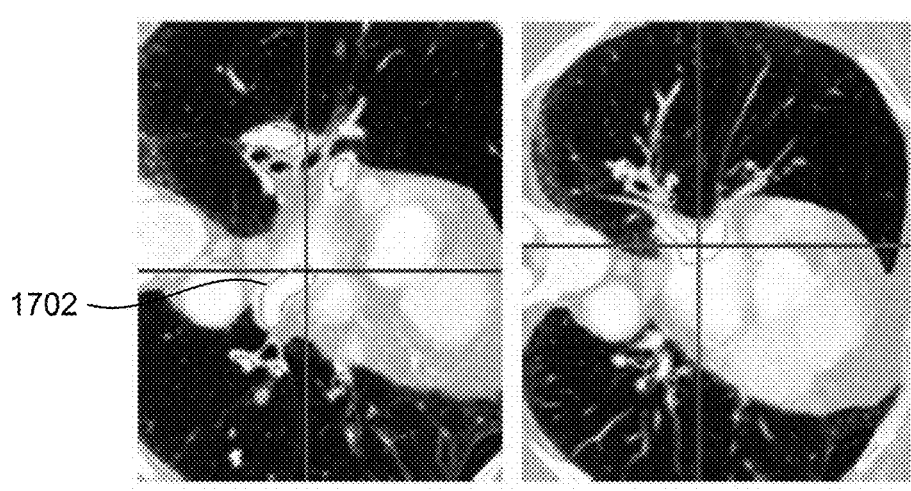
FIGS. 17A-17C are CT images that illustrate automatic root detection for veins.
Figure 17B:
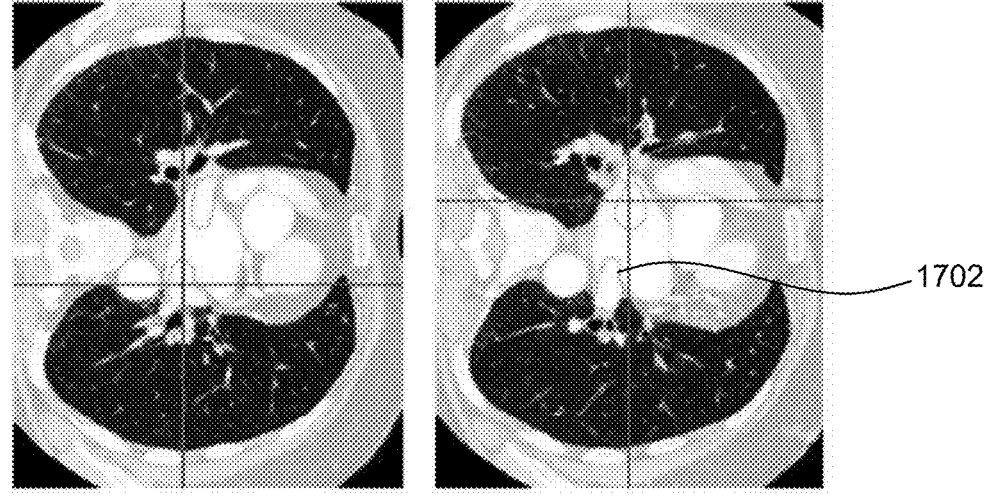
Figure 17C:
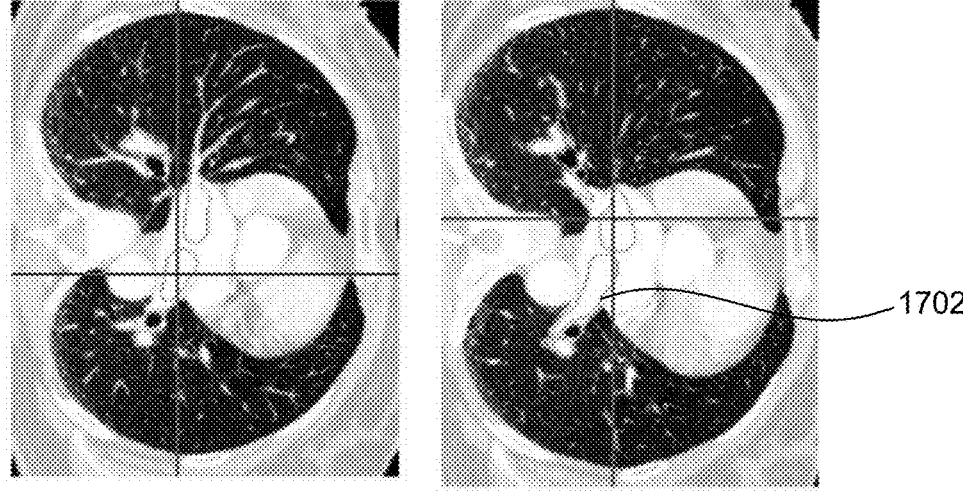

FIG. 16 is a flowchart of a method for automatically detecting roots of veins. At block 1602, the binary volume with artery segmentation, the distance boundary volume, the lung mask, and an artery root that was detected previously is received. The method of FIG. 16 assumes that the maximum number of vein roots for each lung is two. At block 1604, blood vessels are classified as veins. At block 1606, a skeleton is calculated from the blood vessels classified as veins. At block 1608, a graph of veins is created. The graph of veins may be created using a suitable network software library. At block 1610, connected components are extracted from the graph and sorted. Then, for each connected component, blocks 1612-1618 are performed. Blocks 1612-1618 may be performed on connected components in order starting with the largest connected component and ending with the smallest connected component.

At block 1612, the method 1600 determines whether a connected component has voxels that are outside of the lung and voxels that are inside the lung. If a connected component has voxels that are outside of the lung and voxels that are inside the lung, a voxel with only two neighbors that has a largest radius from the distance boundary is extracted at block 1614. At block 1616, the lung to which the current candidate to the root belongs is determined. At block 1618, the method 1600 determines whether the number of roots for the determined lung is less than 2. If the number of roots for the determined lung is less than 2, the current root is added at block 1620. Then, at block 1622, the method 1600 determines whether there is another connected component to be processed. If there is another connected component to be processed, the method 1600 returns to block 1612. Otherwise, the method 1600 ends at block 1624.

As described herein, the blood vessel segmentation of the medical images may include "holes." In aspects, methods, including, for example, the methods illustrated in FIGS. 18A-25C, may be employed to close or fill holes in the segmentation of blood vessels. If the holes are not closed, possible errors include missing blood vessels and incorrect labeling during graph creation. These errors may lead to negative effects on the user and patient. For example, since the 3D model may be used for surgery planning, if the 3D model is missing a vessel, the clinician may not be aware of the missing vessel during surgery and cut through the missing vessel, which may lead to significant bleeding.

Figure 18A:
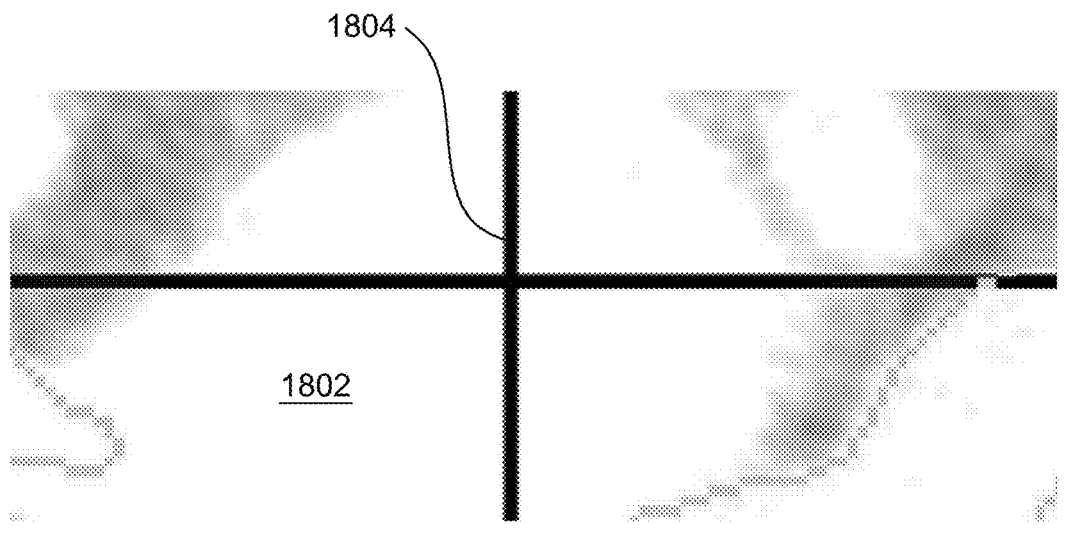
Figures 18B, 18C, 18D:
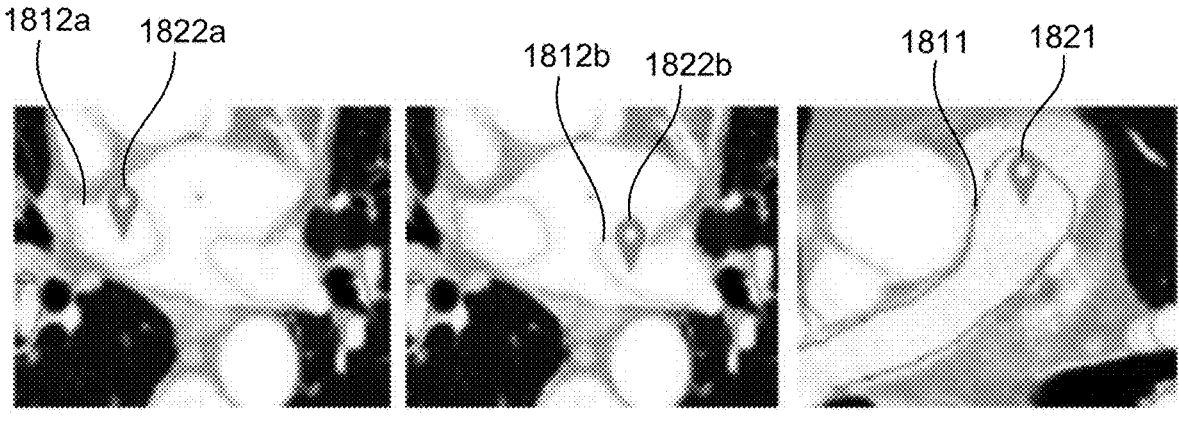

In one aspect, a method of closing holes may include roughly finding a center point 1804 of the heart 1802, as illustrated in FIG. 18A. This may be accomplished, for example, by averaging the positions of all the roots for arteries and veins. As illustrated in FIGS. 18B-18D, the root positions 1822a and 1822b of veins 1812a and 1812b, and the root position 1821 of artery 1811 are averaged to find the center point 1804 of the heart 1802. The method of closing holes may also include roughly finding left and right hilum center points. FIG. 19A illustrates the center point 1902a of the right hilum. For example, as illustrated in FIGS. 19B-19D, this may be performed by finding the intersection points x, y, z 1915 of the lung mask with a line 1912 such that y, z are a predetermined distance (e.g., ±40 mm) 1914 from the heart 1901 and the maximum segmentation voxels are on the x-axis.

Figure 20A:
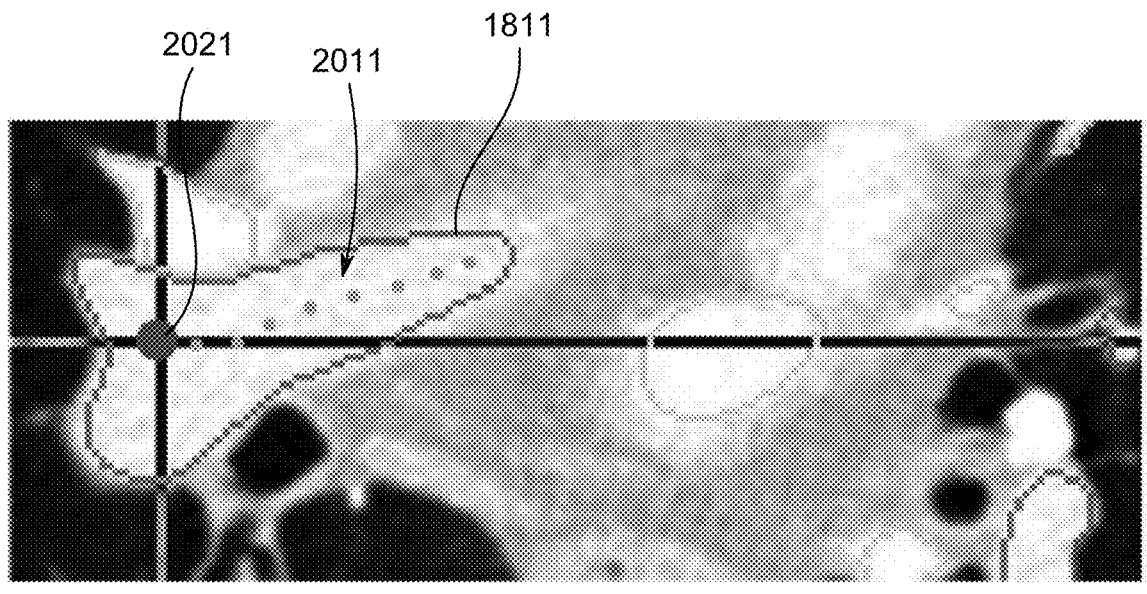

The method of closing holes may also include finding the artery and vein skeleton points closest to the hilum. Finding the artery and vein skeleton points may include creating a skeleton for the largest components connected to the hilum of each class (e.g., artery and vein) and finding the skeleton point closest to the hilum for each class such that the radius of the closest skeleton point is roughly half the radius of the root. For example, as illustrated in FIG. 20A, a skeleton 2011 is created for the largest connected components of the artery 1811 and the skeleton point 2021 closest to the hilum for the artery 1811 is found such that the radius of the closest skeleton point is roughly half the radius of the root. In a similar way, a vein skeleton point may be found.

Figure 20B:
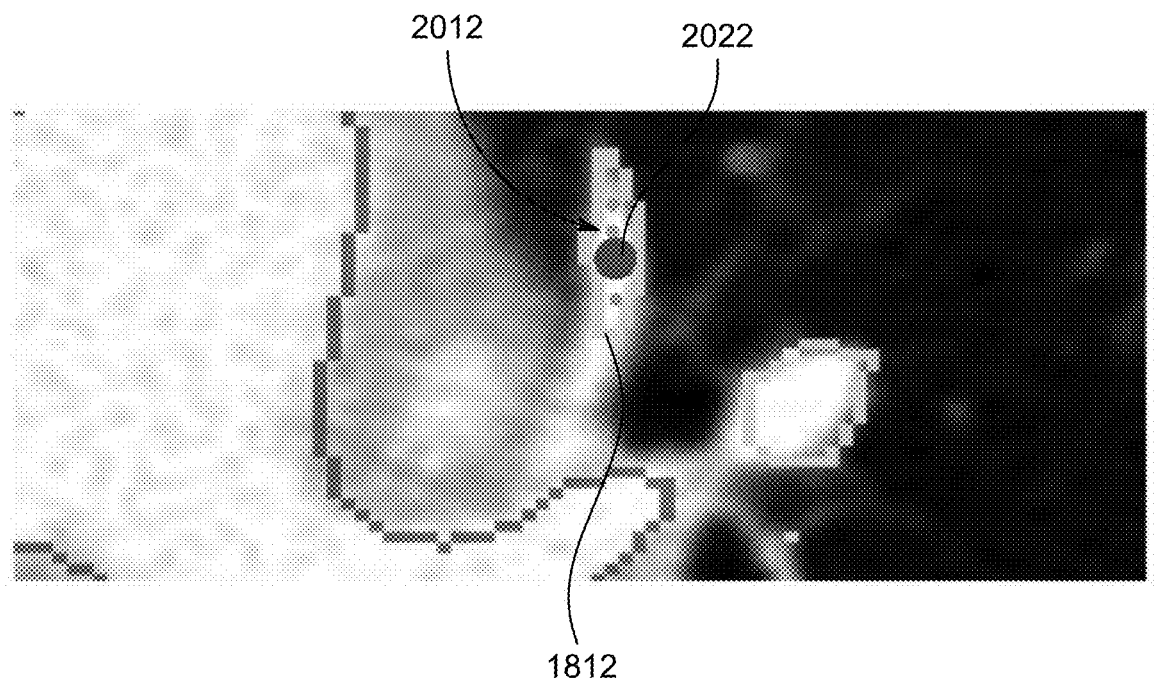

The method of closing holes may also include finding candidate points for "holes." Finding candidate points for "holes" may include, for each largest connected components of each class that is not connected to the largest connected component of the class of each largest connected component, creating a skeleton and selecting a skeleton point that is closest to the hilum center point if the radius of the skeleton point is greater than a threshold, which may be predetermined. For example, as illustrated in FIG. 20B, a skeleton 2012 is created for a large connected component of the vein 1812 that is not connected to the largest connected component of a vein. Next, the skeleton point 2022, which is closest to the hilum center point and which has a radius greater than a threshold, is selected.

The method of closing holes may also include finding an optimal path from a hole to an existing segmentation. Finding an optimal path from a hole to an existing segmentation may include executing a Dijkstra algorithm from a candidate point 2102 to the closest hilum skeleton point of the same class. The Dijkstra algorithm may be performed according to one or more of the following conditions:

1. Give preference to the center line of an existing same class segmentation;
2. Allow the algorithm to go over "white" voxels if it saves ×3 distance;
3. Allow the algorithm to go over the segmentation of the opposite class if it saves ×6 distance; and
4. Stop when the algorithm reaches any type of existing segmentation.

Figure 21A:
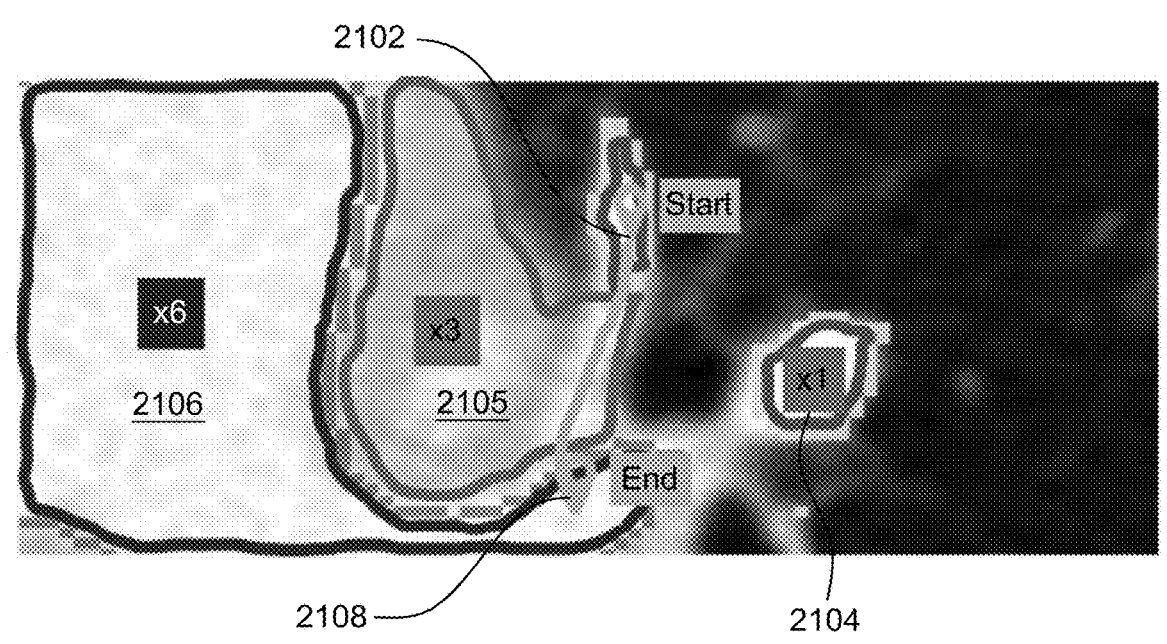
Figure 21B:
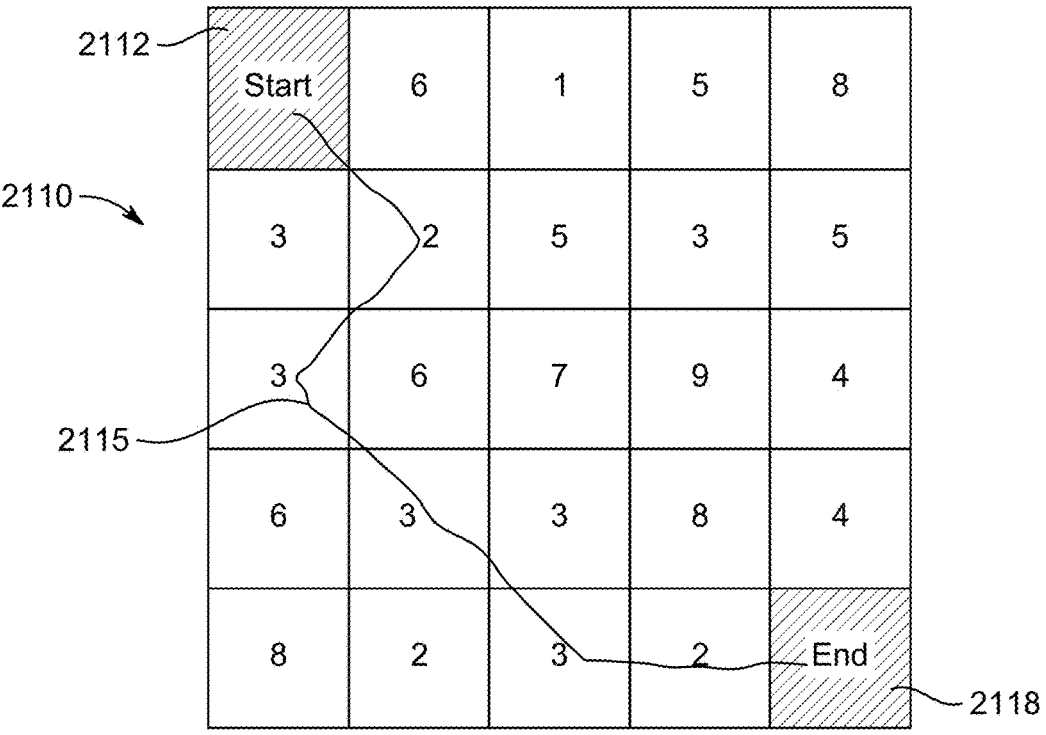

For example, as illustrated in FIG. 21A, a Dijkstra algorithm is performed from a candidate point 2102 to the closest hilum skeleton point 2108 of the same class. While there is an existing same class segmentation, i.e., segmented vein 2104, the algorithm goes over the "white" voxels 2105 because this saves ×3 distance and the algorithm goes over the segmentation of the opposite class, i.e., segmented artery 2106. The algorithm stops at the existing segmented artery 2106. FIG. 21B illustrates an example of an adjacency matrix 2110 for a Dijkstra algorithm showing a shortest path 2115 from a starting candidate point 2112 to an ending point 2118, e.g., a closest hilum skeleton point 2108.

Figure 22:
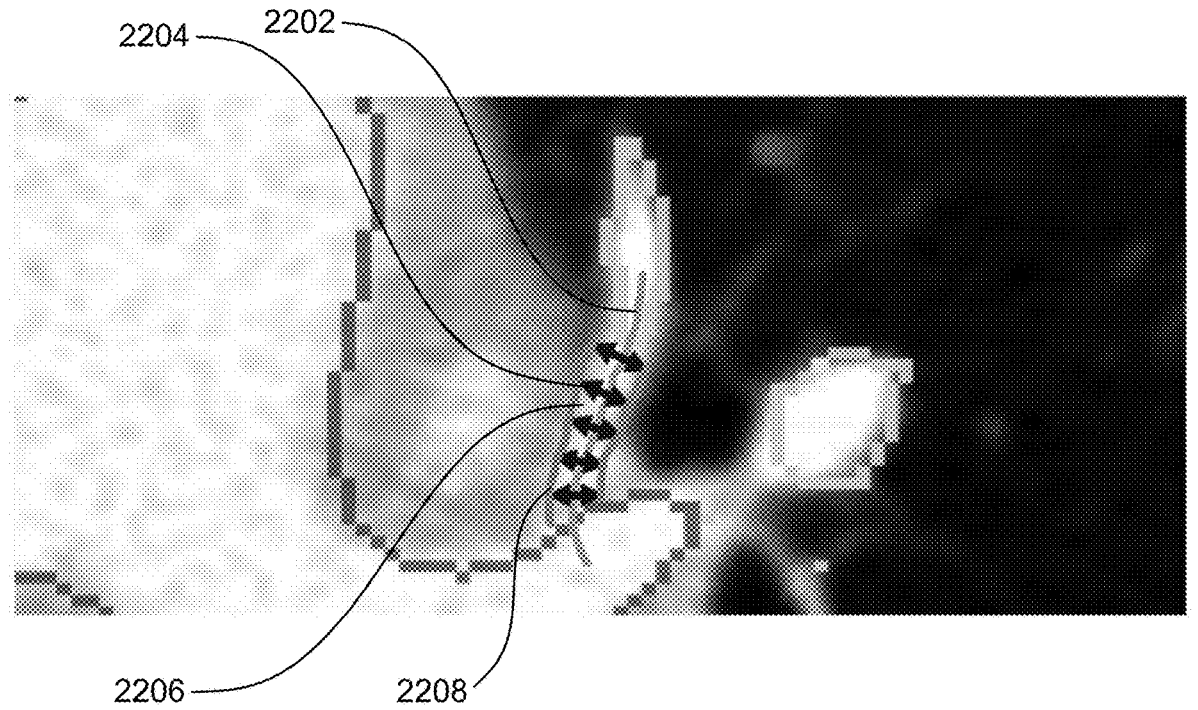

The method of closing holes may also include creating a segmentation from the shortest path. Creating a segmentation from the shortest path may include, for each "white" point on the shortest path, estimating radius based on "white" neighborhood voxels and coloring a cone in the volume. For example, as illustrated in FIG. 22, for each "white" point 2206 on the shortest path 2202, the radius 2204 is estimated based on "white" neighborhood voxels and a cone 2208 is drawn or colored in the volume defined by the estimated radius 2204.

Figure 23:
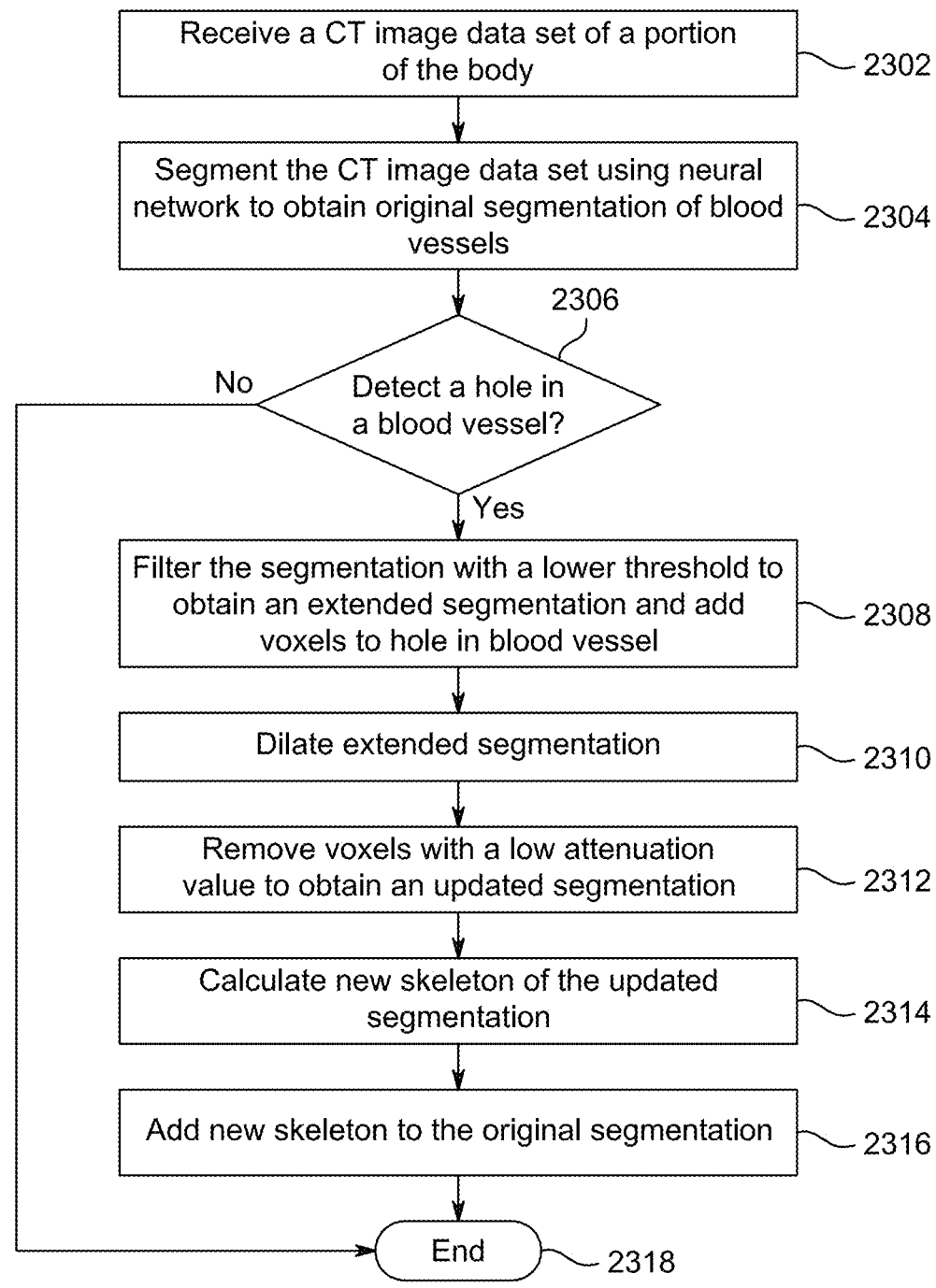
FIG. 23 is a flowchart that illustrates a method of closing holes in a segmentation.
Figure 24:
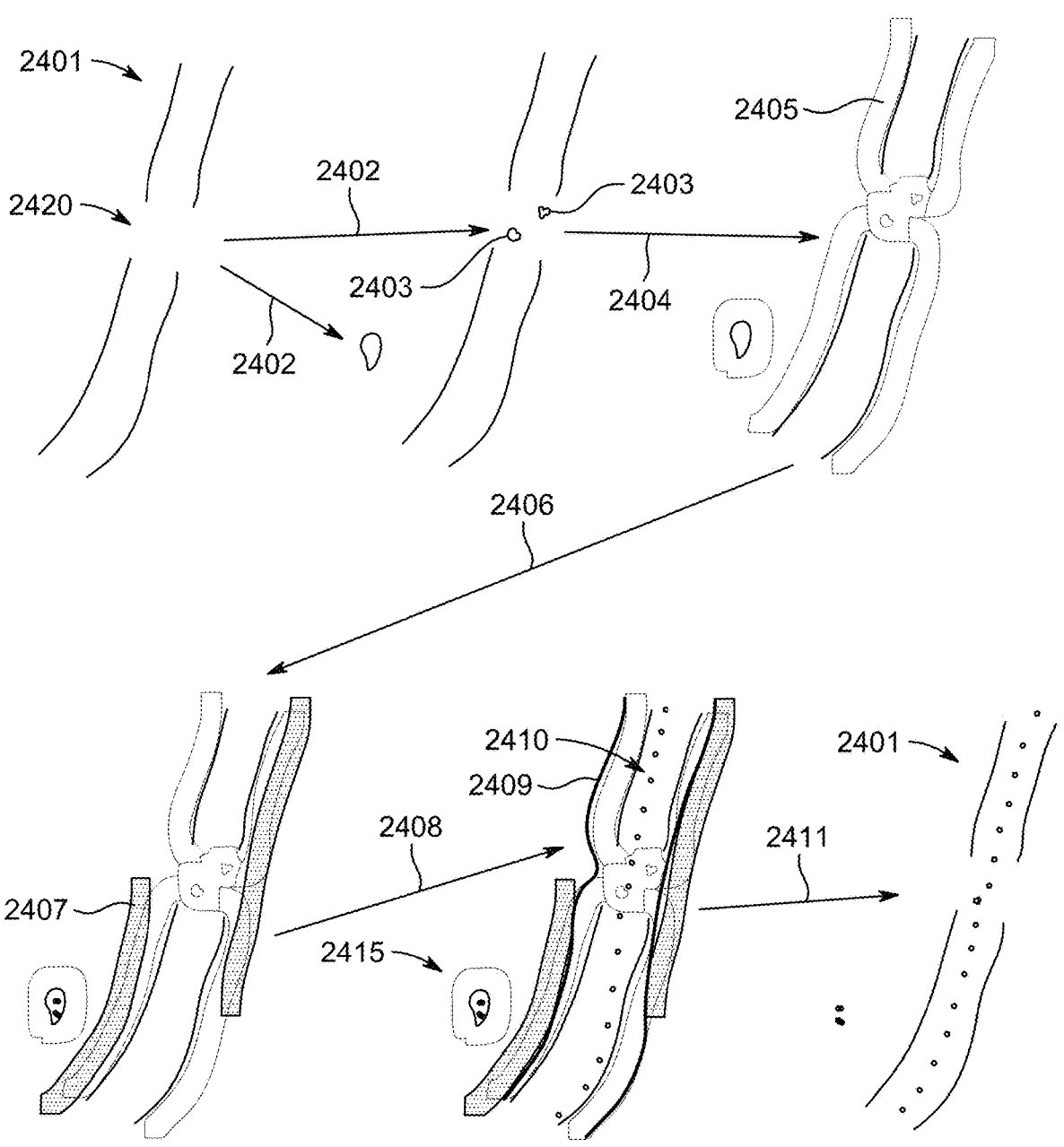
FIG. 24 is a flow diagram that illustrates the method of FIG. 23.

In another aspect, the method 2300 of FIG. 23, which is illustrated by FIG. 24, may be employed to close holes in the segmentation of blood vessels. The method 2300 may be separately applied to artery segmentation and vein segmentation. At block 2302, a three-dimensional (3D) image data set of a portion of the body, e.g., the lungs, is acquired or received. At block 2304, the 3D image data set is segmented to identify blood vessels. At block 2306, the method 2300 determines whether a hole is detected in a blood vessel. If a hole is detected in a blood vessel, at block 2308 and as illustrated in step 2402 of FIG. 24, the segmentation, e.g., the segmentation probability map, is filtered with a lower threshold, e.g., a threshold of 0.5, to obtain an extended segmentation, and voxels are added to the blood vessel of the extended segmentation.

At block 2312 and as illustrated in step 2406, voxels with low attenuation values (i.e., low Hounsfield values) 2407 are removed. After the morphological dilation, a region of air with a low attenuation value (grayscale in the CT images) can be added. Thus, this region of air is removed. At block 2314 and as illustrated in step 2408, the segmentation is updated yielding an updated segmentation 2409 and the new skeleton 2411 of the updated segmentation 2409 is calculated. The new skeleton 2411 is used because new regions, e.g., new region 2415, are added to the original segmentation 2401 that are not blood vessels. By skeletonization all irrelevant voxels are removed and a connection through the holes, e.g., hole 2420, is created. At block 2316 and as illustrated in step 2410, the new skeleton 2411 is added to the original segmentation 2401. In aspects, if the method 2300 misses holes, more holes may be collected. Additional methods may be employed to handle long holes and holes with different class labels in their end.

Figure 25A:
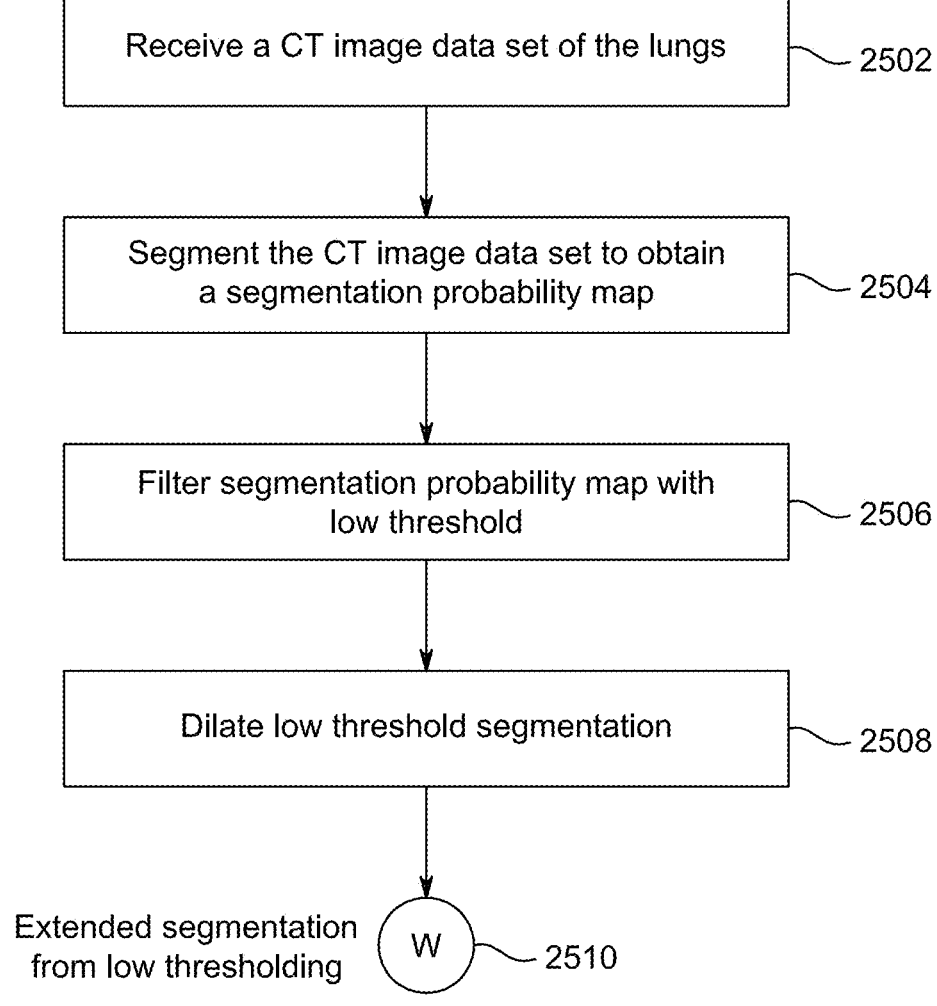
FIGS. 25A-25C is a flowchart that illustrates another method of closing holes in a segmentation.

In aspects, the segmentation may be extended using a low threshold on the segmentation probability map. As shown in FIG. 25A, this may involve filtering the segmentation probability map with a low threshold at block 2506 and applying a morphological dilation on the segmentation probability map at block 2508 after acquiring a CT image data set of the lungs at block 2502 and segmenting the CT image data set to obtain the segmentation probability map at block 2504. The result of this method is the extended segmentation from low thresholding 2510.

Figure 25B:
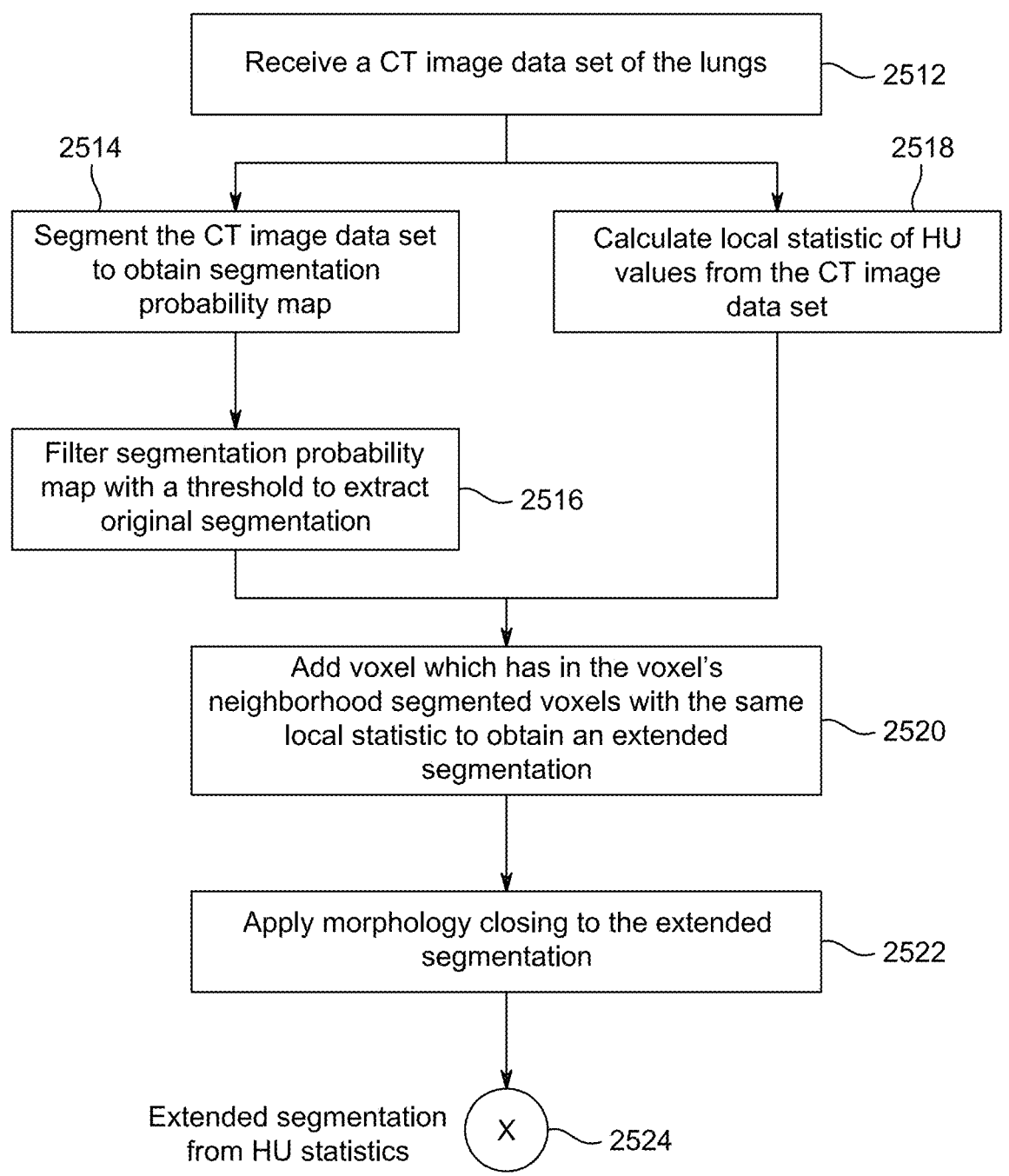

Alternatively, the segmentation may use local Hounsfield Units (HU) statistics from the CT volume. This may involve filtering the segmentation probability map with a threshold of, for example, 0.5 to extract the original segmentation, calculating the local HU statistic according to the CT volume, and extending the segmentation by adding voxels which have segmented neighbors with the same HU statistics. FIG. 25B illustrates an example of a method of extending segmentation from HU statistics.

At block 2512, a CT image data set of the lungs is acquired and, at block 2514, the CT image data set is segmented to obtain a segmentation probability map. At block 2516, the segmentation probability map is filtered with a threshold to extract the original segmentation. The threshold may be 0.5 or another threshold, e.g., 0.3, 0.4, or 0.6, suitable for extracting the original segmentation. At block 2518, the local statistic of HU values is calculated from the CT volume. At block 2520, a voxel, which has in its neighborhood segmented voxels with the same local statistic, is added to obtain an extended segmentation. Then, at block 2522, a morphology closing is applied to the extended segmentation to obtain an extended segmentation from HU statistics 2524.

Figure 25C:
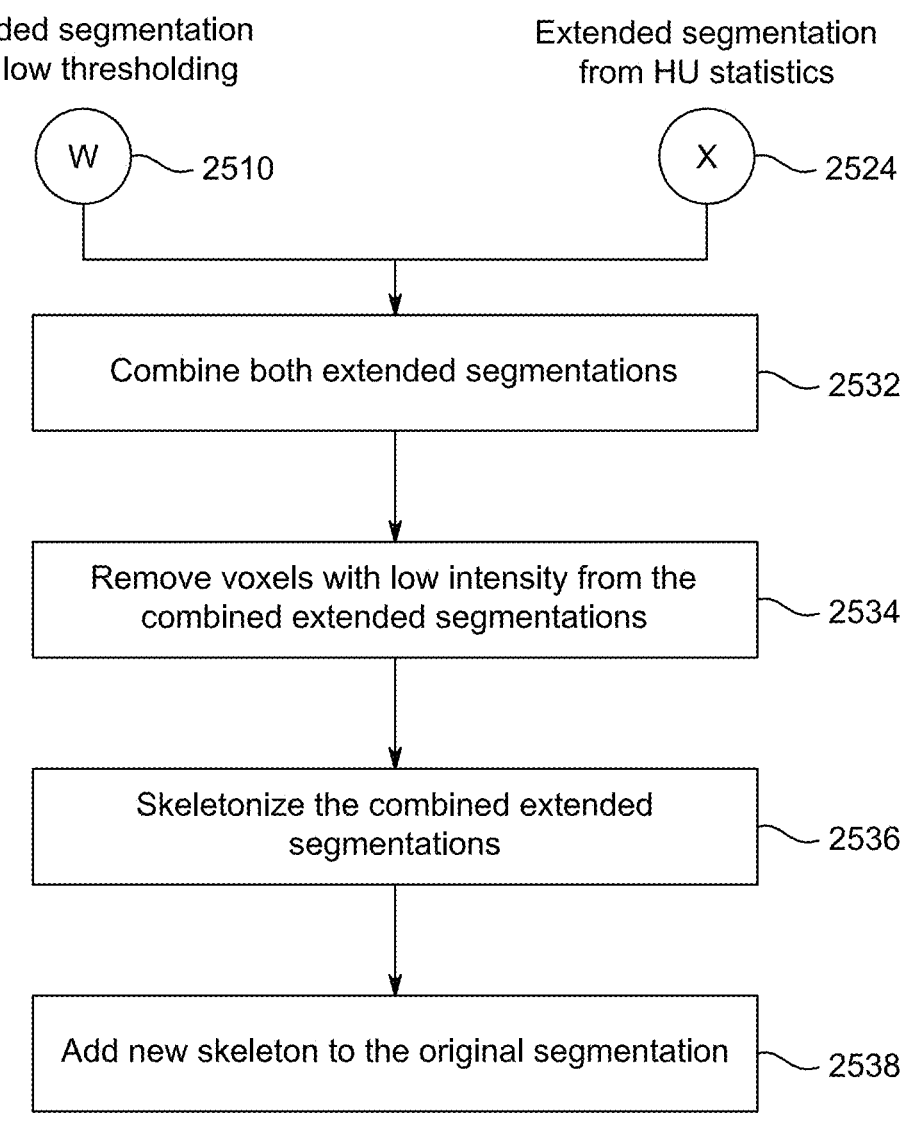

As another alternative, the extended segmentation from low thresholding 2510 and the extended segmentation from HU statistics 2524 may be combined. Then, the resulting combination may be skeletonized to connect and not add voxels that are not blood vessel voxels. FIG. 25C illustrates an example of a method of combining both extended segmentations to ultimately add a new skeleton to the original segmentation. At block 2532, the extended segmentation from low thresholding 2510 and the extended segmentation from HU statistics 2524 are combined. At block 2534, voxels with low intensity are removed from the combined extended segmentations. At block 2536, the combined extended segmentations are skeletonized. Then, at block 2538, a new skeleton is added to the original segmentation.

After detecting roots in the blood vessel segmentation, the methods of this disclosure detect coordinates of peripheral points or endpoints 2811, 2812 in the blood vessel segmentation 2801, 2802, as illustrated in the blood vessel map 2800 of FIG. 28. In one aspect, a first batch of endpoints are collected using region growing on the segmentation skeleton or centerline. Next, a second batch of endpoints are collected after initial trees are reconstructed, using connected component analysis on the centerline pieces left untracked by the initial trees.

Figure 29:
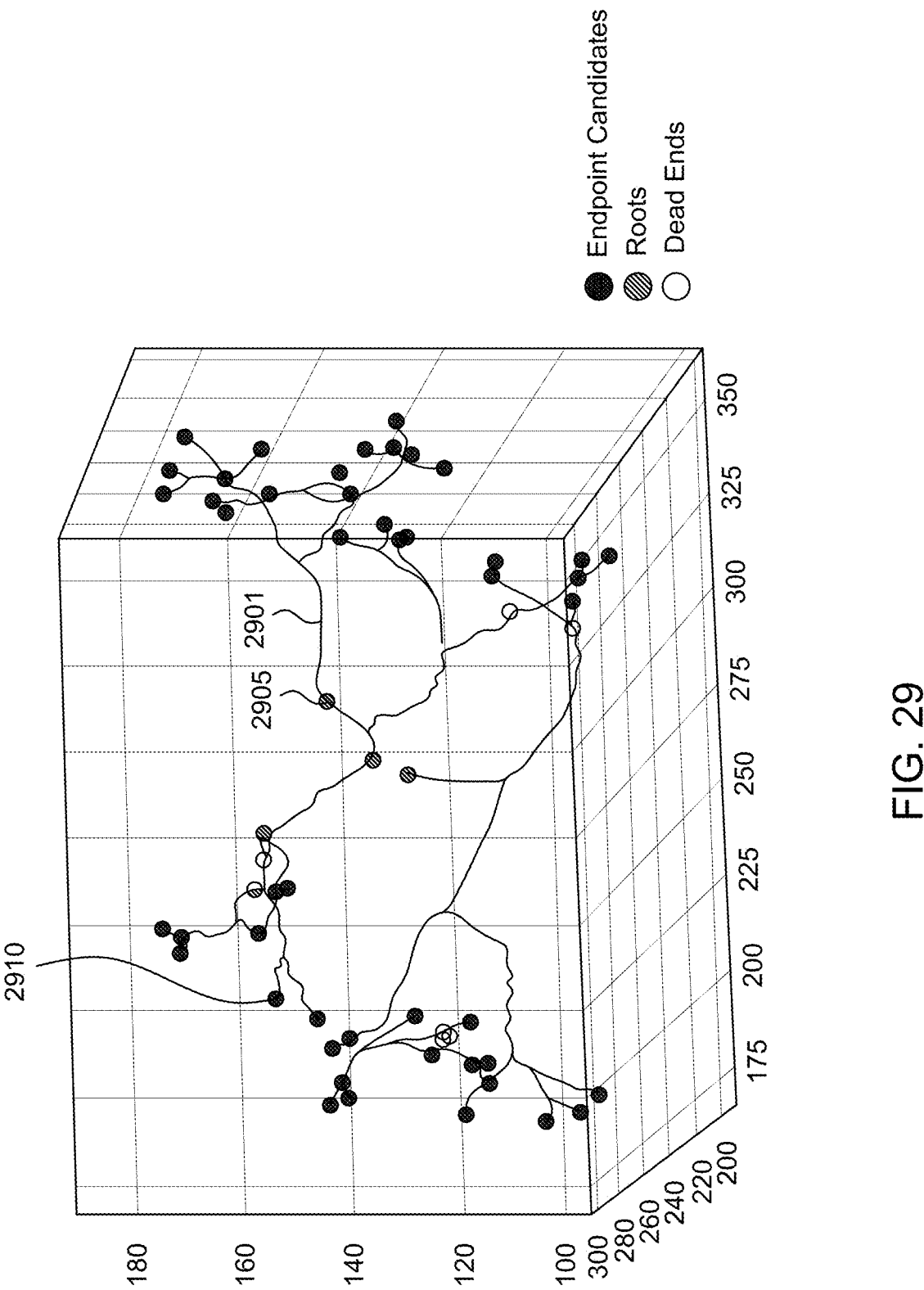
FIG. 29 is a diagram that illustrates a 3D graph of connected components of untracked skeleton voxels used to detect endpoints.

Referring to the 3D blood vessel skeleton graph of FIG. 29, for the first batch, the endpoint detection method may include generating a skeleton 2901 or centerline from the blood vessels segmentation, locating points on skeleton closest to the detected roots 2905, and from each detected root 2905 perform region growing. Region growing may include iteratively going over the skeleton voxels not yet tracked. If the region growing reaches a voxel without any neighbors that have not yet been visited, the voxel is marked as an endpoint 2910. Optionally, the region growing may be terminated before reaching the final endpoint based on conditions such as minimal vessel radius estimation or based on some "vesselness" score such as the Frangi filter.

Figure 30:
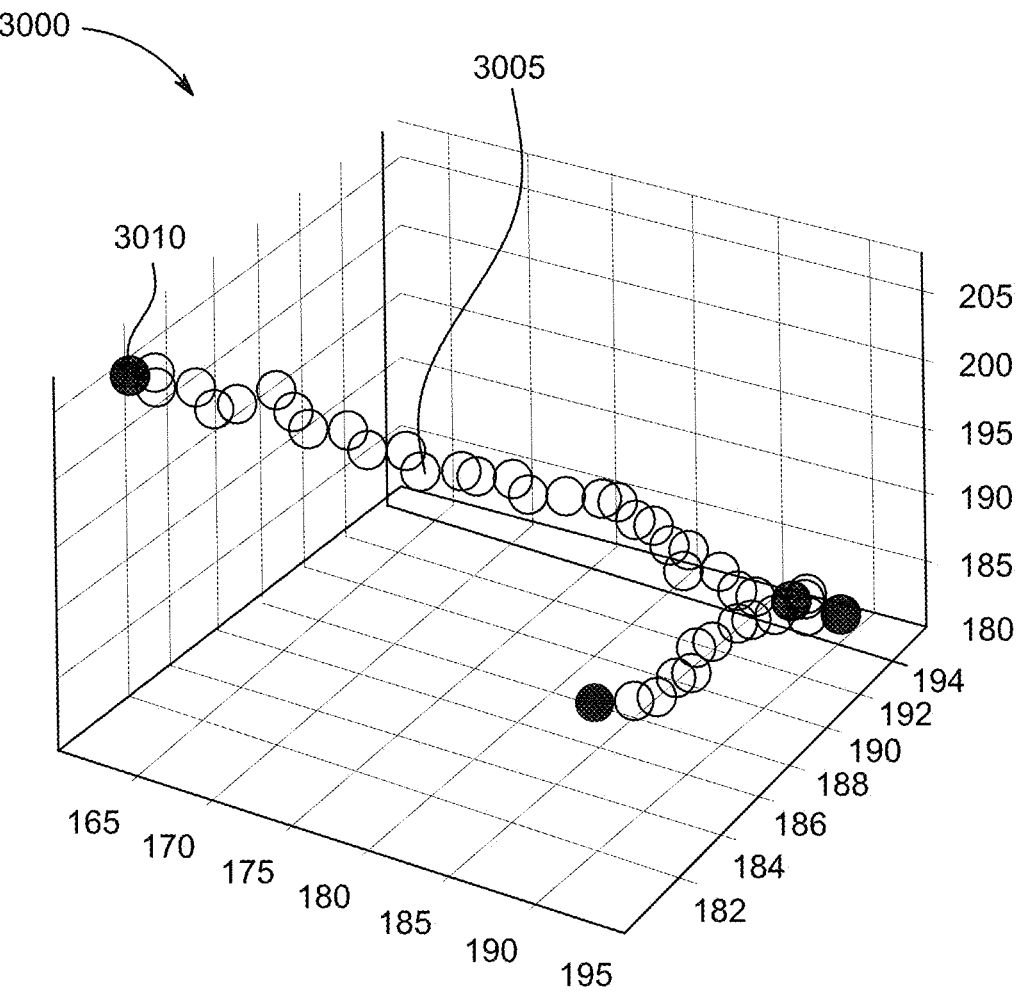
FIG. 30 is a diagram that illustrates a blood vessel skeleton graph used to detect endpoints.

For the second batch, the endpoint detection method may include generating a segmentation volume of untracked vessels by subtracting the segmentation generated from the initial trees, i.e., trees generated from the first batch of endpoints, from the original segmentation. For the second batch, the endpoint detection method may further include finding skeleton voxels, that are inside the untracked vessels e.g., the skeleton voxels 3005 shown in the 3D graph of FIG. 30, by sampling the segmentation generated from the initial trees, applying a connected component analysis to the untracked skeleton voxels, and, from each connected component, use the voxels with degree 1, i.e., voxels connected only to a single other skeleton voxels, as endpoints, e.g., the endpoints 3010 shown in FIG. 30.

Figure 31:
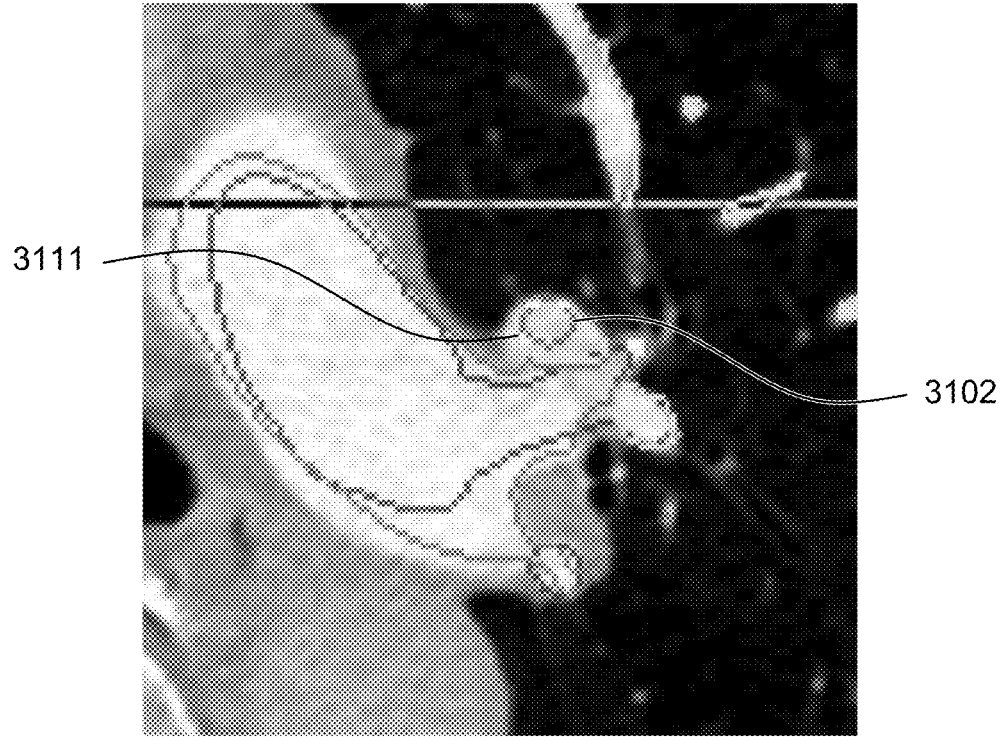
FIGS. 31-33 are annotated images that illustrate examples of blood vessels misclassified by the neural network.
Figure 32:
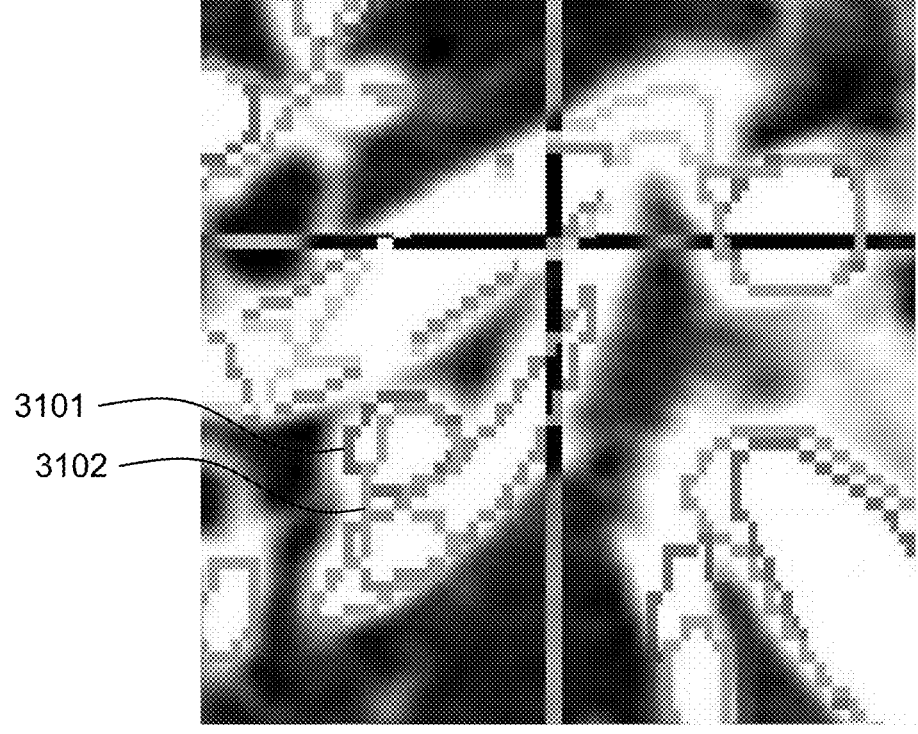
Figure 33:
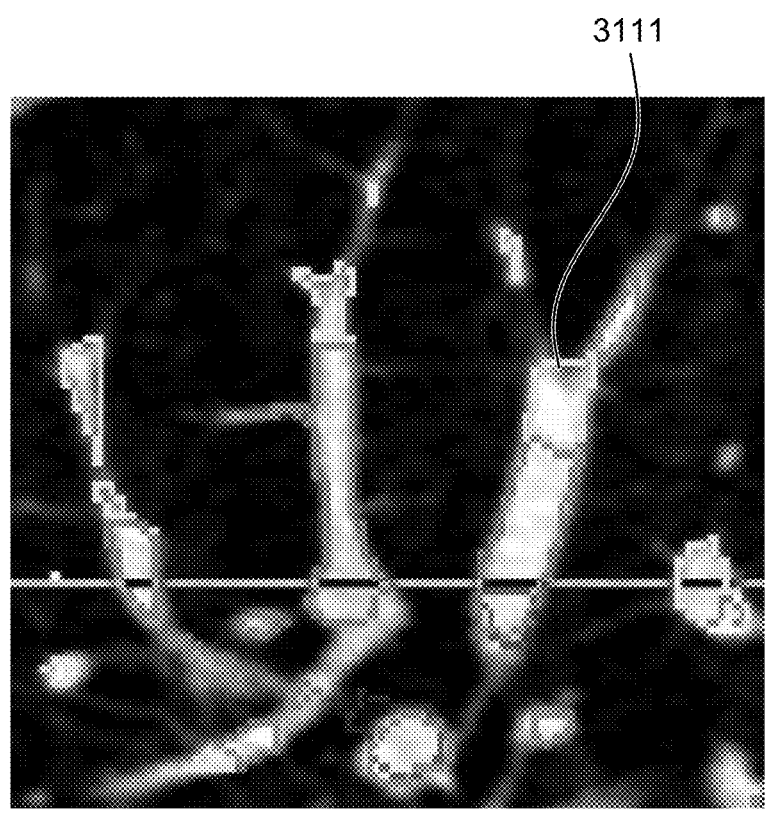

When the neural network classifies voxels, the classifying accuracy may be high, e.g., greater than 95%. However, when reconstructing a path from each endpoint to the heart, for example, small false classifications may lead to erroneous root selection or path creation. For example, as illustrated in FIG. 31, the neural network may misclassify a vein 3102, which is shown as being manually annotated by a clinician, as an artery 3111. In another example illustrated in FIG. 32, the neural network may misclassify an artery 3101, which is shown as being manually annotated by a clinician, as a vein 3112. In another example illustrated in FIG. 33, the neural network may falsely classify a section of a vessel as an artery 3111 (which may be referred to as discontinuous vessel classification).

Figure 34:
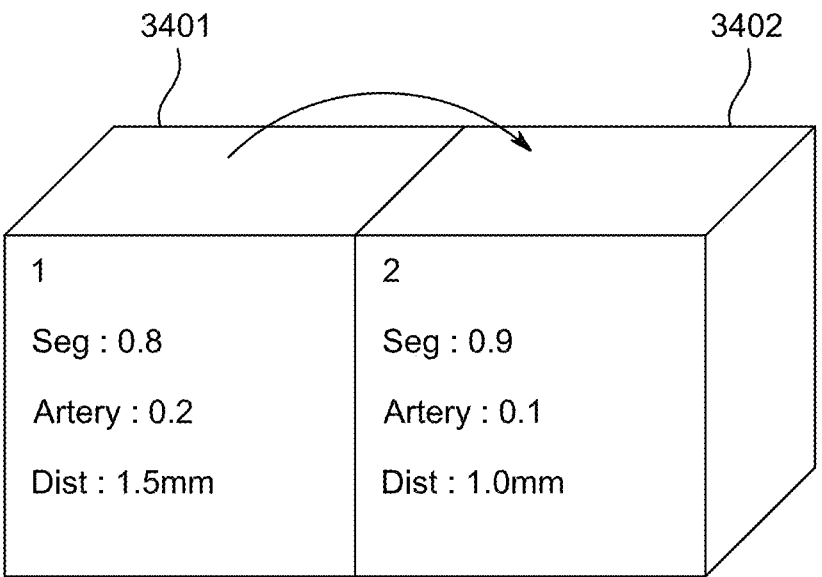
FIG. 34 is a schematic diagram that illustrates neighboring voxels and statistics associated with the voxels.

In one aspect, the methods of the disclosure find the optimal paths connecting each endpoint at the lung periphery with the endpoint's compatible root in the heart. The optimal path is the path that traverses the true vessel path to the heart. Generating an optimal path may include a preprocessing stage. The preprocessing stage may include building a graph in which the voxels segmented as a blood vessel are the vertices of the graph and the edges are based on a neighborhood definition between voxels. The preprocessing stage may also include weighting the edges as a function of estimated segmentation probabilities, vessel probabilities (e.g., artery or vein probabilities), and/or distance to a segmentation centerline at the connected vertices, which are voxels. For example, FIG. 34 illustrates neighboring voxels—voxel 3401 and voxel 3402—and the estimated values of the voxels. For example, voxel 3401 has an estimated segmentation probability of 0.8, an artery probability of 0.2, and a distance of 1.5 mm to a segmentation centerline; and voxel 3402 has an estimated segmentation probability of 0.9, an artery probability of 0.1, and a distance of 1.0 mm to a segmentation centerline. The edge connecting from voxel 3401 to voxel 3402 may weighted according to the segmentation and artery probability values of the voxels.

The optimal path may be a shortest path generated based on possible scores. The edges may be weighted based on one or more of: the segmentation probability of the neighboring voxel, the distance to the centerline of the neighboring voxel, the classification probability, and the distance between the center of the current voxel and the center of the neighboring voxel. The classification probability is used differently if the shortest path algorithm is started from an artery root or a vein root. This means that two sets of weights are generated: one set of weights for connecting an endpoint to the artery root and another set of weights for connecting endpoints to the vein roots. In the case of an artery root, a weight may be the vein probability (i.e., by subtracting the artery probability from the decimal number 1) of the neighboring voxel. In the case of a vein root, a weight may be the artery probability of the neighboring voxel.

The distance to the centerline is a volume with a distance from the centerline of the segmentation such that the segmentation has a maximum value on the boundaries. The weight based on the distance to the centerline may make the shortest path go through the center of the blood vessel, which may result in improved estimation of the radius of the blood vessel and improved merging of paths from different paths. The weight based on the distance to the centerline may also help the path stay on the same vessel while passing through the intersection of an artery and a vein.

The results of the shortest path algorithm give instructions on how to go from each endpoint to each root. Each path may be given one or more scores. For example, an SP score may be the sum of the weights of all the edges traversed by the path. Each path may be given another score based on the topological distance of the path. The neural network estimates a topological embedding for each point along the path. The topological embedding may be used to compute the distance (e.g., L2 norm) between each point embedding and a point X steps further away along the path. In one example, each path may be given a topological score that is a maximum topological distance value computed for each path. The SP score and the topological score may be combined to evaluate each path. The SP score and the topological score may be combined by, for example, multiplying the SP score and the topological score. To select a root, for each endpoint the combined scores of paths connecting to all possible roots (e.g., artery roots or vein roots relevant for the endpoint) and the path with the lowest score is selected.

Figure 36A:
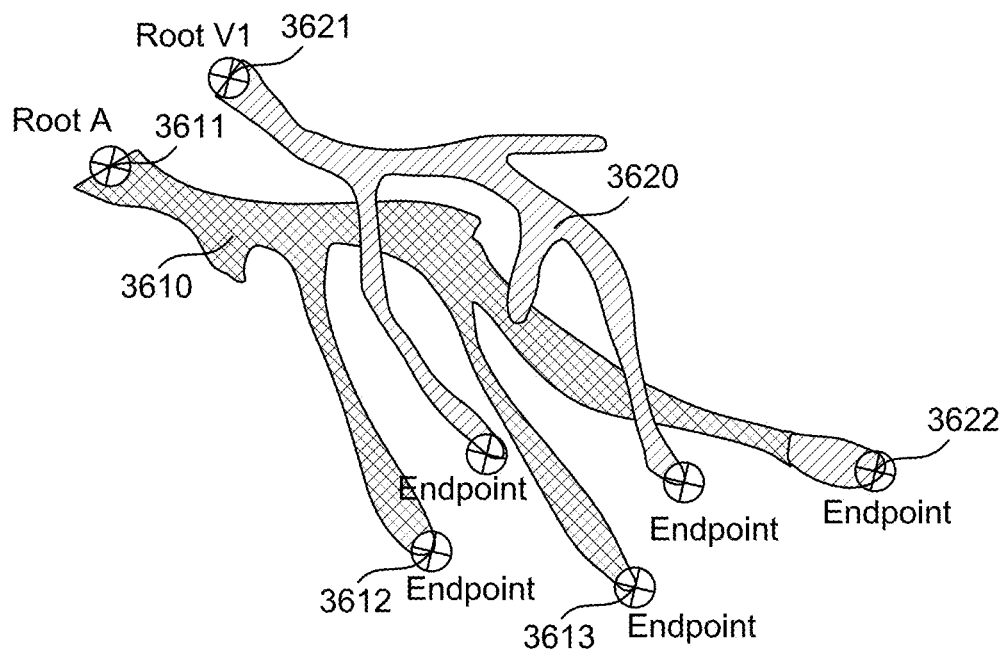
FIGS. 36A-36D are diagrams that illustrate a method of creating a blood vessel graph or tree structure.
Figure 36B:
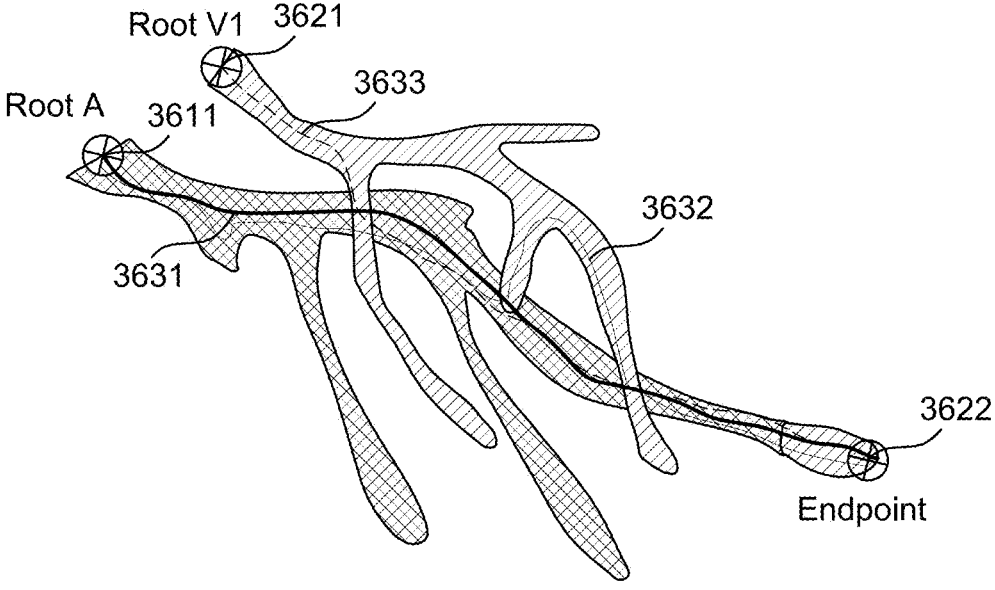

After performing segmentation, classification, and closing holes in the segmentation, directed graphs are generated. FIGS. 35 and 36A-36D show an example of a method of creating a blood vessel graph or tree structure, which may be used to generate a 3D mesh model. These steps may be implemented in executable code such as software and firmware or in hardware utilizing the components and systems of FIG. 42. At block 3506, the roots or starting points 3611, 3621 and the endpoints 3612, 3613, 3622 of the segmented blood vessels 3610, 3620 are detected, as illustrated in FIG. 36A. At block 3508, optimal paths 3631-3633 from possible starting points 3611, 3621 to an endpoint are calculated, as illustrated in FIG. 36B.

Figure 36C:
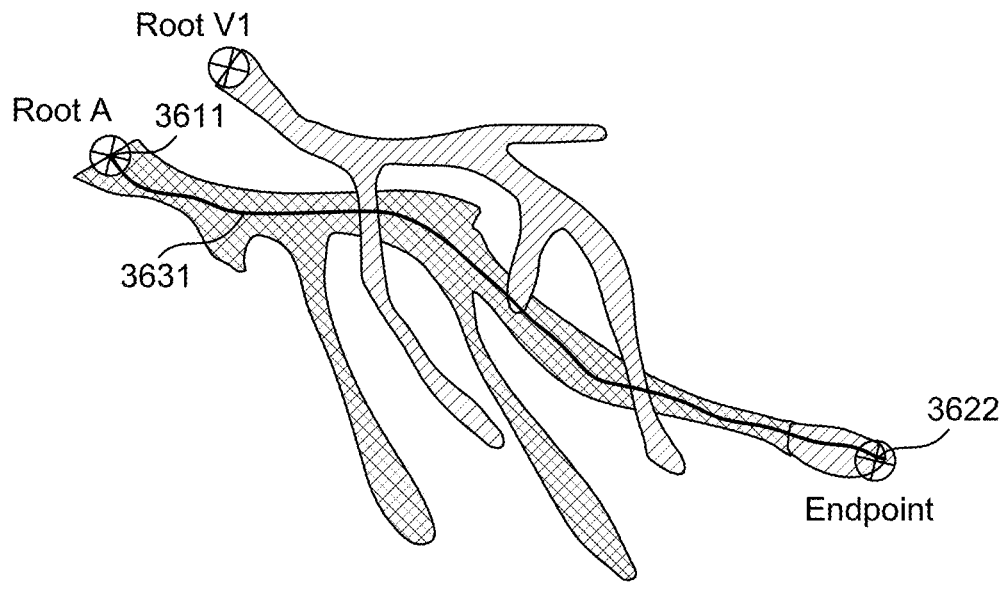
Figure 36D:
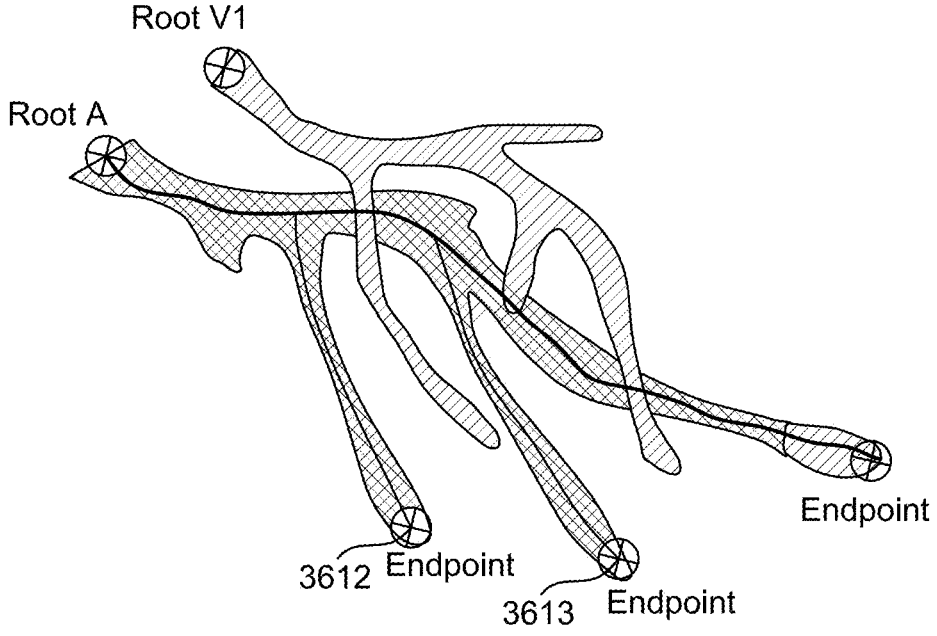

At block 3510, the best starting point 3611 is selected from the possible starting points, and, at block 3512, the class of the optimal path 3631 from the best starting point 3611 to the endpoint 3622 is selected, as shown in FIG. 36C. At block 3514, the method 3500 determines whether there is another endpoint to process. If there are other endpoints to process, the processes of blocks 3508-3512 are repeated for the other endpoints, e.g., endpoints 3612, 3613. If there are no other endpoints to process, the paths of the same starting point are merged into a directed graph or tree structure at block 3516, as illustrated in FIG. 36D. Then, at block 3518, the method 3500 ends.

Figure 37:
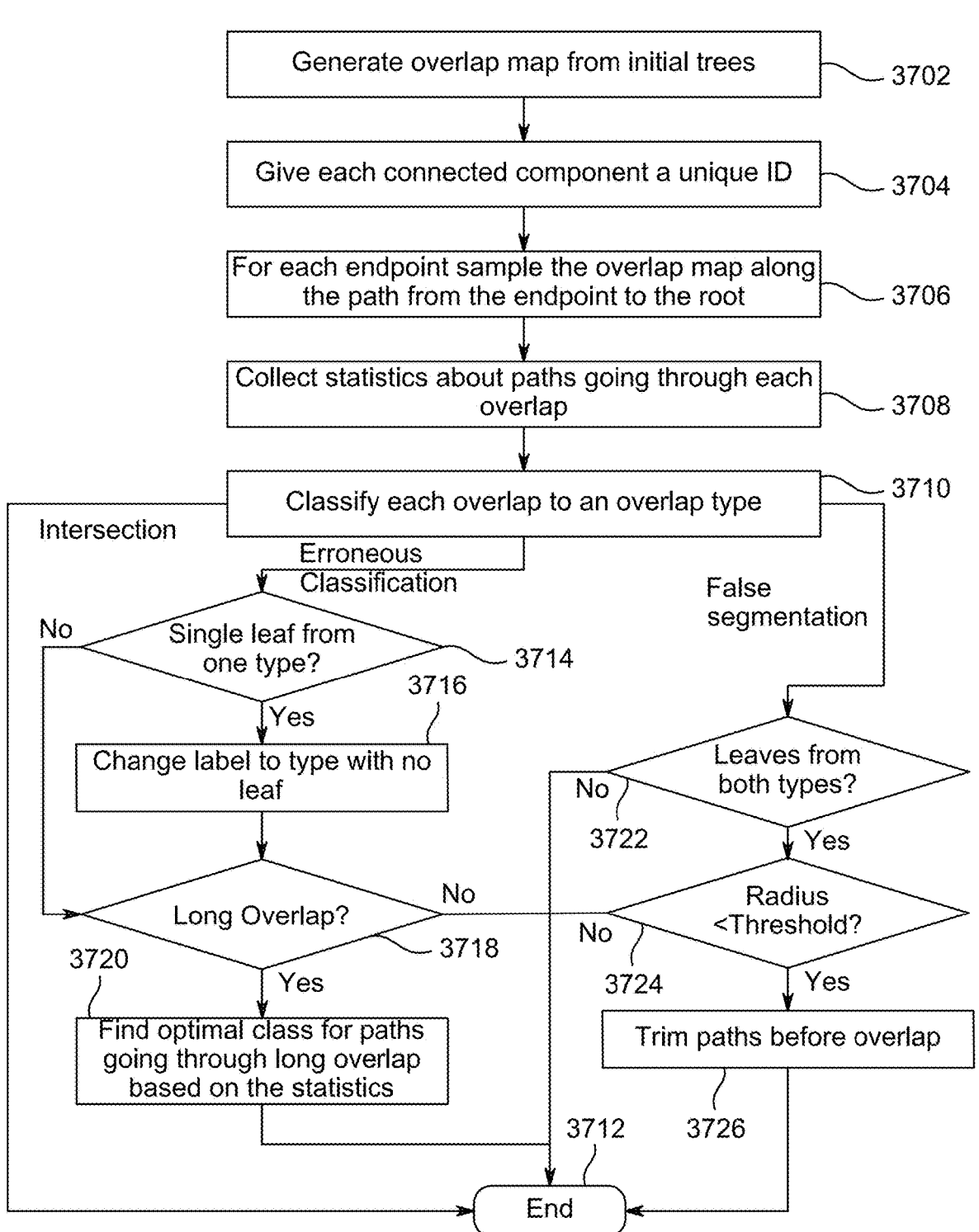
FIG. 37 is a flowchart that illustrates a method of processing overlaps between blood vessels.

In aspects, vessels may be classified and tracked back to the heart independently. However, there may be overlaps between artery and vein branches. Thus, overlaps between blood vessel trees are solved at block 416 of the method 400 of FIG. 4. The overlaps may be solved in a post process. The post process may include detecting overlaps, classifying each overlap to a specific overlap type, and correcting the vessel classification, if needed. Solving overlaps between directed graphs or trees may be performed according to the method 3700 of FIG. 37.

Figure 38A:
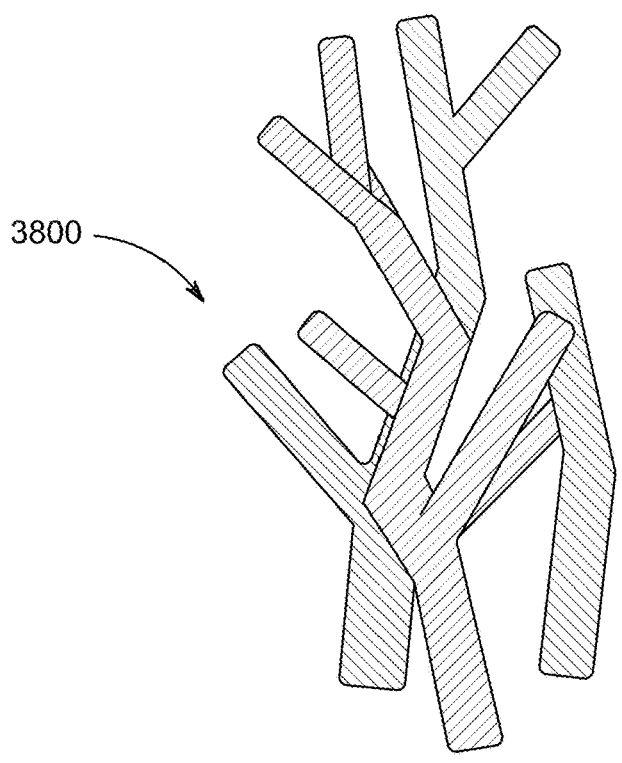
FIG. 38A is a diagram that illustrates an example of a 3D vasculature model.
Figure 38B:
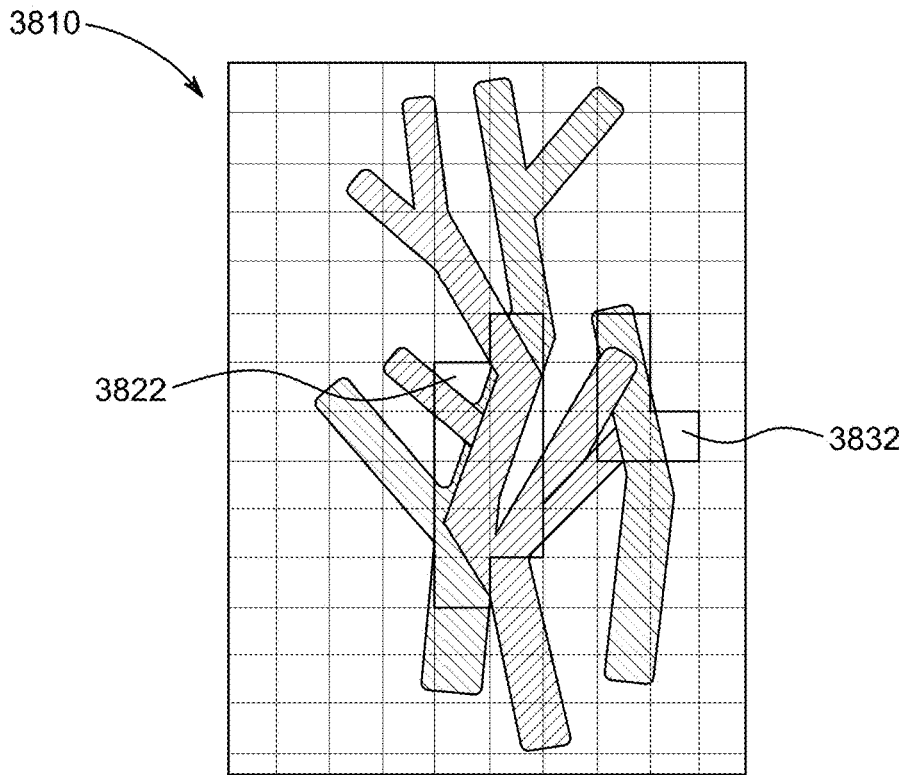
FIGS. 38B-38D are diagrams of examples of overlap maps that illustrate the processing of overlaps.
Figure 38C:
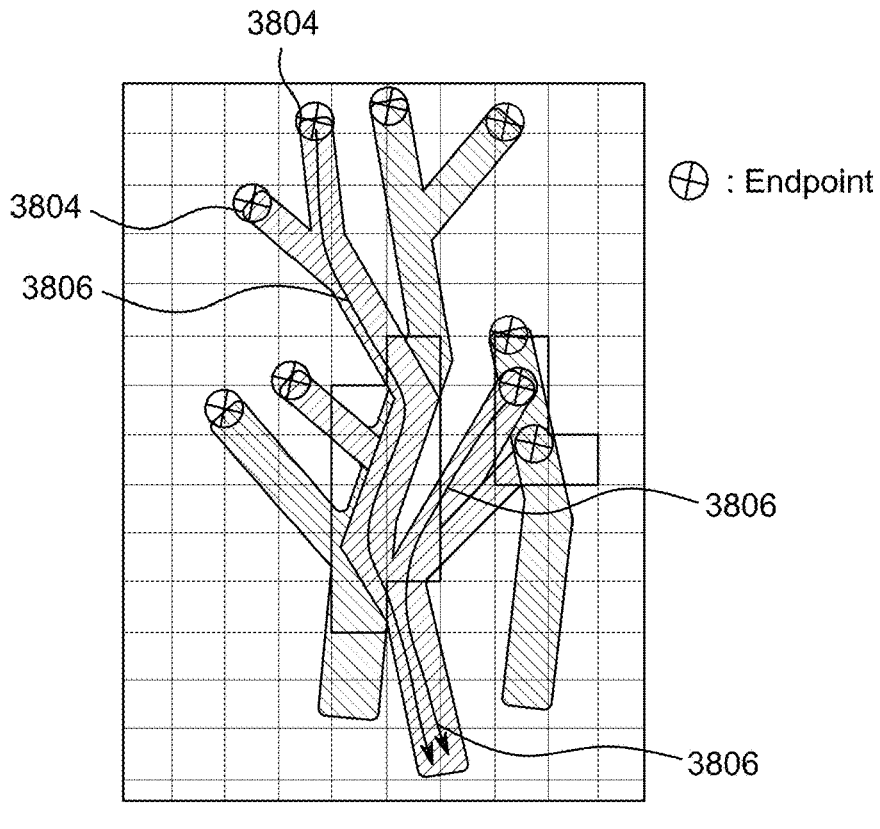

At block 3702, an overlap volume map 3810 of FIG. 38B is generated from initial trees 3800 of FIG. 38A. Next, a connected component analysis is performed on the overlap volume map 3810 in which each connected component 3822, 3832 is given a unique ID at block 3704. At block 3706, for each endpoint 3804 of FIG. 38C, the overlap volume map 3810 is sampled along a path 3806 from the endpoint 3804 to the root 3808. At block 3708, statistics about the paths which go through each overlap are collected. The statistics may include one or more of the following: average vessel radius; overlap length (which may be normalized by the average radius); the number of paths having an endpoint near the overlap; the number of paths going through the overlap, which may be separated into subsets of paths classified as artery and paths classified as veins; and, for each subset; and collected scores, which may include one or more of topological embedding score, shortest path score, and sample of the network classification.

Figure 39A:
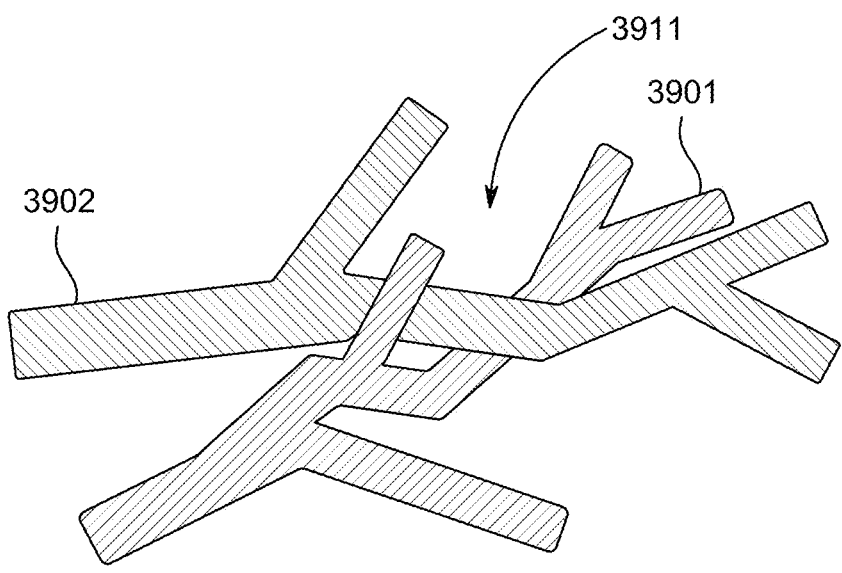
FIG. 39A is a schematic diagram that illustrates an example of blood vessel intersection.
Figure 39B:
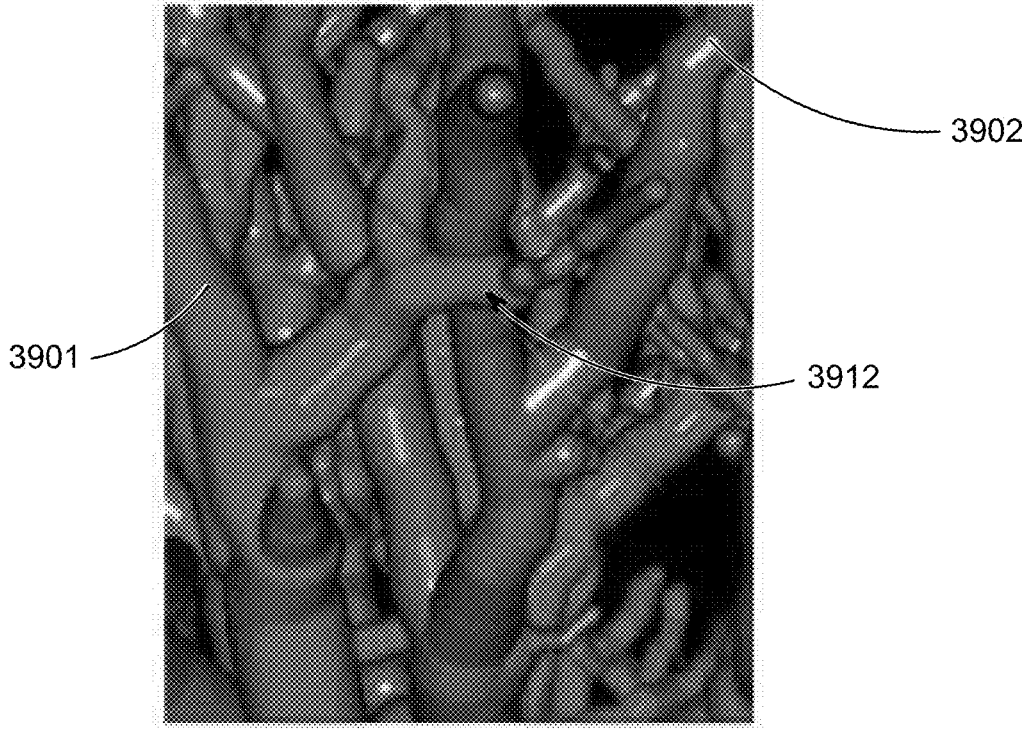
FIG. 39B is a 3D vasculature model that illustrates an example of blood vessel intersection.
Figure 40A:
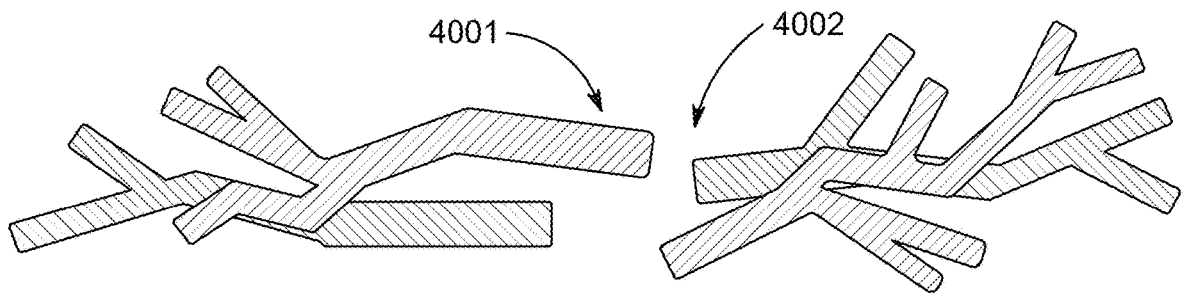
FIG. 40A is a schematic diagram that illustrates an example of erroneous classification of endpoints.
Figure 40B:
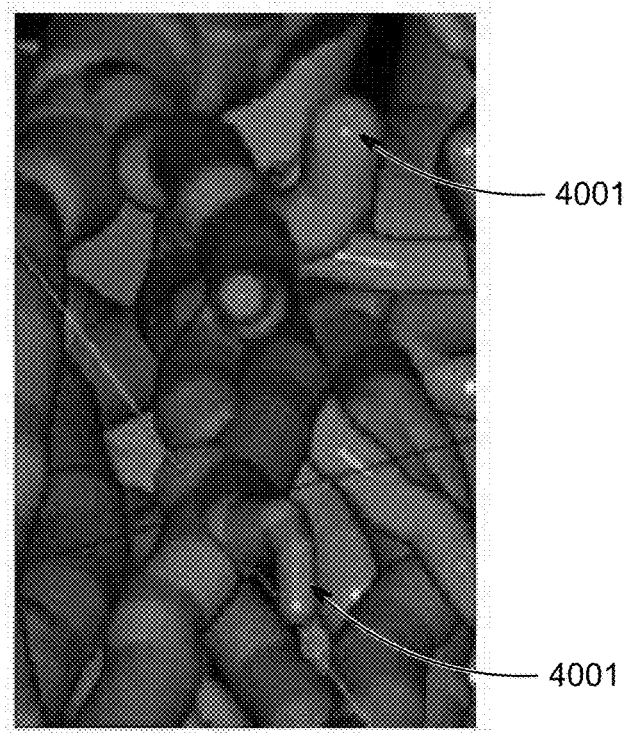
FIG. 40B is a 3D vasculature model that illustrates an example of erroneous classification of endpoints.
Figure 41A:
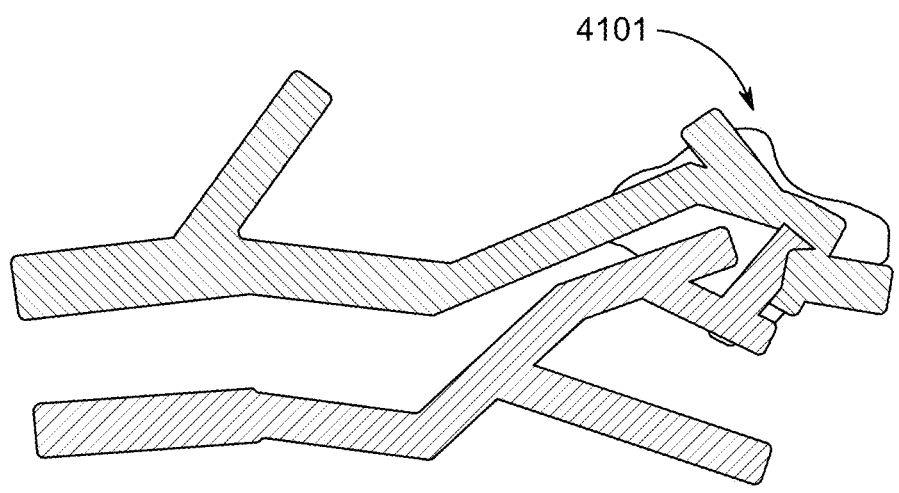
FIG. 41A is a schematic diagram that illustrates an example of false segmentation.
Figure 41B:
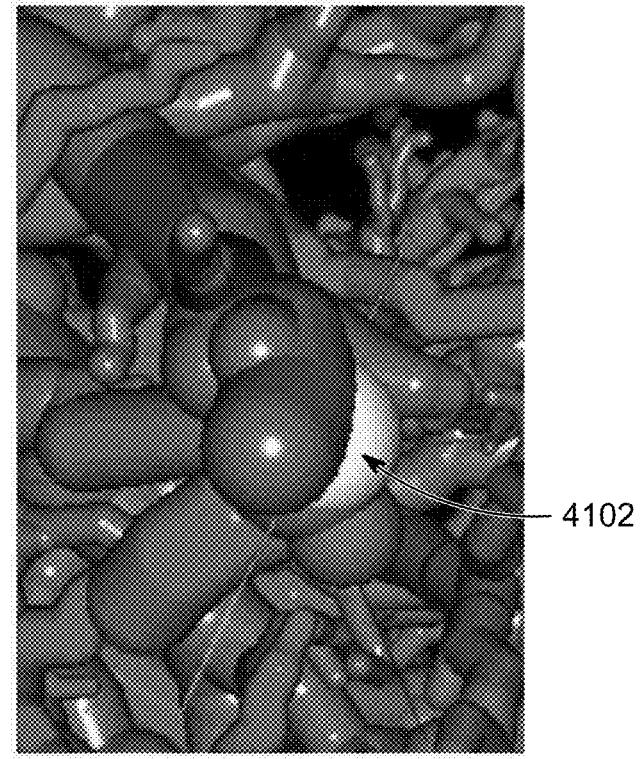
FIG. 41B is a 3D vasculature model that illustrates an example of false segmentation.

At block 3710, each overlap is classified to an overlap type. FIGS. 39A-41B are diagrams that illustrate examples of blood vessel overlap types. As illustrated in FIGS. 39A and 39B, the overlap types may include a valid intersection (at points 3911, 3912) between an actual artery 3901 and an actual vein 3902. As illustrated in FIGS. 40A and 40B, the overlap types may include erroneous classification of endpoints (for example, at points 4001 and 4002). The overlap types may include false segmentation, which may be caused by, for example, lesions, atelectasis, or fissures adjacent to an overlap. For example, FIGS. 41A and 41B illustrate portions 4101 and 4102, respectively, of false segmentation.

Figure 38D:
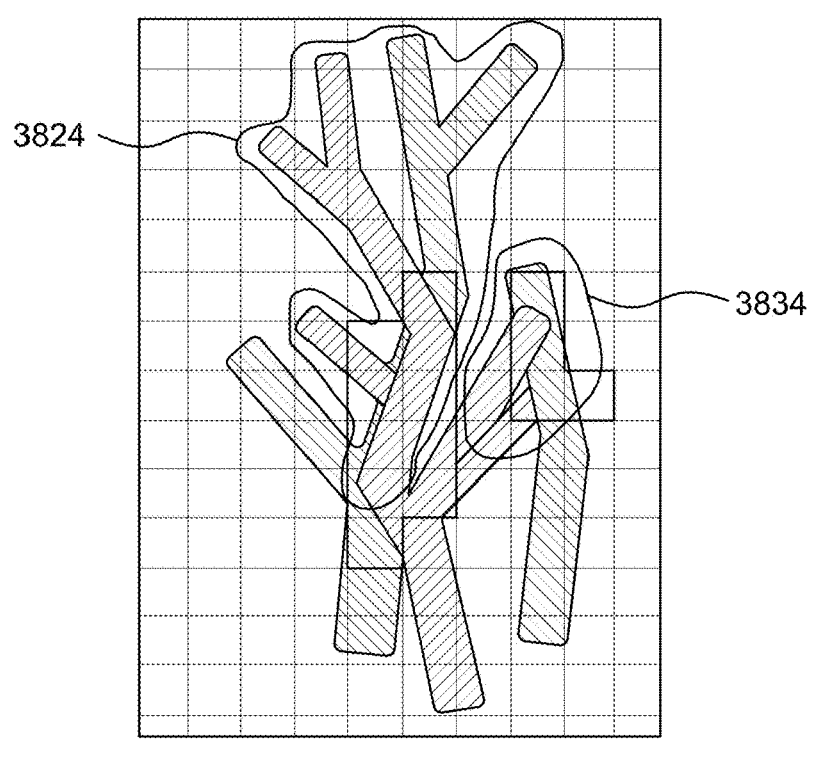

If the overlap type is an intersection between blood vessels, as illustrated, for example, by the overlap 3834 of FIG. 38D, the method 3700 ends at block 3712 and no correction is performed. If the overlap type is an erroneous classification, the method 3700 determines whether the overlap is a single leaf from one classification type at block 3714. If the overlap is a single leaf from one classification type, the classification of the overlap is changed to the type with no leaf at block 3716.

At block 3718, the method 3700 determines whether the overlap is a long overlap, as illustrated, for example, by the overlap 3824 of FIG. 38D. If the overlap is a long overlap, an optimal classification is found for all paths going through the overlap based on the collected statistics, e.g., scores, at block 3720. If an overlap type is a false segmentation, the method 3700 determines whether there are leaves from both types at block 3722 and determines whether the radius of the blood vessel is less than a threshold at block 3724. If there are leaves from both types and the radius of the blood vessel is less than a threshold, paths before the overlap are trimmed at block 3726. Otherwise, if there are no leaves from both types or the radius of the blood vessel is not less than a threshold, the method 3700 ends at block 3712 without performing correction.

Alternatively, the overlaps between blood vessel trees may be solved by using a graph cut algorithm. The graph cut algorithm assumes there are no connections between a root of an artery tree and a root of a vein tree. The graph cut algorithm separates the trees that are overlapping according to scores or weights placed on the edges of the segmented arteries and veins. The graph cut algorithm may then cut the trees according to the mean cut of the weights such that there are no paths that connect the segmented arteries to the segmented veins.

As another alternative, the overlaps between blood vessel trees may be solved by an overlap split algorithm that uses the topological embedding map values. In one aspect, not all paths are processed. Overlap path segments, e.g., short overlap path segments, may be identified and a score from the topological embedding map values may be associated with identified overlap path segments. The overlap split algorithm may determine whether an overlap path segment belongs to an artery or a vein and split the overlap path segment accordingly.

The overlap split algorithm may consider various metrics associated with an overlap path segment including the length of the overlap path and scores from the topological embedding map values. For example, the overlap split algorithm may analyze the change in topological embedding map values across an edge of an overlap path segment. The overlap split algorithm may determine that two portions of the overlap path segment belong to the same blood vessel if the change in topological embedding map values across the edge of the overlap path segment is small. On the other hand, the overlap split algorithm may determine that two portions of the overlap path segment belong to different blood vessels if the change in topological embedding map values across the edge of the overlap path segment is large.

In the case of treating lung cancer by performing endo-bronchial ablation or lung surgery, a physician must understand the patient's anatomy, including the blood vessels in the vicinity of the lesion or leading to the lesion. For example, when performing a lobectomy, a surgeon is interested in blood vessels that enter and leave the specific lobe. Physicians may look at a CT scan prior to the therapeutic procedure and use the CT scan to visualize the vasculature structures and anatomical variations in order to plan the therapeutic procedure. The systems and methods of the disclosure automatically generate a patient-specific 3D model of the vasculature of a portion of a patient's body. The patient-specific 3D anatomical model of the vasculature enables a clinician to select the best surgical approach and to prevent complications. Also, the patient-specific 3D anatomical model of the vasculature may be used for procedure planning, intraoperative safety, and training of clinicians, such as surgeons.

Figure 6:
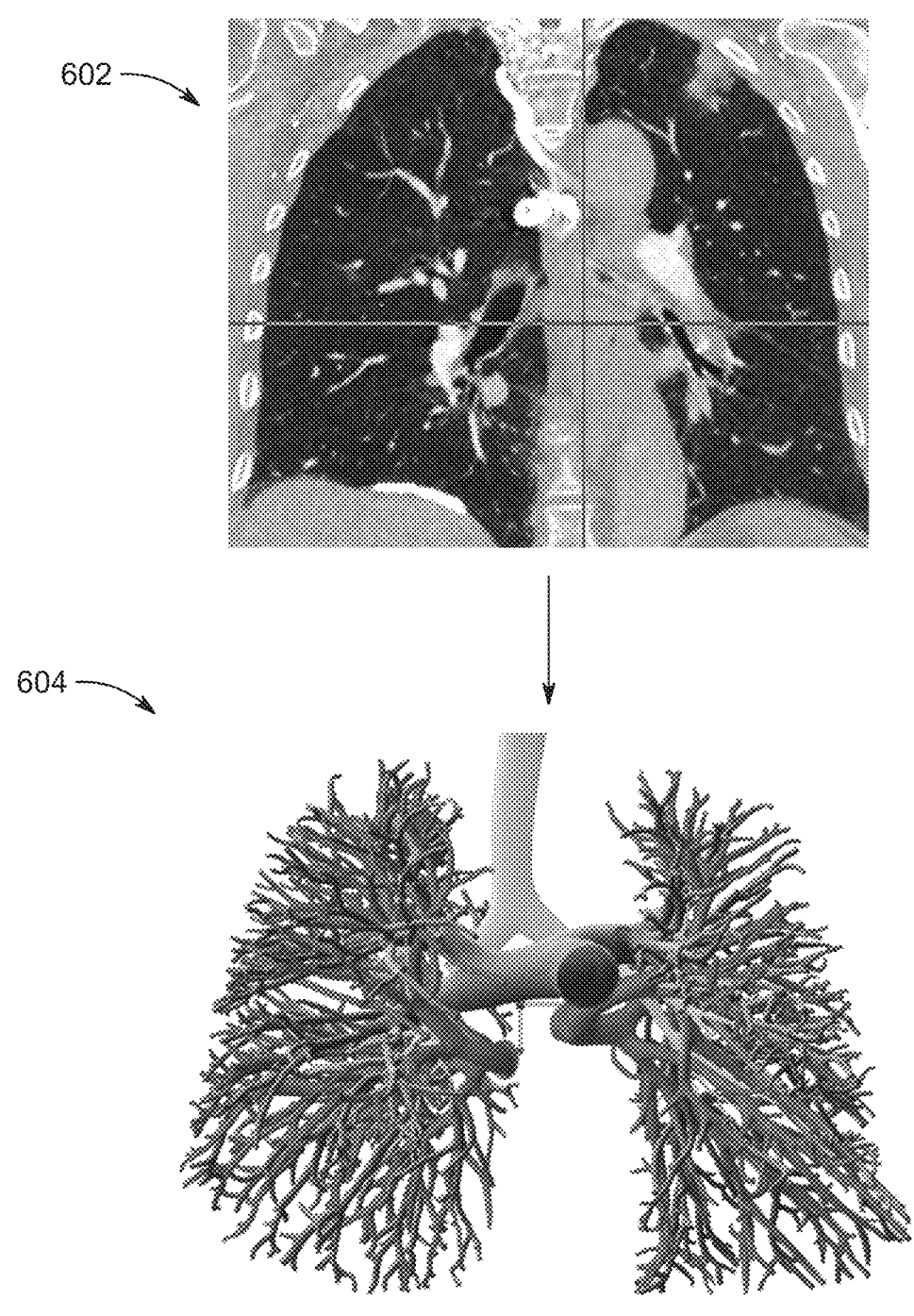
FIG. 6 is a diagram that illustrates examples of the input to and the output from the system of FIG. 1.

After a blood vessel graph or tree structure is generated, a 3D mesh is generated based on the blood vessel graph or tree structure. A 3D mesh is the structural build of a 3D model consisting of polygons. 3D meshes use reference points, which may be voxels identified in the graph, to define shapes with height, width, and depth. A variety of different methods and algorithms may be used for creating a 3D mesh, including, for example, the marching cubes algorithm. The result of the 3D mesh generation is a 3D model. FIG. 6 is a diagram that illustrates a full pulmonary blood vessel model 604 that may be generated from CT images 602 of the lungs according to the systems and methods of the disclosure. In one example, the accuracy of the 3D model may be 96.5% in the center and 95.5% lobe+5 cm.

Figure 42:
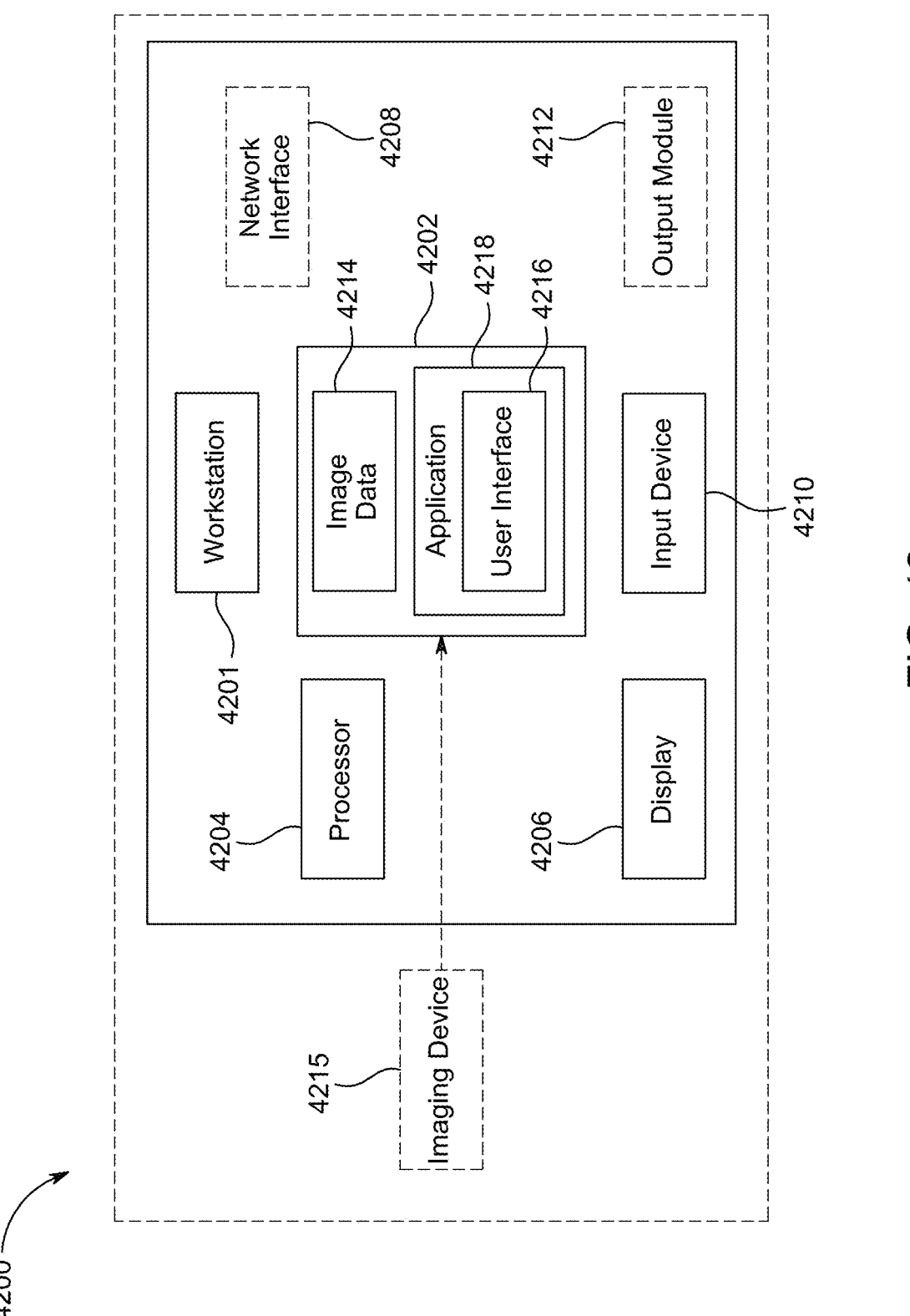
FIG. 42 is a schematic diagram of a computer system capable of executing the methods described herein.

Reference is now made to FIG. 42, which is a schematic diagram of a system 4200 configured for use with the methods of this disclosure. System 4200 may include a workstation 4201. In some aspects, workstation 4201 may be coupled with an imaging device 4215 such as a CT scanner or an MRI, directly or indirectly, e.g., by wireless communication. Workstation 4201 may include a memory 4202, a processor 4204, a display 4206 and an input device 4210. Processor 4204 may include one or more hardware processors. Workstation 4201 may optionally include an output module 4212 and a network interface 4208. Memory 4202 may store an application 4218 and image data 4214. Application 4218 may include instructions executable by processor 4204 for executing the methods of this disclosure.

Application 4218 may further include a user interface 4216. Image data 4214 may include image data sets such as CT image data sets and others useable herein. Processor 4204 may be coupled with memory 4202, display 4206, input device 4210, output module 4212, network interface 4208 and imaging device 4215, e.g., a CT imaging device. Workstation 4201 may be a stationary computing device, such as a personal computer, or a portable computing device such as a tablet computer. Workstation 4201 may embed a plurality of computer devices.

Memory 4202 may include any non-transitory computer-readable storage media for storing data and/or software including instructions that are executable by processor 4204 and which control the operation of workstation 4201 and, in some aspects, may also control the operation of imaging device 4215. In one aspect, memory 4202 may include one or more storage devices such as solid-state storage devices, e.g., flash memory chips. Alternatively, or in addition to the one or more solid-state storage devices, memory 4202 may include one or more mass storage devices connected to the processor 4204 through a mass storage controller (not shown) and a communications bus (not shown).

Those of skill in the art will understand that while generally described in conjunction with CT image data, that is a series of slice images that make up a 3D volume, the disclosure is not so limited and may be implemented in a variety of imaging techniques including magnetic resonance imaging (MRI), fluoroscopy, X-Ray, ultrasound, positron emission tomography (PET), and other imaging techniques that generate 3D image volumes without departing from the scope of the disclosure. Further, those of skill in the art will recognize that a variety of different algorithms may be employed to segment the CT image data set including connected component, region growing, thresholding, clustering, watershed segmentation, edge detection, and others.

Those of ordinary skill in the art will recognize that the methods and systems described herein may be embodied on one or more applications operable on a computer system for a variety of diagnostic and therapeutic purposes. As an initial matter, these systems and methods may be embodied on one or more educational or teaching applications. Further the methods and systems may be incorporated into a procedure planning system where structures, blood vessels, and other features found in the CT image data set are identified and a surgical or interventional path is planned to enable biopsy or therapy to be delivered at a desired location. Still further, these methods may be employed to model blood flow paths following surgery to ensure that tissues that are not to be resected or removed will still be sufficiently supplied with blood following the procedure. Those of skill in the art will recognize that a variety of additional and complementary uses of the image processing methods described herein.

Although the description of computer-readable media contained herein refers to solid-state storage, it should be appreciated by those skilled in the art that computer-readable storage media can be any available media that can be accessed by the processor. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by the workstation.

The application may, when executed by the processor, cause the display to present a user interface. The user interface may be configured to present to the user a variety of images and models as described herein. The user interface may be further configured to display and mark aspects of the images and 3D models in different colors depending on their purpose, function, importance, etc.

The network interface may be configured to connect to a network such as a local area network (LAN) consisting of a wired network and/or a wireless network, a wide area network (WAN), a wireless mobile network, a Bluetooth network, and/or the Internet. The network interface may be used to connect between the workstation and the imaging device. The network interface may be also used to receive the image data. The input device may be any device by which a user may interact with the workstation, such as, for example, a mouse, keyboard, foot pedal, touch screen, and/or voice interface. The output module may include any connectivity port or bus, such as, for example, parallel ports, serial ports, universal serial busses (USB), or any other similar connectivity port known to those skilled in the art.

While several aspects of the disclosure have been shown in the drawings, it is not intended that the disclosure be limited thereto, as it is intended that the disclosure be as broad in scope as the art will allow and that the specification be read likewise. For example, the systems and methods of the disclosure can form part of a platform for surgical planning applications for other organs or portions of the body including surgery, e.g., minimally-invasive cancer surgery, in the liver, the stomach, the intestines, the colon, the rectum, the prostate, the brain, the neck, the upper body, or the lower body; kidney transplant surgery; and vascular bypass and aneurysm repair, which requires using artificial intelligence (AI) to segment and classify many anatomical parts. Therefore, the above description should not be construed as limiting, but merely as exemplifications of particular aspects.

What is claimed is:

1. A system comprising:
a processor; and
a memory having stored thereon a neural network and instructions, which, when executed by the processor, cause the processor to:
cause the neural network to segment blood vessels in volumetric images of a portion of a body, yielding segmented blood vessels;
detect roots of the segmented blood vessels; detect endpoints of the segmented blood vessels;

determine a shortest path from each endpoint to each of the roots; and
combine the shortest paths to the roots into directed graphs.

2. The system of claim 1, wherein the instructions, when executed by the processor, further cause the processor to generate a 3D model based on the directed graphs.

3. The system of claim 1, wherein the neural network uses a 3D U-Net style architecture.

4. The system of claim 1, wherein the instructions, when executed by the processor, further cause the processor to:
receive annotated volumetric images in which blood vessels are identified;
train the neural network with the annotated volumetric images; and
segment blood vessels in the volumetric images using a classical image segmentation method, yielding the annotated volumetric images in which blood vessels are identified,
wherein the classical image segmentation method includes an edge-based method, a region-based method, or a thresholding method.

5. The system of claim 1, wherein the neural network includes a segmentation layer,
wherein the instructions, when executed by the processor, further cause the processor to train the segmentation layer with a dice loss, and
wherein the dice loss is a weighted dice loss.

6. The system of claim 1, wherein the neural network includes a topological layer, and wherein the instructions, when executed by the processor, further cause the processor to train the topological layer with a topological loss.

7. The system of claim 1, wherein the neural network includes a classification layer, and
wherein the instructions, when executed by the processor, further cause the processor to train the classification layer with a cross-entropy loss, a consistency loss, or both a cross-entropy loss and a consistency loss.

8. The system of claim 1, wherein the neural network includes:
an encoder configured to process the volumetric images and output an encoder output;
a first decoder coupled to the output of the encoder and configured to generate a segmentation probability map based on the encoder output; and
a second decoder coupled to the output of the encoder and configured to generate a topological embedding vector, a distance map, and a classification probability map based on the encoder output.

9. The system of claim 8, wherein the encoder, the first decoder, and the second decoder each include recurrent convolutional neural networks and squeeze and excite blocks coupled to the recurrent convolutional neural networks, respectively.

10. The system of claim 8, wherein the second decoder includes a convolution function and a sigmoid activation function that process the topological embedding vector and output the classification probability map.

11. The system of claim 8, wherein the second decoder includes a convolution function and a rectified linear unit that process the topological embedding vector and output the distance map.

12. A method comprising:
receiving a three-dimensional (3D) image data set of a portion of a body;

segmenting the 3D image data set to identify blood vessels in the 3D image data set using a neural network model;

classifying the blood vessels using the neural network model;

detecting starting points of the blood vessels using the neural network model; detecting endpoints of the blood vessels using the neural network model;

for each endpoint:

calculating optimal paths from possible starting points to the endpoint;

selecting a best starting point from possible starting points; and setting a class of a path from the best starting point to the endpoint; and merging paths of the same starting point into a tree structure.

13. The method of claim 12, wherein detecting starting points and ending points are performed using a neural network model.

14. The method of claim 12, further comprising:

training a segmentation layer of the neural network model using dice loss; and weighting the dice loss, wherein weighting the dice loss includes applying a weight of 0 to the dice loss for unannotated peripheral blood vessels and applying a weight of 1 for annotated peripheral blood vessels.

15. The method of claim 12, further comprising:

generating a 3D mesh model from the tree structure; and displaying the 3D mesh model in a user interface.

16. The method of claim 12, further comprising training a topological layer of the neural network model using a topological loss.

17. The method of claim 16, further comprising:

computing Euclidian distances of topological embedding vectors;

computing topological distances of the topological embedding vectors; and training the neural network model to match the Euclidian distance of topological embedding vectors to corresponding topological distances of the topological embedding vectors.

18. The method of claim 17, wherein computing the topological distances of the topological embedding vectors includes computing the topological distances of the topological embedding vectors based on total topological loss.

19. The method of claim 18, wherein the total topological loss is the sum of topological losses for pairs of points divided by the number of the pairs of points, wherein the topological loss for the pair of points is a value of an L1 smooth loss function of the pair of points, if the pair of points are in the same class, and wherein the topological loss for the pair of points is the maximum of 0 or 1/K multiplied by the difference between the constant K and an absolute value of the difference between network topological layer values corresponding to the pair of points, if the pair of points are not in the same class.

20. A method of generating directed graphs of blood vessels, the method comprising:

receiving a three-dimensional (3D) image data set of a portion of a body;

processing the 3D image data set with a neural network to generate a segmentation probability map of blood vessels in the 3D image data set;

closing at least one hole of the blood vessel in the segmentation probability map;

detecting starting points of the blood vessels;

detecting endpoints of the blood vessels;

for each endpoint:

tracking the shortest path from the endpoint to each of the starting points, yielding probable paths; and selecting the most probable path from the probable paths;

merging paths having a common starting point to one directed graph; and solving for at least one overlap between directed graphs.

* * * * *